United States Patent [19]
North et al.

[11] Patent Number: 6,114,502
[45] Date of Patent: Sep. 5, 2000

[54] GENE FAMILY ASSOCIATED WITH NEUROSENSORY DEFECTS

[75] Inventors: Michael North, San Diego, Calif.; Patsy Nishina; Juergen Naggert, both of Bar Harbor, Me.; Konrad Noben-Trauth, Rockville, Md.

[73] Assignee: AxyS Pharmaceuticals, Inc., South San Francisco, Calif.

[21] Appl. No.: 09/032,365

[22] Filed: Feb. 27, 1998

Related U.S. Application Data

[60] Continuation-in-part of application No. 08/904,699, Aug. 1, 1997, abandoned, which is a division of application No. 08/701,380, Aug. 22, 1996, Pat. No. 5,686,598, and a continuation-in-part of application No. 08/932,306, Sep. 17, 1997, abandoned, which is a division of application No. 08/706,292, Sep. 4, 1996, Pat. No. 5,705,380, and a continuation-in-part of application No. 08/630,592, Apr. 10, 1996, Pat. No. 5,770,432, and a continuation-in-part of application No. 08/714,991, Sep. 17, 1996, Pat. No. 5,776,762, and a continuation-in-part of application No. 08/850,218, Apr. 30, 1997, abandoned, and a continuation of application No. PCT/US97/05903, Apr. 10, 1997.

[51] Int. Cl.[7] .......................... A61K 38/17; C07K 14/435; C07K 19/00
[52] U.S. Cl. .......................... 530/324; 530/325; 530/326; 530/827; 530/839; 530/350
[58] Field of Search ..................... 530/350, 324, 530/325, 326, 827, 839

[56] References Cited

U.S. PATENT DOCUMENTS

| | | | |
|---|---|---|---|
| 5,646,040 | 7/1997 | Kleyn et al. | 435/325 |
| 5,686,598 | 11/1997 | North et al. | 536/23.5 |

OTHER PUBLICATIONS

Coleman and Eicher, "Fat (fat) and Tubby (tub): Two Autosomal Recessive Mutations Causing Obesity Syndromes in the Mouse," *Journal of Heredity* (1990) vol. 81:424–427.

Jones, et al., "Localization of Insulin–2 (Ins–2) and the Obesity Mutant Tubby (tub) to Distinct Regions of Mouse Chromosome 7," *Genomics* (1992) vol. 14:197–199.

Lee, et al., "Abnormal Splicing of the Leptin Receptor in Diabetic Mice," *Nature* (Feb. 1996) vol. 379:632–635.

Nishina, et al., "Characterization of Plasma Lipids in Genetically Obese Mice: The Mutants Obese, Diabetes, Fat, Tubby, and Lethal Yellow," *Metabolism* (May 1994) vol. 43:549–553.

Noben–Trauth, Konrad, et al., "A Candidate Gene for the Mouse Mutation Tubby", *Nature* (Apr. 11, 1996) vol. 380:534–538.

North, Michael A., et al., "Molecular Charaterization of TUB, TULP1, and TULP2, members of the Novel Tubby Gene Family and Their possible Relation to Ocular Diseases," *Proc. Natl. Acad. Sci. USA* (Apr. 1997) vol. 94:3128–3133.

Ohlemiller, at al., "Cochlear and Retinal Degeneration in the Tubby Mouse," *NeuroReport* (Apr. 1995) vol. 6:845–849.

Samuelson, et al., "Localization of the Murine Cholecystokinin A and B Receptor Genes," *Mammalian Genome* (1995) vol. 6: 242–246.

Zhang, et al., "Positional Cloning of the Mouse Obese Gene and its Human Homologue," *Nature* (Dec. 1994) vol. 372:425–432.

*Primary Examiner*—Christina Y. Chan
*Assistant Examiner*—F. Pierre VanderVegt
*Attorney, Agent, or Firm*—Pamela J. Sherwood; Paula A. Borden; Bozicevic, Field & Francis

[57] ABSTRACT

Nucleic acid compositions are provided that encode a family of mammalian proteins expressed in the retina and brain. Members of the gene family are genetically linked to various neurosensory defects, including cochlear degeneration, peripheral retinal degeneration and cone-rod retinal dystrophy. The nucleic acid compositions find use in identifying DNA sequences encoding homologous or related proteins; for production of the encoded protein; and in studying associated physiological pathways. In addition, modulation of the gene activity in vivo is used for prophylactic and therapeutic purposes, such as treatment of neurosensory defects, identification of retinal cells based on expression, and the like. The DNA is further used as a diagnostic for genetic predisposition to the linked neurosensory defect.

14 Claims, 3 Drawing Sheets

FIGURE 1

Human N terminal splicing

MGARTPLPSFWVSFTAETGILFPGGTPWPMGSQHSKQHRKPGPLKRGHRRDRRTTRRKYWKEGREIARVLDDEGRNLRQQKLDRQ....... TUB - 561

TUB - 518    MEPGTGAVLTEKSCCARQTSRLGHSVLDDEGRNLRQQKLDRQ........

TUB - 512    MEGVSSHRTLSYSRWSYDSVLDDEGRNLRQQKLDRQ........

TUB - 506    MTSKPHSDWIPYSVLDDEGRNLRQQKLDRQRALLEQKQKKKRQEPLMVQANA.........

TUB - 460    MVQANADGRPRSRRARQSEEQAPLVESYL........

Mouse N terminal splicing

MTSKPHSDWIPYSVLDDEGSNLRQQKLDRQRALLEQKQKKKRQEPLMVQANADGRPRSRRARQSEEQAPLVESYLSSS    tub - 505

MVQANADGRPRSRRARQSEEQAPLVESYLSSS    tub - 459

FIGURE 2A exon 0
AGAATTCAGCGGCCGCTGAATTCTAGCAAAGGCACCATGCCTCTGCGGGATGAAACCCTCCGAGAGGTGTGGGCCTCT
→← exon 1 →←
GACAGTGGGCATGAAGAAGAAAGCCTGAGCCCGGAGGCCCCGCGGCGCCCCAAACAGCGACCCGCCCCGACCCGCCCC

GGCACAGAGGCTAAGGAAGAAGAGGACGGAGGCCCCCGAATCCCCCTGCCCCACGGGATCCAAGCCCCGGAAGCCCGG

AGCTGGGCGGAGGGGGAGGCCGCGGGAGGAGCCTTCCCCAGACCCAGCCCAGGCCCGGGCGCCGCAGACGGTCTACGC
exon 2
CAGGTTCCTCAGGGACCCCGAGGCCAAGAAGCGCGACCCCCGGGAAACCTTTCTGGTAGCCCGTGCCCCAGACGCGGA
→← exon 3
GGACGAGGAGGAGGAGGAAGAGGAGGACGAGGAGGACGAGGAAGAGGAGGCAGAGGAAAAGAAAGAGAAAATCCTTCT
→←
GCCTCCCAAGAAGCCCCTGAGAGAGAAGAGCTCCGCAGACCTGAAGGAGAGGAGGGCCAAGGCCCAGGGCCCAAGGGG
exon 4
AGACCTGGGAAGCCCTGACCCCCCACCGAAACCTCTGCGTGTTAGGAATAAGGAAGCTCCAGCAGGGGAGGGGACCAA
→← exon 5
GATGAGAAAGACCAAGAAGAAAGGGTCTGGGGAGGCCGACAAGGACCCCTCAGGGAGCCCAGCCAGTGCGAGGAAGAG
→←
CCCAGCAGCCATGTTTCTGGTTGGGGAAGRCAGTCCTGACAAGAAAGCCCTGAAGAAGAAAGGCACTCCCAAAGGCGC
exon 6
GAGGAAGGAGGAAGAAGAGGAGGAGGAGGCAGCTACGGTGATAAAGAACAGCAATCAAAAGGGCAAAGCCAAAGGAAA
→←
AGGCAAAAAGAAAGCGAAGGAGGAGAGGGCCCCGTCTCCCCCCGTGGAGGTGGACGAACCCCGGGAGTTTGTGCTCCG
exon 7
GCCTGCCCCCCAGGGCCGCACGGTGCGCTGCCGGCTGACCCGGGACAAAAAGGGCATGGATCGAGGCATGTATCCCTC
→← exon 8
CTACTTCCTGCACCTGGACACGGAGAAGAAGGTGTTCCTCTTGGCTGGCAGGAAACGAAAACGGAGCAAGACAGCCAA
→←
TTACCTCATCTCCATCGACCCTACCAATCTGTCCCGAGGAGGGGAGAATTTCATCGGGAAGCTGAGGTCCAACCTCCT
exon 9
GGGGAACCGCTTCACGGTCTTTGACAACGGGCAGAACCCACAGCGTGGGTACAGCACTAATGTGGCAAGCCTTCGGCA
→← exon 10
GGAGCTGGCAGCTGTGATCTATGAAACCAACGTGCTGGGCTTCCGTGGCCCCCGGCGCATGACCGTCATCATTCCTGG
→←
CATGAGTGCGGAGAACGAGAGGGTCCCCATCCGGCCCCGAAATGCTAGTGACGGCCTGCTGGTGCGCTGGCAGAACAA
exon 11
GACGCTGGAGAGCCTCATAGAACTGCACAACAAGCCACCTGTCTGGAACGATGACAGTGGCTCCTACACCCTCAACTT
→←
CCAAGGCCGGGTCACCCAGGCCTCAGTCAAGAACTTCCAGATTGTCCACGCTGATGACCCCGACTATATCGTGCTGCA
exon 12
GTTCGGCCGCGTGGCGGAGGACGCCTTCACCCTAGACTACCGGTACCCGCTGTGCGCCCTGCAGGCCTTCGCCATCGC
CCTCTCCAGTTTCGACGGGAAGCTGGCTTGCGAGTGACCCAGCAGCCCTCAGCGCCCCAGAGCCCGTCAGCGTGG
GGGAAAGGATTCAGTGGAGGCTGGCAGGGTCCCTCCAGCAAAGCTCCCGCGGAAAACTGCTCCTGTGTCGGGCTGAC
CTCTCACTGCCTCTCGGTGACCTCCGTCCTCTCCCCAGCCTGGCACAGGCCGAGGCAGGAGGAGCCCGGACGGCGGGT
AGGACGGAGATGAAGAACATCTGGAGTTGGAGCCGCACATCTGGTTTCGGAGTTCGCCTGCCGCTGTGCCCCCCTC
CTCCCCGCGCCCCAGTCAATTCCTGTCCGGGAGCAGTAGTCATTGTTGTTTTAACCTCCCCTCTCCCCGGGACCGCGC
TAGGGCTCCGAGGAGCTGGGCGGGCTAGGAGGAGGGGGTAGGTGATGGGGACGAGGGCCAGGCACCCACATCCCCA
ATAAAGCCGCGTCCTTGGCA

FIGURE 2B

TULP2 exon 1
GGAATCCTCCCTCCCTCTGAGCCGTCTTTCTTCTCCTCCCTATTTCGCAGATATCCCGAGATTAGGTCCCCAGCTTCC
→← exon 2 →← exon 3
AAAGAGAGGATCAGAATGTCTCAGGATAATGACACATTGATGAGAGACATCCTGGGGCATGAGCTCGCTGCTATGAGG
→← exon 4
CTGCAGAAGCTGGAACAGCAGCGGCGGCTGTTTGAAAAGAAGCAGCGACAGAAGCGCCAGGAGCTCCTCATGGTTCAG
→←
GCCAATCCTGACGCTTCCCCGTGGCTTTGGCGCTCTTGTCTGCGGGAGGAGCGCCTTTTAGGTGACAGAGGCCTTGGG
exon 5
AACCCTTTCCTCCGGAAGAAAGTGTCAGAGGCACATCTGCCCTCTGGCATCCACAGTGCCCTGGGCACCGTGAGCTGT
→←
GGTGGAGACGGCAGGGGCGAGCGCGGCCTCCCGACACCGCGGACAGAAGCAGTGTTCAGGAATCTCGGTCTCCAGTCC CCTTTCTTATCCTGGCTCCCAGACAATTCCGATGCAGAATTGGAGGAAGTCTCCGTGGAGAATGGTTCCGTCTCTCCC
exon 6
CCACCTTTTAAACAGTCTCCGAGAATCCGACGCAAGGGTTGGCAAGCCCACCAACGACCCGTGCAGAGGGTGAGAGTG ACTCCCAGGATATGGGAGATGCACACAAGTCACCCAATATGGGACCAAACCCTGGAATGGATGGTGACTGTGTATATG
→←
AAAACTTGGCCTTCCAAAAGGAAGAAGACTTGGAAAAGAAGAGAGAGGCCTCTGAGTCTACAGGGACGAACTCCTCAG CAGCACACAACGAAGAGTTGTCCAAGGCCCTGAAAGGCGAGGGTGGCACGGACAGCGACCATATGAGGCACGAAGCCT
exon 7
CCTTGGCAATCCGCTCCCCCTGCCCTGGGCTGGAGGAGGACATGGAAGCCTACGTGCTGCGGCCAGCGCTCCCGGGCA CCATGATGCAGTGCTACCTCACCCGTGACAAGCACGGCGTGGACAAGGGCTTGTTCCCCCTCTACTACCTCTACCTGG
→← exon 8
AGACCTCTGACAGCCTGCAGCGCTTCCTCCTGGCTGGGCGAAAGAGAAGAAGGAGCAAAACTTCTAATTACCTCATCT
→←
CCCTGGATCCTACACACCTATCTCGGGACGGGGACAATTTCGTGGGCAAAGTCAGATCCAATGTCTTCAGCACCAAGT
exon 9
TCACCATCTTTGACAATGGGGTGAATCCTGACCGGGAGCATTTAACCAGGAATACTGCCCGGATCAGACAGGAGCTGG
→← exon 10
GGGCTGTGTGTTATGAGCCCAACGTCTTAGGATACCTGGGGCCTCGGAAAATGACTGTGATTCTCCCAGGAACCAACA
→←
GCCAGAACCAGCGAATCAATGTCCAGCCACTAAATGAACAGGAGTCGCTACTGAGTCGTTACCAACGTGGGGACAAAC
exon 11
AAGGGTTGCTTTTGTTGCACAACAAAACCCCGTCGTGGGACAAGGAGAACGGTGTCTACACGCTCAATTTCCATGGTC
→←
GAGTCACTCGGGCTTCGGTGAAGAACTTCCAAATCGTGGATCCCAAACACCAAGAACATCTGGTGCTCCAGTTCGGCC
exon 12
GAGTGGGCCCAGACACATTCACCATGGACTTCTGCTTTCCATTTAGCCCGCTCCAGGCCTTCAGCATCTGCTTGTCCA

GTTTCAATTAGAAGCTGGCTGTTGAATAACTCAATAAAATACCATACCCTTGCCAGC

GENE FAMILY ASSOCIATED WITH NEUROSENSORY DEFECTS

CROSS-REFERENCE TO RELATED APPLICATIONS

This application is a continuation in part of U.S. patent application Ser. No. 08/904,699, filed Aug. 1, 1997, now abandoned, which is a divisional of U.S. patent application Ser. No. 08/701,380, filed Aug. 22, 1996, now issued as U.S. Pat. No. 5,686,598. This application is a continuation in part of U.S. patent application Ser. No. 08/932,306, filed Sep. 17, 1997, abandoned, which is a divisional of U.S. Patent Application no 08/706,292, filed Sep. 4, 1996, now issued as U.S. Patent no. 5,705,380. This application is a continuation in part of U.S. patent application Ser. No. 08/630,592, filed Apr. 10, 1996, U.S. Pat. No. 5,770,432 and a continuation in part of U.S. patent application Ser. No. 08/714,991,filed Sep. 17, 1996, U.S. Pat. No. 5,776,762; and a continuation in part of U.S. patent application Ser. No. 08/850,218, filed Apr. 30, 1997, abandoned. This application is a continuation of PCT Application US97/05903, filed Apr. 10, 1997.

Sensory neurons give us our perception of the world, by transducing phenomena such as light and sound into signals that can be received and understood by the brain. However, neurons can also be fragile, and susceptible to a number of hereditary and/or age related degenerative disorders. Understanding the genes and gene products that comprise and control neurosensory signaling pathways may provide the basis for future medical advances in this area.

Neurodegenerative disorders result from the premature death of nerve cells in the brain and spinal cord; for example tracts of the acoustic system in degenerative hearing disorders. Such neuronal degeneration has been attributed to genetic defects, transmissible infectious agents, toxic substances, immune system disorders and other as yet undetermined mechanisms. A recent hypothesis is that active photoreceptor cell death, which is characteristic of these genetically distinct disorders, is mediated by a common induction of apoptosis.

Inherited eye disorders are the major cause of childhood blindness in the developed world. Many of these are retinal dystrophies. The retina is the sensory tunic of the eye, containing light sensitive receptors, a complex of neurons, and pigmented epithelium, arranged in discrete layers. In humans, the macula is the portion of the retina that lies directly behind the lens. Cones, the photoreceptor cells responsible for central vision, are heavily concentrated in the macula. The peripheral retina is composed mainly of rods, which are responsible for side and night vision.

Choroidoretinal dystrophies and degenerations, all of which are currently incurable and untreatable, are a common form of retinal dystrophy. Cone-rod retinal dystrophy (CRD) is a severe example, characteristically leading to early blindness. A loss of color vision and visual acuity is accompanied by widespread, advancing retinal pigmentation and chorioretinal atrophy of the central and peripheral retina. Linkage analysis of a large lineage of autosomal dominant CRD has mapped the disease to chromosome 1 9q, linked to the polymorphic marker D19S47. It has been suggested that the disease locus for CRD, which affects the central as well as peripheral retina, may also be involved in age-related macular degeneration (ARMD).

Hereditary peripheral retinopathies are also relatively common. Retinitis pigmentosa (RP), for example, affects approximately 1.5 million people worldwide. Substantial genetic heterogeneity has been observed in this condition, with over 20 chromosomal loci identified. A predisposition to retinitis pigmentosa can be inherited by autosomal dominant, autosomal recessive, X-linked or digenic modes. In spite of causal heterogeneity, there is significant clinical similarity among RP subtypes. Common signs and symptoms include early electroretinographic abnormalities, ophthalmoscopic findings, and progressively worsening tunnel vision.

It is interesting to note that the mouse mutation, tubby, leads to both retinal and cochlear degeneration, indicating a common element in both sensory pathways. It has also been observed that rare monogenic forms of human severe obesity are often accompanied by blindness and deafness: the best characterized are Bardet Biedl syndrome and Alstrom syndrome. Studying these diseases, although important in their own right, may also provide critical clues to the molecular mechanisms leading to an obese state.

The prevalence and clinical consequences of sensory neuronal defects make it of interest to characterize tubby and related genes that may be associated with vision and hearing defects.

Relevant Literature

Overviews of photoreceptor dystrophies may be found in Cotlier et al. (1995) *Surv. Ophthalmology* 40:51–61; Bird (1995) *Am. J. Ophthal.* 119:543–562; and Adler (1996) *Arch Ophthal.*114:79–83. Evans et al. (1994) *Nature Genetics* 6:210–213 describes the genetic mapping of cone-rod retinal dystrophy. Shugart et al. (1995) *Am J Hum Genet.* 57:499–502 disclose fine genetic mapping of a gene for autosomal recessive retinitis pigmentosa (RP 14) on chromosome 6p21. Berson (1996) *Proc Natl Acad Sci USA* 93:4526–4528 review retinitis pigmentosa.

Ohlemiller et al. (1995) *Neuroreport* 6:845–9 and Heckenlively (1995) *P.N.A.S.* 92:11100–11104 describe hearing loss and progressive retinal degeneration in tubby mice. The retinal degeneration is characterized by loss of photoreceptor cells, resulting in abnormal electroencephalograms by 3 weeks of age. Jones et al. (1992) *Genomics* 14:197–9 localize the tub locus to a specific region of chromosome 7, and demonstrate that it is distinct from the insulin-2 locus. The cholecystokinin receptor gene is shown to tightly linked to the tub locus in Samuelson et al. (1995) *Genome* 6:242–6. The mouse tub mutation is described in Coleman and Eicher (1990) *J Hered* 81:424–7 as an autosomal recessive mutation located on chromosome 7, which causes slowly developing but ultimately severe obesity.

Bennett et al. (1996) *Nature Medicine* 2:649 demonstrate that injection into rd/rd mice of a recombinant replication defective adenovirus that contains wild-type cDNA encoding βPDE delays photoreceptor death. Adenovirus vectors are described in Englehardt et al. (1993) *Nature Genetics* 4:27–34, and in Wang and Finer (1996) *Nature Medicine* 2:714.

SUMMARY OF THE INVENTION

Nucleic acid compositions are provided that encode a family of mammalian proteins expressed in the retina and brain. Members of the gene family are genetically linked to various neurosensory defects, including cochlear degeneration, peripheral retinal degeneration and cone-rod retinal dystrophy. The nucleic acid compositions find use in identifying DNA sequences encoding homologous or related proteins; for production of the encoded protein; and in studying associated physiological pathways. In addition, modulation of the gene activity in vivo is used for prophylactic and therapeutic purposes, such as treatment of neurosensory defects, identification of retinal cells based on expression, and the like. The DNA is further used as a diagnostic for genetic predisposition to the linked neurosensory defect. One family member, tub, is associated with mature onset obesity in an animal model, and may be used as in assays and therapies directed to preventing or treating obesity.

BRIEF DESCRIPTION OF THE DRAWINGS

FIG. 1 illustrates the N-terminal splicing at the human and mouse TUB locus. The sequences shown are: TUB-561, amino acids 1–85 of SEQ ID NO:10; TUB-518, amino acids 1–42 of SEQ ID NO:58; TUB-512, amino acids 1–36 of SEQ ID NO:60; TUB-506, amino acids 1–52 of SEQ ID NO:62; TUB-460, amino acids 1–29 of SEQ ID NO:8; tub-505, amino acids 1–78 of SEQ ID NO:4, and tub-459, amino acids 1–32 of SEQ ID NO:2.

FIG. 2A and FIG. 2B show the intron/exon boundaries for TULP1 [SEQ ID NO:12] and TULP2 [SEQ ID NO:14]. The arrows above the sequence lines indicate splice junctions.

DESCRIPTION OF THE SPECIFIC EMBODIMENTS

A family of genes whose members are associated with various defects in sensory neurons are provided (TULP family). Among the linked diseases are cochlear defects, retinitis pigmentosa (RP-14) and combined rod-cone dystrophy (CRD). Defects in the genes are also associated with a genetic predisposition to adult onset obesity. The nucleotide sequences of human and mouse cDNAs and genomic regions are provided. The coding region sequences are highly conserved between family members at the carboxy terminus, and variable at the amino terminus.

The nucleic acid compositions find use in identifying DNA sequences encoding homologous or related proteins; for production of the encoded protein; and in studying associated physiological pathways in vivo and in vitro. The nucleic acids are useful in modulating gene activity for diagnostic, prophylactic and therapeutic purposes, such as treatment of neurosensory defects, identification of retinal cells based on expression, and the like. The DNA is further used as a diagnostic for genetic predisposition to the specific genetically linked defect. The encoded proteins are useful as an immunogen to raise antibodies that specifically identify TULP expressing cells, in drug screening assays directed at neurosensory defects, and for therapeutic purposes. The amino terminal domain of TUB [SEQ ID NO:10, positions 1–139] has been shown to direct nuclear localization of the protein.

As used herein, the generic term "TULP" or "TULP family" designates the family of genes that includes the specific sequences provided in the SEQLIST and designated in Table 1. By family is intended one or more of the gene or gene products, up to and including TUB, TULP1, TULP2, TULP3 and TULP4. A family member is any one of the genes in the TULP family. Unless otherwise indicated, the sequences are of mammalian origin, and generally refer to the human sequences. In some animal models for TULP function, non-mammalian homologs, e.g. *C. elegans, D. melanogaster*, etc. are of interest. Within a species, the sequence similarity between family members is high in the carboxy terminal portion of the protein, where there is usually at least about 50% identity at the amino acid level. In tub and tulp4 different transcriptional products are formed by alternative exon splicing in the 5' end of the gene. All members of the TULP family are expressed in the retina, although not for all splice variants. In some cases the genes are also expressed in other tissues.

Exemplary members of the TULP gene family are as follows:

TABLE 1

TULP FAMILY MEMBERS

| SEQ ID NO | Sequence | Molecule | Size |
|---|---|---|---|
| 1 | Mouse tub Form I cDNA | dsDNA | 2119 bp |
| 2 | translation of above | amino acid | 459 aa |
| 3 | Mouse tub Form II cDNA | dsDNA | 2434 bp |
| 4 | translation of above | amino acid | 505 aa |
| 5 | tub mutation | dsDNA | 480 bp |
| 6 | translation of above | amino acid | 33 aa |
| 7 | Human TUB Form 6 cDNA | dsDNA | 1426 bp |
| 8 | translation of above | amino acid | 460 aa |
| 9 | Human TUB Form 1 cDNA | ds DNA | 3060 bp |
| 10 | translation of above | amino acid | 561 aa |
| 11 | Human TUB 5' region | genomic DNA | 5995 bp |
| 12 | Human TULP1 cDNA | ds DNA | 2115 bp |
| 13 | translation of above | amino acid | 542 aa |
| 14 | Human TULP2 cDNA | ds DNA | 1734 bp |
| 15 | translation of above | amino acid | 520 aa |
| 16 | Human TULP3 cDNA | ds DNA | 1482 bp |
| 17 | translation of above | amino acid | 442 aa |
| 18 | Mouse TULP4 cDNA | ds DNA | 1743 bp |
| 19 | translation of above | amino acid | 506 aa |
| 56 | Human TUB Form 1; 5' RACE | ds cDNA | 2112 bp |
| 57 | Human TUB Form 2; 5' RACE | ds cDNA | 2368 bp |
| 58 | translation of above | amino acid | 518 aa |
| 59 | Human TUB Form 3; 5' RACE | ds cDNA | 1936 bp |
| 60 | translation of above | amino acid | 512 aa |
| 61 | Human TUB Form 4; 5' RACE | ds cDNA | 1890 bp |
| 62 | translation of above | amino acid | 506 aa |
| 63 | Human TUB From 5; 5' RACE | ds cDNA | 2109 bp |
| 64 | Human TUB From 6; 5' RACE | ds cDNA | 2088 bp |

The sequences of the human and mouse tub cDNA and encoded protein sequences are provided as SEQ ID NO:1 through 10. The genomic region 5' to the human TUB locus is provided as SEQ ID NO:11. The cDNA and encoded protein sequences of splicing variants of the human TUB locus are provided as SEQ ID Nos:56 through 64. Six cDNA splice variants of TUB have been identified, and are designated as Form 1 through 6. The encoded proteins have a common carboxy-terminal sequence [SEQ ID NO:8], and vary in the amino terminal sequences. Forms 1 through 4 have unique amino termini; Forms 5 and 6 vary from each other only in the non-translated cDNA sequences.

As used herein, tub designates a coding region, gene or gene product that maps to the exact chromosomal position of the tub mutation described by Coleman and Eicher, supra, and mammalian, particularly human, homologs thereof. The human tub locus maps to chromosome 11, between the polymorphic markers D11S909 and D11S1331. It is expressed at high levels in brain, eye and testis, and at lower levels in various adult and fetal tissues, including small and large intestine, ovary and adipose tissue. Different transcriptional products are formed by alternative exon splicing in the 5' end of the gene.

The term "tub" or "tubby" encompasses both the normal mammalian sequence and the mutated sequence responsible for the tub phenotype. The tub mutation confers a genetic predisposition to maturity onset obesity in mice. The tub mutation is also associated with adult-onset degeneration of the retina and cochlea. The mutation in tub/tub mice is a G to T transversion at position 1704 resulting in a splicing defect and a truncated protein.

The sequence of the human TULP1 gene and its predicted protein product are provided as SEQ ID NOs:12–13. The TULP1 locus is associated with a predisposition to retinitis pigmentosa, form RP-14. TULP1 localizes to human chromosome 6p21. Two markers, D6S439 and D6S291, that flank TULP1 have been reported not to recombine with the RP 14 locus in a human kindred (Shugart et al. (1995) *Am J Hum Genet.* 57:499–502) demonstrating that TULP1 is tightly linked to the RP 14 locus. The expression of TULP1 is restricted to the retina.

Loss of function mutations in TULP1 have been shown to co-segregate with retinitis pigmentosa in kindred studies. Such mutations include but are not limited to a point mutation in exon 11 causing an amino acid substitution of Arg to Pro at a.a. 420 [SEQ ID NO:13]; and a point mutation in exon 12 causing an amino acid substitution of Phe to Leu at A.A 491 [SEQ ID NO:13]. The presently known polymorphisms that are associated with blindness are located in the conserved carboxy terminal portion of the protein.

The sequence of the human TULP2 gene and its predicted protein product are provided as SEQ ID Nos:14–15. The expression of TULP2 is restricted to the retina and testes. Retinal expression in adult tissue is relatively low. The TULP2 locus is associated with a genetic predisposition to combined rod cone dystrophy, a disease causing early chorioretinal atrophy of the central and peripheral retina. TULP2 is tightly linked to framework marker WI-9028 on chromosome 19q, which maps within the reported linked interval for CRD. The locus for rod cone dystrophy maps between D19S212 and D19S214.

The sequence of human TULP3 and its predicted protein product are provided as SEQ ID Nos:16–17. The human TULP3 gene maps to chromosome 12p13.2–12p13.3. The gene is expressed in the retina.

The sequence of mouse tulp4 and its predicted protein product are provided as SEQ ID Nos:18–19. Different transcriptional products are formed by alternative exon splicing in the 5' end of the gene. The syntenic location of TULP4 on the human chromosome is 19q.

TULP Nucleic Acid Compositions

Nucleic acids encoding TULP proteins may be cDNA, mRNA or genomic DNA, or fragment thereof. The term "gene" shall be intended to mean an open reading frame encoding a specific TULP polypeptide, as exemplified in Table 1, as well as trancribed adjacent 5' and 3' non-coding nucleotide sequences, in either direction. The gene may further encompass non-transcribed regulatory regions adjacent to the transcribed regions. The gene may be introduced into an appropriate vector for extra chromosomal maintenance or for integration into the host.

The term "cDNA" as used herein is intended to include all nucleic acids that share the arrangement of sequence elements found in native mature mRNA species, where sequence elements are exons, 5' non-coding regions and 3' non-coding regions. Normally mRNA species have contiguous exons, with the intervening introns deleted, to create a continuous open reading frame.

Genomic TULP sequences have non-contiguous open reading frames, where introns interrupt the coding regions. A genomic sequence of interest comprises the nucleic acid present between an initiation codon and stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 5 kb of flanking genomic DNA at either the 5' or 3' end of the coding region.

The genomic DNA may be isolated as a fragment of 50 kbp or smaller. A preferred genomic sequence will lack those sequences that are linked to TULP in a native chromosome but which do not contribute to the biological function of the TULP gene.

Genomic regions of interest include the non-transcribed sequences 5' to a TULP family gene, usually from about one to six thousand bp of sequence. This region of DNA contains the native promoter elements that direct expression of the linked TULP gene. The non-transcribed region 5' to human TUB locus is provided in SEQ ID NO:1 1. The 3' portion of this sequence [nt. 5535 to 5995; SEQ ID NO:11] is transcribed, but untranslated. The sequence of this 5' region may be utilized for promoter elements, including enhancer binding sites, that provide for expression in tissues where TUB is expressed. The tissue specific expression is useful for determining the pattern of expression, and for providing promoters that mimic the native pattern of expression. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 25 nt, usually at least 30 nt, more usually at least about 50 nt. Such small DNA fragments are useful as primers for PCR, hybridization screening, etc. Larger DNA fragments, i.e. greater than 100 nt are useful for production of fragments of the encoded polypeptide.

Where it is desirable to generate probes or primers that distinguish one family member from other members of the gene family, sequences may be derived from the less conserved region of the genes. Such sequences include the 3' terminus, of about one thousand bp., of each of the TULP family cDNA sequences. Probes useful for identifying homologous genes, or multiple family members may be derived from the conserved region of the genes, which includes roughly the 5' 500–1000 bp of each of the TULP family cDNA sequences.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA sequences are obtained in substantial purity, generally as a sequence other than a sequence of an intact mammalian chromosome. Usually, the DNA will be obtained substantially free of other nucleic acid sequences that do not include a TULP sequence or fragment thereof, generally being at least about 50%, usually at least about 90% pure and are typically "recombinant", i.e. flanked by one or more nucleotides with which it is not normally associated on a naturally occurring chromosome.

The DNA sequences may be used in a variety of ways. They may be used as probes for identifying other TULP genes, including novel family members, homologs and syntenic homologs. Identification of TULP homologs is based on similarity of sequence, chromosomal synteny, or both. The term homology is used to indicate a likeness of structure and conservation of biological function. Calculations of nucleic acid or amino acid sequence identity, as described below, provide a convenient method of identifying homologous or related genes, herein "homologs". Such homologs may be members of a gene family present in the same genome, or may be corresponding genes from different species. Chromosomal synteny may be used to further distinguish between homologous genes when there is sufficient evolutionary conservation between the genomes that are being compared, e.g. between mammalian species. A "syntenic homolog" has both sequence identity to the reference gene, and has the corresponding chromosomal location in relation to closely linked genes. Syntenic homologs have a high probability of sharing spatial and temporal localization of gene expression, and of encoding proteins that fill equivalent biological roles.

Mammalian homologs have substantial sequence similarity to the subject sequences, i.e. greater than 50% sequence identity with the amino acid or nucleotide sequence of the subject TULP sequence, as listed in Table 1. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithims for sequence analysis are known in the art, such as BLAST, described in Altschul et al. (1990) *J Mol Biol* 215:403–10.

Non-identical nucleic acids with sequence similarity are detected by hybridization under low stringency conditions, for example, at 50° C. and 10×SSC (0.9 M saline/0.09 M sodium citrate) and remain bound when subjected to washing at 55° C. in 1×SSC. By using probes, particularly labeled probes of DNA sequences, one can isolate homologous or related genes. The source of homologous genes may be any mammalian species, e.g. primate species, particularly human; murines, such as rats and mice, canines, felines, bovines, ovines, equines, etc.

For hybridization probes, it may be desirable to use nucleic acid analogs, in order to improve the stability and and binding affinity. A number of modifications have been described that alter the chemistry of the phosphodiester backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate,3'-S-5'-O-phosphorothioate, 3'-CH2-5'-O-phosphonate and 3'-NH-5'-O-phosphoroamidate. Peptide nucleic acids replace the entire phosphodiester backbone with a peptide linkage.

Sugar modifications are also used to enhance stability and affinity. The a-anomer of deoxyribose may be used, where the base is inverted with respect to the natural b-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Nucleic acid probes may also be used to identify expression of the gene in a biological specimen, e.g. retinal cells. The manner in which one probes cells for the presence of particular nucleotide sequences, as genomic DNA or RNA, is well-established in the literature and does not require elaboration here. A biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is fractionated by electrophoresis, e.g. capillary or gel electrophoresis, transferred to a suitable support, e.g. nitrocellulose and then probed with a fragment of the subject DNA as a probe. Other techniques may also find use, including oligonucleotide ligation assays, binding to solid state arrays, etc. Detection of mRNA having the subject sequence is indicative of TULP gene expression in the sample.

It will be understood by one of skill in the art that low basal levels of transcription are present in many normal cell types, or that a relatively rare cell type may have a high level of expression that cannot readily be detected in mRNA prepared from whole tissue. By specific expression, it is intended that mRNA levels are increased above the basal levels observed in other cells by at least about 100 fold, more usually by at least about 1000 fold. It will be further understood that malignant, or transformed, cells may express genes in an aberrant fashion.

The sequence of a TULP gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Synthesis of TULP Proteins

The subject genes may be employed for producing all or portions of the TULP proteins. For expression, an expression cassette may be employed, providing for a transcriptional and translational initiation region, which may be inducible or constitutive, where the coding region is under the transcriptional control of the transcriptional initiation region, and a transcriptional and translational termination region. Various transcriptional initiation regions may be employed which are functional in the expression host. In some cases, e.g. gene therapy vectors, it may be desirable to utilize the native promoter sequences as described above.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the TULP1 gene or fragment thereof, and a transcriptional termination region. Of particular interest is the use of sequences that allow for the expression of functional epitopes or domains, usually at least about 8 amino acids in length, more usually at least about 15 nucleotides in length, to about 25 amino acids, and up to the complete open reading frame of the gene. After introduction of the DNA, the cells containing the construct may be selected by means of a selectable marker, the cells expanded and then used for expression.

The peptide may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In many situations, it may be desirable to express the gene in mammalian cells, where the protein will benefit from native folding and post-translational modifications. Small peptides can also be synthesized in the laboratory.

With the availability of the protein in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 50% pure, preferably at least about 80% pure, and may be up to 90% or as much as 99% pure. Pure is intended to mean free of other proteins, as well as cellular debris.

A host may be treated with an intact TULP protein, or an active fragment thereof to modulate or reduce neurosensory and/or obesity-associated conditions. Desirably, the peptides will not induce an immune response, particularly an antibody response. Xenogeneic analogs may be screened for their ability to provide a therapeutic effect without raising an immune response. The protein or peptides may also be administered to in vitro cell cultures.

Various methods for administration may be employed. The polypeptide formulation may be given orally, or may be injected intravascularly, subcutaneously, peritoneally, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously. The amide bonds, as well as the amino and carboxy termini, may be modified for greater stability on oral administration.

The subject peptides may be prepared as formulations at a pharmacologically effective dose in pharmaceutically acceptable media, for example normal saline, PBS, etc. The additives may include bactericidal agents, stabilizers, buffers, or the like. In order to enhance the half-life of the subject peptide or subject peptide conjugates, the peptides may be encapsulated, introduced into the lumen of liposomes, prepared as a colloid, or another conventional technique may be employed that provides for an extended lifetime of the peptides.

The peptides may be administered as a combination therapy with other pharmacologically active agents. The additional drugs may be administered separately or in conjunction with the peptide compositions, and may be included in the same formulation.

The polypeptide is used for the production of antibodies, where short fragments provide for antibodies specific for the particular motif, and larger fragments or the entire protein allow for the production of antibodies over the surface of the polypeptide. Antibodies may be raised to the wild-type or variant forms of TULP protein. Antibodies may be raised to isolated peptides corresponding to these domains, or to the native protein, e.g. by immunization with cells expressing a TULP gene, immunization with liposomes having a TULP protein inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual,* Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Diagnostic Uses

The subject compositions have a number of diagnostic uses, either as isolated 20 family members, or as a panel of different sequences. The TULP genes and fragments thereof, encoded protein, and anti-TULP antibodies are useful in the identification of individuals predisposed to neurosensory degenerative conditions, e.g. cochlear degeneration and hearing loss; retinitis pigmentosa; combined rod cone dystrophy, etc. The characterization is useful in determining further treatment of the patient. Sequences 25 of interest for diagnostic purposes include but are not limited to the conserved portion of the molecule as previously described. The conserved regions are identified by sequence similarity, and conservation of intron/exon structure.

Specifically, TULP1 is associated with peripheral retinal dystrophies. In humans, TULP1 is tightly linked to the RP-14 locus. TUB is associated with retinal degeneration and cochlear degeneration in an animal model. TULP2 is associated with combined cone-rod dystrophy. In humans TULP2 is tightly linked to the CRD locus.

Loss of function mutations in TULP1 have been shown to co-segregate with retinitis pigmentosa in kindred studies. Such mutations include but are not limited to a point mutation in exon 11 causing an amino acid substitution of Arg to Pro at a.a. 420 [SEQ ID NO:13]; and a point mutation in exon 12 causing an amino acid substitution of Phe to Leu at A.A 491 [SEQ ID NO: 13].

TUB nucleic acids and proteins are also useful for diagnostic applications related to obesity. In mice carrying the tubby mutation, age related reduction in metabolic rate, rather than an increase in food intake, leads to accumulation of fat mass. Accumulation of fat mass and the severity of complications such as diabetes and atherosclerosis can be modified by genetic and environmental factors. The gene is expressed in the hypothalamus, and may be a component of signaling in the brain satiety center. TUB mutations that lead to a genetic predisposition to obesity may be determined by the use of the subject TUB sequences.

DNA from a patient having having one or more neurosensory defects is analyzed for the presence of a predisposing mutation in a TULP gene. The diagnosis may be performed in conjunction with kindred studies to determine whether a mutation of inteest co-segregates with disease phenotype in a family.

The presence of a mutated TULP sequence that affects the activity or expression of the encoded gene product may confer an increased susceptibility to the condition. Specific mutations of interest include any mutation that leads to neurosensory defects, e.g. retinal degeneration, including insertions, substitutions and deletions in the coding region sequence, introns that affect splicing, promoter or enhancer that affect the activity and expression of the protein.

For purposes of comparison and as an assay control, "normal" TULP sequences are provided in the SEQLIST, as described in Table 1. The normal sequence shall be understood to include sequence variants in non-coding regions that do not affect the level of expression of the gene, coding region variants that do not change the amino acid sequence, e.g. "third position" changes, and changes that result in an altered amino acid sequence but maintain substantially all of the normal protein function.

Biochemical studies may be performed to determine whether a candidate mutation in the coding region or control regions predisposes to disease. For example, the activity of a candidate TULP protein may be compared with the wild-type protein activity. A change in the promoter or enhancer sequence that downregulates expression may also result in predisposition to neurosensory defects. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, chloramphenical acetyltransferase, etc. that provides for convenient quantitation; and the like.

Retinal dystrophies of interest include retinitis pigmentosa, combined cone rod dystrophy, age related macular dystrophy, Stargardt's macular dystrophy, Best's disease, pigment pattern dystrophies, central alveolar choroidal dystrophy, dominant drusen, hereditary hemorrhagic macular dystrophy, North Carolina macular dystrophy, pericentral choroidal dystrophy, adult foveomacular dystrophy, benign concentric annular macular dystrophy, central aureolar pigment epithelial dystrophy, congenital macular coloboma, dominantly inherited cystoid macular edema, familial foveal retinoschisis, fenestrated sheen macular dystrophy, progressive foveal dystrophy, slowly progressive macular dystrophy, Sorsby's pseudoinflammatory dystrophy, progressive cone dystrophy, Leber's congenital amaurosis and Goldman-Favre syndrome.

A number of methods are used to determine the presence of a predisposing mutation in an individual. Genomic DNA is isolated from the individual or individuals that are to be tested, from any nucleated cellular source, such as blood, hair shafts, saliva, mucous, biopsy material, feces, etc. Where large amounts of DNA are available, the genomic DNA may be used directly. Alternatively, the region of interest is cloned into a suitable vector and grown in sufficient quantity for analysis, or amplified by conventional techniques. Cells that express TULP genes, such as retinal cells, may be used as a source of mRNA, which may be assayed directly or reverse transcribed into cDNA for analysis.

Methods using PCR amplification can be performed on the DNA from a single cell, although it is convenient to use at least about $10^5$ cells. A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein(6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high afifnity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. In one embodiment of the invention, an array of oligonucleotides are provided, where discrete positions on the array are complementary to at least a portion of mRNA or genomic DNA encoding one or more TULP proteins. Such an array may comprise a series of oligonucleotides, each of which can specifically hybridize to a nucleic acid, e.g. mRNA, cDNA, genomic DNA, etc. from one of the TULP family members. The complete array may include all of the TULP family members, including the splice variants of TUB. Wild-type sequences and polymorphisms may be represented. For example, see Hacia et al. (1996) *Nature Genetics* 14:441–447; Lockhart et al. (1996) *Nature Biotechnol.* 14:1675–1680; and De Risi et al. (1996) *Nature Genetics* 14:457–460.

Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The amplified or cloned fragment may be sequenced by dideoxy or other methods, and the sequence of bases compared to the normal sequence. Various methods are known in the art that utilize oligonucleotide ligation as a means of detecting mutations, see Riley et al. (1990) *N.A.R.* 18:2887–2890; and Delahunty et al. (1996) *Am. J. Hum. Genet.* 58:1239–1246. Alternatively, where the predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels.

Antibodies specific for TULP polymorphisms may be used in screening immunoassays. A reduction or increase in a TULP protein and/or presence of disease associated polymorphisms is indicative that a candidate neurosensory defect is TULP-associated. Immunoassays may utilize a patient sample from a patient suspected of having TULP-associated neurosensory defect. Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids.

Diagnosis may be performed by a number of methods. The different methods all determine the absence or presence or altered amounts of normal or abnormal TULP protein in patient cells suspected of having a predisposing polymorphism. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and TULP protein in a lysate. Measuring the concentration of TULP protein binding in a sample or fraction thereof may be accomplished by a variety of specific assays. A conventional sandwich type assay may be used. For example, a sandwich assay may first attach TULP-specific antibodies to an insoluble surface or support. Other immunoassays are known in the art and may find use as diagnostics. Ouchterlony plates provide a simple determination of antibody binding. Western blots may be performed on protein gels or protein spots on filters, using a detection system specific for TULP protein as desired, conveniently using a labeling method as described for the sandwich assay.

Regulation of TULP Gene Expression

The TULP genes are useful for analysis of expression, e.g. in determining developmental and tissue specific patterns of expression, and for modulating expression in vitro and in vivo. Modulation of expression may be used to up-regulate desired TULP genes in specific target tissues, e.g. retina, hypothalamus, etc., or to down-regulate undesired, e.g. disease-associated, TULP genes.

Of particular interest is intraocular gene delivery, e.g. sub-retinal injection, ocular implants, etc. The therapeutic gene is delivered through a suitable vector, e.g. a plasmid or viral vector. Viral vectors known in the art include modified retroviral genomes such as moloney leukemia virus and human immunodeficiency virus. Retroviral vectors typically include viral sequences that are required for packaging, integration and expression of the inserted TULP genes. The vectors are "defective" in the ability to encode viral proteins required for productive infection. Replication requires growth in a packaging cell line that provides the gag, pol, and env proteins necessary for completion of the infectious cycle. Adenovirus vectors are also of interest, as described in Li et al. (1994) *Invest. Ophthalmol. Vis. Sci.* 35:2543–2549; and Bennett et al. supra. Micro-injection may be employed, fusion, or the like for introduction of genes into a suitable host cell. See, for example, Dhawan et al. (1991) *Science* 254:1509–1512 and Smith et al. (1990) *Molecular and Cellular Biology* 3268–3271.

An expression vector will have a transcriptional initiation region oriented to produce functional mRNA. The native transcriptional initiation region, or an exogenous transcriptional initiation region may be employed. The promoter may be introduced by recombinant methods in vitro, or as the result of homologous integration of the sequence into a chromosome. Many strong promoters are known in the art, including the b-actin promoter, SV40 early and late promoters, human cytomegalovirus promoter, retroviral LTRs, methallothionein responsive element (MRE), tetracycline-inducible promoter constructs, etc.

Expression vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

Antisense molecules are used to down-regulate expression of TULP genes in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. Such modifications have been previously discussed with respect to the use of probes.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

Models for TULP Biological Function

The subject nucleic acids can be used to generate genetically modified non-human animals or site specific gene modifications in cell lines. The term "transgenic" is intended to encompass genetically modified animals having a deletion or other knock-out of TULP gene activity, or having an exogenous TULP gene that is stably transmitted in the host cells. Transgenic animals may be made through homologous recombination, where the TULP locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Investigation of gene function may also utilize non-mammalian models, particularly using those organisms that are biologically and genetically well-characterized, such as *C. elegans, D. melanogaster* and *S. cerevisiae*. For example, transposon (Tc1) insertions in the nematode homolog of a TULP gene, e.g. tub (f10b5.4) are made. The subject gene sequences may be used to knock-out or to complement defined genetic lesions in order to determine the physiological and biochemical pathways involved in TULP function. A number of human genes have been shown to complement mutations in lower eukaryotes. Drug screening may be performed in combination with complementation studies. Many mammalian genes have homologs in yeast and lower animals. The study of such homologs' physiological role and interactions with other proteins can facilitate understanding of biological function. In addition to model systems based on genetic complementation, yeast has been shown to be a powerful tool for studying protein-protein interactions through the two hybrid system described in Chien et al. (1991) *P.N.A.S.* 8:9578–9582.

The modified cells or animals are useful in the study of TULP function and regulation. For example, a series of small deletions and/or substitutions may be made in a TULP gene to determine the functional role of different domains.

Specific constructs of interest may include anti-sense TULP, which will block TULP expression, expression of dominant negative TULP mutations, and over-expression of a TULP gene. A detectable marker, such as lac Z may be introduced into the TULP locus, where upregulation of TULP expression will result in an easily detected change in phenotype.

These animals are also useful for exploring models of inheritance of neurosensory and obesity related disorders, e.g. dominant v. recessive; relative effects of different alleles and synergistic effects between TUB, TULP1, TULP2 and TULP3 and other disease genes elsewhere in the genome.

One may also provide for expression of the TULP gene or variants thereof in cells or tissues where it is not normally expressed or at abnormal times of development. In addition, by providing expression of TULP protein in cells in which it is otherwise not normally produced, one can induce changes in cell behavior.

DNA constructs for homologous recombination will comprise at least a portion of the TULP gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be used in functional studies, drug screening, etc., e.g. to determine the effect of a candidate drug on retinal disease.

Drug Screening Assays

By providing for the production of large amounts of TULP proteins, one can identify ligands or substrates that bind to, modulate or mimic the action of TULP protein. The protein may have the biological activity associated with the wild-type protein, or may have a loss of function mutation due to a point mutation in the coding sequence, substitution, insertion, deletion, etc., including scanning mutations as previously discussed.

Areas of investigation are the development of neurosensory defect or obesity treatments. Drug screening identifies agents that provide a replacement or enhancement for TULP function in affected cells. Of particular interest are screening assays for agents that have a low toxicity for human cells. A wide variety of assays may be used for this purpose, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions, transcriptional regulation, etc.

The term "agent" as used herein describes any molecule, e.g. protein or pharmaceutical, with the capability of altering or mimicking the physiological function of a TULP protein. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of neurosensory defect or obesity attributable to a defect in TULP gene or protein function. The compounds may also be used to enhance TULP function. The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

A pathway of particular interest is sensory neuron apoptosis. Mutations in the b subunit of cGMP phosphodiesterase cause retinal degeneration in mice with the rd1 mutation and in humans, and in rd1/rd1 mice an abnormal accumulation of cGMP appears to trigger apoptosis of the photoreceptor cells.

Drug screening assays may be performed with mutant and wild-type TULP protein to detect agents that mimic or act as agonists or antagonists for TULP function. The interaction of TULP protein with other proteins in these pathways is of particular interest, and may be detected in a variety of assays, e.g. yeast two hybrid system, in vitro protein-protein binding assays, genetic complementation, etc. There are a number of characterized genes and gene products that operate to regulate or effect apoptosis.

Complementation in animal and yeast models is particularly useful in the study of apoptosis. The genetics of programmed cell death has been well-defined in several animal models. Both C. elegans and D. melanogaster regulate apoptosis through the expression of two gene products, ced-3 and ced-9, and rpr and hid, respectively. The relative simplicity of these pathways is attractive for biochemical and genetic analysis. Both animals are used as screening tools in conjunction with the subject gene sequences, and with their corresponding TULP homologs.

A number of apoptotic and anti-apoptotic genes are expressed in neurons and photoreceptors, and may be involved in retinal degeneration. These cells depend on factors such as nerve growth factor and brain derived neurotrophic factor for survival, and may undergo apoptosis where the factor or its receptor are mutated. Among the anti-apoptotic genes of interest are bcl-2, bcl-xL and mcl-1. Inducers of apoptosis include fas (CD95), myc, bax, bcl-xs, TNF receptor and the family of cysteine proteases that includes interleukin 1 b- converting enzyme.

The availability of the subject gene sequences provides a means of analyzing the biology and biochemistry of specific neural degeneration through in vitro and in vivo drug screening, the use of transgenic animals, complementation of specific genetic lesions, etc., as previously described.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Identification of the Mouse Tubby Gene

The tubby mutation arose spontaneously in the C57BL/6J mouse strain. Homozygotes are recognizable by increased body weight at 3 to 4 months in males and at 4 to 6 months in females. Both sexes are fertile. The increased weight is composed of excess adipose tissue. Blood glucose is normal, but plasma insulin is increased prior to obvious signs of obesity and may rise to 20 times normal by 6 months. The islets of Langerhans are moderately enlarged with signs of hyperactivity and the mice display early onset retinal degeneration leading to blindness.

Materials and Methods

Genetic mapping of the tub locus. DNA samples isolated from the progeny of crosses between C57BL/6-tub/tub, CAST/Ei, AKR or NOD.NON-H2K$^b$ were genotyped for simple sequence length polymorphisms (Dietrich et al. (1994) *Nature Genet.* 7:220–245). All recombinants were progeny tested with a minimum of 20 offspring to confirm phenotypic classification. PCR amplification was performed as described in Naggert et al. (1995) *Nature Genet.* 10:135–141. The amplification primers used were as follows:

used as a template in PCR with a specific primer pair as shown above. Only pools comprising a YAC or P1 that contains the sequence tag defined by the primer pair will yield an amplification product. Then the process is repeated with the subpools corresponding to the positive superpools. In the YACS this process is continued until a single positive YAC can be identified. In the case of P1s, no subpools for the secondary pools exist, so that the secondary pools are plated, transferred to nylon filter and screened with the labeled sequence tag obtained with the specific primer pair. A positive P1 pool is then isolated.

Additional P1 and cosmid clones were made from YAC967d4, which spans most of the minimal genetic interval, and were used in direct cDNA selection against cDNA from adult testis, brain and eye of C57BL/6 mice. Ten randomly chosen cosmids were used in the cDNA selection . P1s used include 3636, 1848, 2617, Y, 14.6, 4171, 17.12, 4154, and 24.2. cDNAs for selection were a mixture obtained from testis, brain and eye mRNA. The selection was carried out as described by Lovett, *Current protocols in Human Genetics* (eds. Dracopoli et al.) 6.3.1–13 (Current Protocols, NY 1994) and modified by Segre et al. (1995) *Genomics* 28:549–559.

mRNA preparation. Whole organs from C57BL/6J and C57BL/6-tub/tub were flash frozen in liquid nitrogen, homogenized in 500 mM NaCl, 10 mM Tris pH 7.2, 10 mM EDTA, 2% SDS and incubated with 250 µg/ml proteinase K (EM Sciences, Gibbstown, N.J.) for 2 hours at 37° C. Oligo-dT cellulose (Pharmacia, Piscataway, N.J.) was added to the homogenate, placed on a shaking incubator for several hours and loaded onto PolyPrep chromatography column (BioRad, Richmond, Calif.). After washing in 100 mM NaCl, 10 mM Tris, pH 7.2, 0.1 mM EDTA, poly A$^+$ RNA was eluted in 10 mM Tris pH 7.2, 10 mM EDTA.

Northern blot analysis. 2–5 µg poly A$^+$ RNA was fractionated on a 1% agarose-formaldehyde gel, transferred to Hybond N+ membrane (Amersham) and hybridized with the indicated probes in the presence of 500 mM NaPO4, 7% SDS, 1 mM EDTA at 65° C. Blots were washed in 40 mM NaPO4, 1% SDS, 1 mM EDTA at 65° C., followed by a stringent wash in 0.1% SDS, 0.1×SSC at 68° C. Integrity, equal loading and transfer efficiency were assessed by control hybridization with a rat GAPDH probe.

An intron specific probe was generated by amplification of genomic PCR product of Cl3F2 and C13R with oligonucleotide primers Cl3F3 and C13R3. Nested PCR was used to generate the intron specific fragment in order to obtain a cleaner probe. Probe C15 was obtained by EcoRI digestion of the cDNA clone c15 from the cDNA selection. Probes were random labeled with $^{32}$P[αdCTP] (Amersham, Arling-

| Marker | Forward Primer | Reverse Primer |
|---|---|---|
| D7Pjn11 | SEQ ID NO:20<br>TTCACAAAAGCACACCTGG | SEQ ID NO:21<br>GTCCCAAGGATGGAGACCT |
| D7Pjn12 | SEQ ID NO:22<br>TGGTGAGCAAAACAAGGAAC | SEQ ID NO:23<br>TGGGGAAAGCAATTTCTGG |
| D7Pjn24 | SEQ ID NO:24<br>GCCTGTCAGCAAGGACCTT | SEQ ID NO:25<br>CCATGTCCCAAACAAGATGG |

YAC clones were obtained by PCR screening of mouse YAC DNA pools from Research Genetics, Inc. (Huntsville, Ala.) and P1 clones were obtained from Genome Systems (St. Louis, Mo.). Briefly, DNA from YAC or P1 pools was ton Heights, Ill.). Genomic DNA was PCR amplified with oligonucleotide primers flanking the donor splice site, Cl 3F2 and C13R, and was gel purified and manually sequenced by dideoxy cycle sequencing (Sequitherm, Epicentre Technologies, Madison, Wis.). Primer 2.61F1 was used with C13R to obtain a probe DNA fragment for northern blots by amplifying cDNA. Random hexamer priming, as described by Sambrook et al., supra, was used to label the amplification product.

| Primers | | |
|---|---|---|
| 2.61F | [SEQ ID NO:26] | ACCTGAGGCAGCAGAAGCT |
| C13R | [SEQ ID NO:27] | CAGCCAGTCTCTGGTTGGT |
| C13F2 | [SEQ ID NO:28] | TGCAGAACAAGACGCCAGT |
| C13F3 | [SEQ ID NO:29] | GATGTTGTACGCATGGTGC |
| C13R3 | [SEQ ID NO:30] | TGGAGACAGGGAGACCAGG |

Reverse transcription-PCR. RT-PCR was performed with RNA from adult tissues using primers 2.40R and 2.40F, or GAPDH. The tub gene specific primers span two introns with a combined length of about 1 kb. Two µg poly A+ RNA were treated with DNAse I (Boehringer Mannheim, Indianapolis, Ind.) and reverse transcribed using Super-script™ Preamplification System (Gibco/BRL, Gaithersburg, Md.). PCR was performed using 1–10 ng sscDNA, primer 2.40F [SEQ ID NO:31] GATGGCAA-GAAGGTGTTCC and 2.40R [SEQ ID NO:32] TCAT-TGCGGGGGCGGATAC and AmpliTaq™ (Perkin Elmer, Calif.) under the following conditions: 95° C. 1 min denaturation, 94° C. 20 sec, 58° C. 20 sec, 72° C. 30 sec for 49 cycles followed by 72° C. 2 min. Forward and reverse GAPDH oligomers were [SEQ ID NO:33] ATGGTGAAG-GTCGGTGTGAA and [SEQ ID NO:34] ACCAGTAGACTCCACGACAT, respectively. The amplification products were electrophoresed in 1 % agarose gel, transferred to Hybond N+ (Amersham) and hybridized with either exon or GAPDH cDNA probes.

cDNA library screening. A mouse testis cDNA library from mouse strain CD-1 (Stratagene, La Jolla, Calif.) inserted into lambda UNI-ZAP XR was screened according to the manufacturer's instructions with the 1.6 kb 2.61F-C13R PCR probe, identifying 24 plaques, two of which were purified and sequenced automatically (Prism, Applied Biosystems, Foster City, Calif.). Clone length was between 1 and 2.5 kb. The coding region cDNA sequence of Form I is described in the sequence listing, SEQ ID NO:1. The predicted amino acid sequence is SEQ ID NO:2. The coding region cDNA sequence of Form II is described in the sequence listing SEQ ID NO:3, the predicted amino acid sequence is SEQ ID NO:4.

Results

Genetic Mapping. Tubby was previously mapped in an interspecific (CS1BL/6-tub/tub×CAST/Ei)$F_1$ intercross to 2.4±1.4 cM from Hbb. Markers across a 20 cM interval encompassing Hbb were tested to identify areas of recombination and to define more closely the minimal tub region, using the DNA from the cross described above. Three mapping crosses were used to refine the minimal region containing the gene to between markers D7Mit94 and D7Mit325.

A total of 1468 meioses were tested in mapping outcrosses with CAST/Ei. 60 microsatellite markers were used, 91% of which were polymorphic between B6 and CAST. The minimal region containing tub identified by the CAST/Ei outcrosses was between markers D7Mit124 and D7Mit328 with a genetic distance of 0.27±0.14 cM.

In the NOD.NON-H2K$^b$ intercross with C57BL/6 tub/tub, 820 mice or 1640 meioses were tested. Initially, 680 meioses were tested proximally with D7Mit185 and distally with D7Mit130. As a narrower region was identified, 458 and 502 meioses were tested with proximal markers, D7Mit126 and D7Pjn2, respectively. Of 44 markers contained within the largest interval tested, 34 (77%) were polymorphic between C57BL-tub/tub and NOD.NON-H2K$^b$. Overall, 20 recombinant mice were identified in this intercross. The minimal region containing tub lay between markers D7Mit219 and D7Mit130 with a genetic distance of 0.18±0.11 cM.

775 $F_2$ progeny, or 1550 meioses, were tested with D7Mit126 and D7Mit130 as the flanking markers in the (C57BL/6-tub/tub×AKR)$F_1$ intercross. Only nine of the 34 markers mapping to this region were polymorphic between these parentals. The minimal genetic interval containing tub, between D7Pjn12 and D7Mit328, corresponds to a distance of 0.19±0.11 cM.

Physical Mapping. A YAC contig was established spanning the minimal genetic region, establishing order and distance for those markers not separated by recombinants. The minimal genetic interval was shown to be flanked by crossovers at D7Mit94 and D7Mit325, which could be mapped within P1 clones 524 and 242, respectively. The location of the tub gene relative to each crossover was unambiguously determined by progeny testing. Animals carrying crossovers in the region were mated to tub/tub homozygotes and the progeny examined for the tubby phenotype (50% tubby if the crossover chromosome still contained the tubby gene, 0% tubby if the crossover chromosome had lost the tubby gene).

Both flanking markers were shown to map within YAC67d4, giving a maximal physical separation of 650 kb. A high resolution physical map of the region was constructed by P1, BAC and cosmid assembly using STSs derived from end sequencing P1s, by subcloning and sequencing cosmid pools derived from YAC 132b11 (1 Mb, non-chimaeric) and by searching public databases.

Selected 0.6–1.5 kb cDNA clones were sequenced and analyzed for similarities to known sequences in GenBank using the BLASTN program (described in Altshul et al. (1990) *J. Mol. Bio.* 215:403–410), and for overlaps using the AssemblyLIGN program (Kodak, N.Y.). Unique cDNA clones and single clones from groups of overlapping clones were hybridized to Southern blots of EcoRI digested P1 DNA. Positive clones that mapped to the minimal region were analyzed for genomic alterations and aberrant expression between C57BL/6 and C57BL/6-tub/tub mice by Southern and northern blot analysis.

One cDNA clone, c33, from a DNA contig of 12 overlapping sequences, showed an altered hybridization pattern in tubby derived mRNA when compared to C57BL/6. Tubby mice express a slightly larger transcript in brain and testis, 6.6 kb vs. 6.3 kb. Furthermore, clone c33 identified a 2.1 kb transcript in tubby derived mRNA that is not observed in C57BL/6.

To determine the molecular basis of these differences, oligonucleotide primers were made according to the cDNA sequences from the contig of overlapping clones and used to PCR amplify gene specific fragments from cDNA and genomic DNA. Several oligonucleotide combinations derived from the carboxyterminal portion of the gene, as described above, generated an amplification product from tubby derived cDNA that was 300 bp longer than from C57BL/6 cDNA. The genomic nucleotide sequence was compared, and it was found that there was a G to T transversion in the tubby donor splice site, changing the wild-type donor splice site consensus sequence from GTGAGT to TTGAGT. To confirm that the larger transcript observed in tub was due to the presence of this unspliced carboxy terminal intron, a PCR generated probe specific for the intron was hybridized to a northern blot. The probe detected a transcript only in the tubby mRNA, but not in wild-type. Comparison of the sequence surrounding this donor splice site in standard inbred strain from historically independent lineages, AKR/J, BALB/cJ, DBA/2J, two wild-derived strains, CZECHII/Ei and SKIVE/Ei, as well as from rabbit and rat, showed conservation of the C57BL/6 sequence, suggesting that the nucleotide change is not a normal allelic form, but a mutation leading to the abnormal transcripts. The 2.1 kb transcript is likely to arise from truncation of the full length transcript by introduction of a polyadenylation site contained in the unspliced intron. This is supported by hybridization analysis with a sequence 3' of the unspliced intron, which does not hybridize to the 2.1 kb transcript.

Northern blot analysis of adult tissues shows strong expression of tubby in brain, eye and testis. Using a more sensitive RT-PCR assay, gene expression was also detected in the small and large intestine, ovary and adipose tissue of adult mice.

To assemble a full-length cDNA, 24 clones were isolated from a mouse testis oligo-dT primed cDNA library (Stratagene, La Jolla, Calif.). Two forms were identified. The sequence of Form I (SEQ ID NO:1) from nt 393–2579 is identical to Form II (SEQ ID NO:3) from nt 248–2434. The 5' end of the coding regions differ, resulting in a Form I protein that is 46 amino acids shorter than Form II.

The predominantly hydrophilic nature of the predicted amino acid sequence, and absence of a signal sequence, suggest a cytosolic localization for the protein. The carboxy terminal 260 amino acids show a strong similarity (62% identity) to a putative mouse testis-specific phosphodiesterase (GenBank accession number X69827), as well as the *C. elegans* 48.2K protein (GenBank Q09306, 59% identity). The aminoterminal portion of the tubby gene shows no similarity to any known protein in database searches (BLASTP).

Characterization of the Human Tubby Gene

The human tubby gene was isolated from a human cDNA library by the following methods.

A cDNA library generated from human brain mRNA and cloned into lambda gt11 (Clontech, Palo Alto, Calif.) was used to isolate the human tubby gene. The phage library was plated at $1.2 \times 10^6$ pfu/plate onto *E. coli* Y1090 in standard bacterial medium. The plates were incubated for 9 hours at 37° C. Two nitrocellulose filters were lifted from each plate as described in Sambrook et al., supra., pp.2.114. The filters were hybridized in 10% dextran sulfate, 1% SDS, 1M NaCl, 100 µg/ml salmon testes DNA and the $^{32}$P labeled probes described below, at 65° C. for 16 hr.

The hybridization probes are PCR amplification products of cDNA sequences isolated by exon trapping with the P1 clone 3636, as described in Example 1. The cDNA sequences were cloned into the pSPL3b vector (BRL, Bethesda, Md.) and amplified according to the manufacturer's instructions. A 171 bp probe was generated having the sequence of SEQ ID NO:35, and a 99 bp probe was generated having the sequence of SEQ ID NO:36. The DNA was labeled by random hexamer priming, as described in Example 1.

After hybridization, the filters were washed at 650C in a buffer of 2×SSC, 0.1% SDS for 45 min, followed by two washes in 0.2×SSC, 0.1% SDS for 45 minutes each. Positive plaques were isolated and rescreened. A total of 18 positive plaques were identified.

The cDNA inserts from the positive plaques were amplified by PCR and subcloned. Briefly, agar plugs containing positive phage plaques were picked, and resuspended in 10 mM Tris, 1 mM EDTA to elute phage. A PCR reaction was set up with phage eluate and primers specific for the region of lambda gt11 flanking the insert. The individual amplification products were digested with EcoRI, purified by gel electrophoresis and QIAEX II™ gel extraction kit (Qiagen), and inserted into pUC9 at the EcoRI site. The subcloned inserts ranged in size from 1.0–3.3 kb.

Nine of the plasmids were purified using a QIAGEN™ plasmid kit according to the manufacturer's instructions, and sequenced automatically (Prism, Applied Biosystems, Foster City, Calif.). The sequences were assembled, edited and analyzed using a suite of programs, including the BLASTN program (described in Altshul et al. (1990) *J. Mol. Bio.* 215:403–410), and for overlaps using the AssemblyLIGN program (Kodak, N.Y.). The human Form I cDNA sequence is shown in SEQ ID NO:7. The predicted amino acid sequence is shown in SEQ ID NO:8

Isolation of TULP1 cDNA

To identify tubby related genes involved in retinal degeneration, a human retinal cDNA library was screened with the conserved 3' coding region of human tubby gene as a probe, under low stringency conditions. The TULP1 gene was identified by this screening method. 77% aa identity was observed in the conserved region between TULP1 and TUB. In contrast to TUB, probing a variety of tissue northern blots with TULP1 showed no hybridizing bands. Thus, TULP1 expression is restricted to retina.

Gene specific PCR primers for TULP1 were used to determine its chromosomal location, using the Stanford G3 Radiation Hybrid panel. TULP1 localizes to chromosome 6p21.3. Two markers, D6S439 and D6S291, that flank TULP1 have been reported not to recombine with the RP 14 locus in a human kindred (Shugart et al. (1995) *Am J Hum Genet.* 57:499–502) demonstrating that TULP1 is tightly linked to the RP 14 locus.

Northern blot analysis of adult human tissues showed that TUB hybridized to a ~7–7.5 kb transcript with strong expression in heart, brain, testis, ovary, thyroid, and spinal cord after 48 hour exposure. It was also detected in skeletal muscle, prostate, small intestine, trachea and adrenal gland. A 2.4 kb TUB transcript was observed in liver and thyroid. No bands were observed on the same northern blots when hybridized with a TULP1 probe.

Methods

Adult brain cDNA isolation. To isolate the TUB gene, approximately $1.2–10^6$ plaque forming units of human adult brain cDNA lambda gt11 library were plated according to the manufacturer's instructions (Clontech). $^{32}$P labeled hybridization probes were prepared from two TUB sequences, ET-3636. p01.a04 (nt 1422 to 1593, 171 bp, GenBank Accession No. U52433) and ET-3636.p01.d01 (nt 1323 to 1421, 99 bp) by random hexamer priming, as described previously (Sambrook et al. Molecular Cloning: a Laboratory Manual 2nd ed. (Cold Spring Harbor Laboratory Press, Cold Spring Harbor, 1989)).

Filters lifted from the phage plates were hybridized with labeled probe in 10% dextran sulfate, 1 % SDS, 1 M NaCl, 100 μg/ml of salmon testes DNA, at 65° C. for 18 hr. After hybridization, filters were washed at 65° C. in 2×SSC, 0.1% SDS for 45 min; 0.2×SSC, 0.1% SDS for45 min and 0.2×SSC, 0.1% SDS for 45 min. Following plaque purification, cDNA inserts were PCR amplified using lambda gt11 primers (BRL) and directly cloned into pCR2.1 for sequencing, according to the manufacturer's instructions (Invitrogen). Automated fluorescence sequencing was utilized (Prism, Applied Biosystems).

Retinal cDNA isolation. To identify TULP1, approximately 1–10⁶ pfus of human retinal cDNA lambda gt11 library (Clontech) were hybridized as described above with a ³²P labeled-EcoRI/Sac II fragment (1–962 bp) of Image EST clone 221670 (Research Genetics, Genbank accession no. H92408) at 65° C. overnight. The membranes were washed sequentially for 1 hour each with 2×SSC, 0.1% SDS at 50° C., 1×SSC, 0.1% SDS at 50° C., and 0.5×SSC,0.1% SDS at 60° C. Positive plaques were purified and processed as above.

Full length cDNA. To isolate the flanking 5' sequences, the Marathon-Ready cDNA kit (Clonetech) was used according to manufacturer's protocol. Amplifications products were gel purified (Qiagen) and sequenced automatically (Prism, Applied Biosystems) or manually by dideoxy cycle sequencing (Sequitherm, Epicentre Technologies). Alternately, gel purified products were subcloned into TA cloning vector according to manufacturer's instruction (BRL), electroporated into DH10B cells, grown, and plasmids isolated by standard protocol prior to sequencing (Ausubel, et al. *Current Protocols in Molecular Biology.* Greene Publishing Associates and Wiley-lnterscience, New York, updated to 1995).

Southern analysis. Genomic DNAs from a number of animal species were digested with EcoR I and the DNA transferred to nylon membranes by standard protocol (Clontech). The membranes were hybridized with ³²P labeled Hind Ill fragment(281–1833 bp) of TUB cDNA, and ³²P labeled-EcoRI/BstX I fragment containing the 5' 365 bp of Image EST clone 221670, which contains the 3' end of TULP1. Blots were washed in 2×SSC, 0.05% SDS at room temp. for 2–10 min. and at 60° C. for 20 min, then twice with 0.2×SSC, 0.1 % SDS at 60° C. for 20 min. each.

Northern analysis. Human multiple tissue northern blots MTN I, II and III (Clontech) were hybridized with the ³²P labeled Hind Ill fragment(281–1833bp)of TUB cDNA and ³²P labeled-EcoRl/BstXI fragment of Image EST clone 221670 in 5× SSPE, 10× Denhardt's, 2% SDS, 100 μg/ml of sheared salmon sperm DNA and 50% formamide at 42° C. for 18 hr, then washed at 2×SSC, 0.05% SDS at room temperature for 3×10 min, and at 0.1×SSC, 0.1% SDS at 50° C. for 2×20 min.

Radiation hybrid mapping. Oligonucleotide primers for PCR amplification were constructed from the novel 5' end of TUB, generating a product of 225 bp for cDNA and ~850 bp for genomic DNA:

(SEQ ID NO:37) CTTAAACCCACTCCATCCTGTG (SEQ ID NO:38) ATCTCCCTTCCTTCCTTCCAGT.

Amplification primers for the 3' non-coding region for TUB, generating a product of 221 bp were constructed:

(SEQ ID NO:39) TGCCTGGGAATCCTGCTGC;

(SEQ ID NO:40) TCCTAAGGGTCCTGCCACT.

For TULP1, generating a product of 92 bp, the following primers were constructed:

(SEQ ID NO:41) CGAAAACGGAGCAAGACAG;

(SEQ ID NO:42) TATGAGGCTCTCCAGCGTC.

The MacVector computer program (Oxford) was used to design primer sets. After confirming by sequencing that the appropriate product was amplified, the retention patterns for each oligonucleotide pair were obtained by PCR assay in the Stanford G3 Radiation Hybrid panel (Cox et al. (1990) *Science* 250:245–250). Data entered into an online database was analyzed by RHMAP software developed by Boehnke et al. (1991) *Am J Hum Genet* 49:1174–1188. It is evident from the above results that TULP1 is a novel human gene expressed specifically in retinal tissue. The chromosomal location of TULP1 is tightly linked to the locus for retinitis pigmentosa 14.

Loss of function mutations in TULP1 have been shown to co-segregate with retinitis pigmentosa in kindred studies. Such mutations include but are not limited to a point mutation in exon 11 causing an amino acid substitution of Arg to Pro at A.A. 420 [SEQ ID NO:13]; and a point mutation in exon 12 causing an amino acid substitution of Phe to Leu at A.A 491 [SEQ ID NO:13].

Isolation of TULP2 cDNA

The human TULP2 gene was isolated from a human cDNA library by the following methods.

TULP2 was identified as a member of the tubby gene family. TULP2 cDNA was isolated by hybridization of a probe from the mouse p46 sequence, at reduced stringency, to a human cDNA library. The mouse p46 gene was previously identified as a cDNA sequence in a public database, with homology to tubby. TULP2 extends approximately 700 bp further than p46 on its 5' end, and has numerous nucleotide differences throughout the length of the gene. The p46 sequence has the GenBank accession number X69827.

Approximately 1×10⁶ pfu of human testis cDNA library in lambda DR2 (Clontech) were plated according to the manufacturer's instructions, using K802 as bacterial host. After over night incubation at 37° C., 2 membranes were lifted from each plate. Those membranes were hybridized in 10% dextran sulfate, 1% SDS, 1M NaCl, 100 μg/ml of salmon testes DNA and ³²P labeled probes at 65° C. for 16 hr.

The labeled probe was a PCR amplification product from a mouse testis cDNA library, using primers MP46.1 (SEQ ID NO:43) 5'-TCTACAGAGACAAACTATGCCC-3' and MP46.2 (SEQ ID NO:44) 5'-GGAAATGTGCTACACCATC CTC-3', which were designed using the published mouse P46 gene sequence. After hybridization, 3 washes were performed at 55° C.: 2×SSC, 0.1% SDS for 45 min, 0.2×SSC, 0.1% SDS for 45 min, 0.2×SSC, 0.1% SDS for 45 min. 34 positive plaques were detected after overnight exposure with X ray film. 28 positive clones were isolated after tertiary screening. The positive TULP2 clones were converted to plasmid DNA following the manufacturer's protocol and sequenced according to standard protocols.

Human multiple tissue northern blots MTNI, II and III (Clontech)were hybridized with the ³²P labeled PCR amplification product of TULP2, using primers HP46.F1 (SEQ ID NO:45) 5'-CCACTAAATGAACAGGAGTCGC-3' and HP46.R1 (SEQ ID NO:46) 5'-GAAACTGGACAAGCAGATGCTG-3'. The probe corresponds to nt 1360–1650 of TULP2 (SEQ ID NO:14). The hybridization was done in Express Hyb solution (Clontech) at 60° C. for 2 hr, according to the manufacturer's instructions. The blots were washed 3 times in 2×SSC, 0.05% SDS at room temp, followed by washing with 0.1×SSC, 0.1 % SDS at 55° C. 2×40 min., with 0.1×SSC,0.1% SDS at 65° C. for 40 min. The TULP2 transcript was detected only in testis, with an approximate size of 1.8 kb.

In order to detect retinal expression, a human retinal cDNA library (Clontech) was plated, and filters lifted, as described above. Using the same TULP2 probe and hybridization conditions, positive plaques were identified at a frequency of 1/10⁶ plaques, indicating low level expression in adult retina tissue.

The genomic location of TULP2 was mapped using the Genebridge radiation hybrid panel. Oligonucleotide primers for PCR amplification were constructed from the 2nd exon from 3' end of TULP2 (position 1360–1521), generating a product of 162 bp in both cDNA and genomic DNA. The primers used were:

(SEQ ID NO:47) HP46.F1 5'-CCACTAAATGAACAG-GAGTCGC-3'

(SEQ ID NO:48) HP46.R2 5'-TTGGAAGTTCTTCAC-CGAAGCC-3'

The PCR conditions were 94° C.,45 sec; 55° C.,45 sec; 72° C.,60 sec for a total of 30 cycles. After confirming by sequencing that the appropriate product was amplified, the retention patterns for each oligonucleotide pair were obtained by PCR assay in the Genebridge radiation hybrid panel (see Walter et al. (1994) Nature Genetics 7:22–28). Data entered into an online database was analyzed by RHMAP software developed by Boehnke et al. (1991) *Am J Hum Genet* 49:1174–1188. The public domain mapping data may be obtained through the Whitehead Institute/MIT Center for Genome Research, Human Genomic Mapping Project, Data Release 10 (May 1996). This data corresponds to the integrated maps announced in Hudson et al. (1995) *Science* 270:1945–1954. Hudson et al. provide a detailed description of the materials and methods used to construct these maps. Further mapping information may be found in Dib et al. (1996) Nature 380:152–154.

The Genebridge mapping data for TULP2 and WI-9028 is as follows:
WI-9028

000000000100000000101000000001000000001011001100011 000000000011110010

010010000000002011100201

TULP2

000000000100000010101000001001000000001011001100011 10000000000010110010

000010000000002011100201

These data indicate that the TULP2 gene is most tightly linked (with lod>3) at 3.05 cR to framework marker WI-9028, which maps within the reported linked interval for 19q rod cone retinal dystrophy. The gene for rod cone dystrophy maps between D19S212 and D19S214.

It is evident from the above results that a novel member of the tubby gene family has been characterized. TULP2 is expressed in the testes and retina, but not in other adult tissue. Genomic mapping data indicate that the gene is closely associated with the locus for cone-rod retinal dystrophy, a disease causing early chorioretinal atrophy of the central and peripheral retina.

FIG. 2 shows a comparison of the intron-exon structure of human TULP1 and TULP2. The intron exon boundaries were determined by comparison of the cDNA sequence to the corresponding genomic sequence obtained by direct sequencing of bacterial artificial chromosomes encompassing the TULP2 or TULP1 genomic locus. The intron exon structure is highly conserved at the sequences encoding the carboxy terminal portion of these molecules, and highly divergent over sequences encoding the amino terminal portion. These are sequences that are highly conserved in the TULP family across divergent species. Loss of function mutations that have been identified in TULP1 map to the conserved regions.

Isolation of TULP3 cDNA

In order to isolate a sequence tagged site for TULP3 from genomic DNA, degenerate primers from the highly conserved C-terminus of the TULP family were prepared and used to amplify anonymous human genomic DNA. Primers Mand-F [SEQ ID NO:66] (5'-GCITCIGTIAAGAACTTYCAGMT-3' and Mand-R [SEQ ID NO:67] (5'-CTKSWIAIISMIATIGCRAAIGCYTG-3') were used under standard reaction conditions.

Ramping PCR conditions were used: 95° C. for 2 min, then 5 cycles of 95° C. for 5 sec., 40° C. for 10 sec., 72° C. for 40 sec., followed by 30 cycles at 95° C. for 5 sec, 50° C. for 10 sec., 72° C. for 40 sec., followed by an final extension at 72° C. for 7 min. The products obtained from this reaction were subcloned and sequenced according to standard protocols. The new sequences corresponding to new TULP family members were then used to design primers for RACE (rapid amplification of cDNA ends) amplification of retina cDNA, as described below.

In order to detect retinal expression, an adaptor ligated human retinal double-stranded cDNA library (Marathon-Ready cDNA, Clontech) was amplified using a kit for Marathon cDNA amplification for 5' and 3'-RACE (Clontech). For amplification, 0.2 ng of cDNA was subjected to 5' Marathon RACE using a Tth-XL amplification kit (Perkin-Elmer) with the primers Ap-1 [SEQ ID NO:49] (5'-CCATCCTAATACGACTCACTATAGGGC-3', Clontech) and the h5.7R1 primer [SEQ ID NO:50] (5'-AATCCAGTGTGAACACGTCAT-3'). PCR reactions were performed in a MJ Research PTC-100 cycler with the following program: 37 cycles of 94° C. for 5 sec, 54° C. for 10 sec. 72° C. for 2 min., followed by a final extension at 72° C. for 7 min.

For the secondary, nested, PCR reaction a 1/50 dilution of the first 5' RACE reaction was prepared and the Marathon RACE reaction was again performed using 2 ul of the diluted product, the Tth-XL amplification kit (Perkin-Elmer), substituting the Ap2 [SEQ ID NO:51] (5'-ACTCACTATAGGGCTCGAGCGGC-3', Clontech) and the h5.7R2 [SEQ ID NO:52] (5'-CACGTCCAAACTGCATGACT-3') primers.

PCR reactions were performed in a MJ Research PTC-100 cycler with the following program: 27 cycles of 94° C. for 5 sec, 54° C. for 10 sec, 72° C. for 2min., followed by a final extension at 72° C. for 7 min. The resulting product was run on a 1.2% agarose gel, stained with EtBr, and a ~1.3 kb band was excised. The DNA was isolated from the agarose using a QIAquick gel extraction kit (Qiagen) and recovered in 50 ul TE buffer.

The 3' RACE reaction was similarly performed. Thus the 3'Marathon RACE reaction was performed on 0.2 ng of cDNA using the Tth-XL amplification kit (Perkin-Elmer), along with the Ap1 primer [SEQ ID NO:51] (5'-CCATCCTAATACGACTCACTATAGGGC-3', Clontech)

and the h5.7-F5 primer [SEQ ID NO:53] (5'-GCCCCCGTCTGGAACAGTG-3'). PCR reactions were performed in a MJ Research PTC-100 cycler with the following program: 37 cycles of 94° C. for 5 sec, 54° C. for 10 sec, 72° C. for 2 min., followed by a final extension at 72° C for 7 min. For the secondary, 'nested', PCR reaction a 1/50 dilution of reaction 1 was prepared and the 3' Marathon RACE reaction was performed using 2 ul of the diluted product in a 20 ul reaction of the Tth-XL amplification kit (Perkin-Elmer), along with the Ap2 primer [SEQ ID NO:54] (5'-ACTCACTATAGGGCTCGAGCGGC-3', Clontech) and the h5.7-f5 primer [SEQ ID NO:55] (5'-GCCCCCGTCTGGAACAGTG-3'). The PCR reaction were again performed in the MJ Research PTC-100 cycler with the following program: 27 cycles of 94° C. for 5 sec, 54° C. for 10 sec, 72° C. for 2 min., followed by a final extension at72° C. for7 min. The resulting product was run on a 1.2% agarose gel, stained with EtBr and a ~500 bp band was excised and weight. DNA was isolated using the QIAquick gel extraction kit.

The DNA sequence was obtained by directly sequencing the 5' and 3' RACE products by automated sequencing on an ABI 480 sequencing system using the h5.7 F5 and h5.7 R2 primers.

Characterization of TUB Splice Variants

Western analysis demonstrates that TUB protein is expressed in a variety of human tissues, including brain, colon, heart, skeletal muscle and stomach. TUB function is therefore not restricted in neuronal tissues. The pattern of protein expression is consistent with the pattern of mRNA expression observed by Northern blot analysis. Western blot analysis also indicates that multiple protein products observed in both neuronal and non-neuronal tissues, ranging in size from 36 kDa to 98 kDa. Using 5' RACE PCR, a series of alternative spliced forms of human tubby were identified, which can account for these alternative protein products, and which will have different biochemical activities.

There are 6 alternative 5' ends for the TUB transcript, which lead to different amino acid sequences of the N terminus. The predicted amino acid sizes for each TUB protein form are listed, along with the SEQ ID NO of the appropriate 5' RACE product.

Forms 1–4 are identical in their 3' end sequence from residue 69 to 561 [SEQ ID NO:10], and vary in the 5' sequence as shown. Forms 5 and 6 are spliced such that translation initiation occurs at an internal methionine at residue 102 [SEQ ID NO:10] and leading to a predicted protein of 460 amino acids [SEQ ID NO:8]. The alternative splicing form has been observed in both mouse (tub) and human (TUB) transcripts.

| Form | Length AA | Protein SEQ NO | cDNA SEQ NO |
|---|---|---|---|
| Form 1 | 561 aa | SEQ ID NO: 10 | SEQ ID NO: 9 |
| Form 2 | 518 aa | SEQ ID NO: 58 | SEQ ID NO: 57 |
| Form 3 | 512 aa | SEQ ID NO: 60 | SEQ ID NO: 59 |
| Form 4 | 506 aa | SEQ ID NO: 62 | SEQ ID NO: 61 |
| Form 5 | 460 aa | SEQ ID NO: 8 | SEQ ID NO: 63 |
| Form 6 | 460 aa | SEQ ID NO: 8 | SEQ ID NO: 64 |

Subcellular localisation directed by alternative splicing of TUB

Clontech vector pEGFP-C was used as the source of green fluorescent protein (GFP). In all the constructs described herein the GFP protein was tagged at the amino terminus of the chimeric protein. Electroporation was used to obtain a transient transfection of Cos7 cell with these expression plasmids. After 8–24 hours of transfection, the cells were fixed with 4% paraformaldehyde and examined using a fluorescence microscope to determine the subcellular localisation of the construct.

| construct | length (aa) | GFP Localization | Protein SEQ ID NO |
|---|---|---|---|
| TUB 561 | 561 | nuclear | SEQ ID NO: 10 |
| TUB N | 285 | nuclear | SEQ ID NO: 10 residues 1–285 |
| TUB del3 | 422 | cytoplasmic | SEQ ID NO: 10 residues 140–561 |
| TUB C | 276 | cytoplasmic | SEQ ID NO: 10 residues 286–561 |
| GFP only | | cytoplasmic | |

Taken together these data define a 139 amino acid sequence (SEQ ID NO:10, residues 1–139), capable of nuclear localisation. The domain is common to TUB 561 and TUB N, and is absent from TUB del3 and TUB C. The specific amino acid sequences within this domain which are necessary for nuclear localisation remain to be defined, although the motif [SEQ ID NO:65] KKKRQ has previously been shown to direct nuclear transport.

A distinct (predominantly) cytoplasmic location for TUB 506 [SEQ ID NO:62] is indicated by GFP assays described above, and by immunohistochemistry in mouse brain sections, where cytoplasmic rather than nuclear staining is obvious. The major form of mouse tubby protein in adult brain has been previously shown to be homologous to SEQ ID NO:62.

Immunohistochemistry method:

Mouse adult brain section was obtained using standard procedure. After deparaffinization and hydration of the tissue section, slides were blocked with 3% normal goat serum. The primary antiserum from rabbit used for this study was raised against recombinant human TUB fragment (exons 7 to 12). After overnight incubation with primary antibody at 4° C., the slides were washed several times and incubated with biotinylated anti-rabbit-IgG for 30 min at room temperature. Slides were washed again and incubated with fluorescein streptavidin for another 30 min at room temperature. After that, the slides were washed and mounted with anti-fade mounting medium containing 200 ng/ml DAPI.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A purified polypeptide composition comprising at least 50 weight % of the protein present as a protein comprising an amino acid sequence selected from the group consisting of SEQ ID NO: 13: SEQ ID NO:15; SEQ ID NO:17; SEQ ID NO:19; SEQ ID NO:10; SEQ ID NO:58; and SEQ ID NO:60.

2. A purified polypeptide composition according to claim 1, wherein said protein is a fusion protein comprising an exogenous fusion peptide.

3. The purified polypeptide composition according to claim 1, wherein said protein consists of the amino acid sequence set forth in SEQ ID NO:13.

4. The purified polypeptide composition according to claim 1, wherein said protein consists of the amino acid sequence set forth in SEQ ID NO:15.

5. The purified polypeptide composition according to claim 1, wherein said protein consists of the amino acid sequence set forth in SEQ ID NO:17.

6. The purified polypeptide composition according to claim 1, wherein said protein consists of the amino acid sequence set forth in SEQ ID NO:19.

7. The purified polypeptide composition according to claim 1, wherein said protein consists of the amino acid sequence set forth in SEQ ID NO:10.

8. The purified polypeptide composition according to claim 1, wherein said protein consists of the amino acid sequence set forth in SEQ ID NO:58.

9. The purified polypeptide composition according to claim 1, wherein said protein consists of the amino acid sequence set forth in SEQ ID NO:60.

10. A purified polypeptide composition comprising at least 50 weight % of a protein consisting of the amino acid sequence as set forth in SEQ ID NO:15, or a fragment of at least 25 amino acids thereof.

11. A purified polypeptide composition comprising at least 50 weight % of a protein consisting of the amino acid sequence as set forth in SEQ ID NO:17, or a fragment of at least 25 amino acids thereof.

12. A purified polypeptide composition comprising at least 50 weight % of a protein consisting of the amino acid sequence as set forth in SEQ ID NO:19, or a fragment of at least 25 amino acids thereof.

13. A purified polypeptide composition comprising at least 50 weight % of a protein consisting of the amino acid sequence as set forth in SEQ ID NO:10.

14. A purified polypeptide composition comprising at least 50 weight % of a protein consisting of the amino acid sequence as set forth in SEQ ID NO:8.

* * * * *

SEQUENCE LISTING (1) GENERAL INFORMATION:

(iii) NUMBER OF SEQUENCES: 67

(2) INFORMATION FOR SEQ ID NO:1:

(i) SEQUENCE CHARACTERISTICS:
       (A) LENGTH: 2119 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:1:

```
ATCAGCCCAA GATGGAGGCA GGCTAGTTTA TCACTACCTG TATCTTATCT GCTAGCCAAT      60
GGTACTAAAA CCTATGGCTC AGTGTCCCTC TTCCCAACCA GGAAATGTGG AAGACAGTGG     120
GAAAGGAAGG ACCGTGCTCG TGGAAAACAG CCTCTGACCC CAGACACAAC TGTATGGAAA     180
GTCCAGGGCT GTGTGACAGT TCCTGTGACA GGAAAACACC TCCCCGTGTG GCACCAGGCA     240
GTGAGATGTC CCTAGACATT TTCATTGGCA CCGAGGAAGG CATGTTCTTT GGTATGCTTA     300
GCCGAGACCA ACACCTGGAA TGATACCAGG TGGCTGCCTC TGACCCCAAC ACTGTGCTTG     360
GAAAGAATGT AGCCTGTGAC TTCTAGTAAA AGTGTCCTAG ATGATGAGGG CAGCAACCTG     420
AGGCAGCAGA AGCTCGACCG GCAGCGGGCC CTGTTGGAAC AGAAGCAGAA GAAGAAGCGC     480
CAAGAGCCCT TGATGGTACA GGCCAATGCA GATGGACGGC CCCGGAGTCG GCGAGCCCGG     540
CAGTCAGAGG AGCAAGCCCC CCTGGTGGAG TCCTACCTCA GCAGCAGTGG CAGCACCAGC     600
TACCAAGTTC AAGAGGCCGA CTCGATTGCC AGTGTACAGC TGGGAGCCAC CCGCCCACCA     660
GCACCAGCCT CAGCCAAGAA ATCCAAGGGA GCGGCTGCAT CTGGGGGCCA GGGTGGAGCC     720
CCTAGGAAGG AGAAGAAGGG AAAGCATAAA GGCACCAGCG GCCAGCAAC TCTGGCAGAA     780
GACAAGTCTG AGGCCCAAGG CCCAGTGCAG ATCTTGACTG TGGGACAGTC AGACCACGAC     840
AAGGATGCGG GAGAGACAGC AGCCGGCGGG GGCGCACAGC CCAGTGGGCA GGACCTCCGT     900
GCCACGATGC AGAGGAAGGG CATCTCCAGC AGCATGAGCT TTGACGAGGA CGAGGATGAG     960
GATGAAAACA GCTCCAGCTC CTCCCAGCTA ACAGCAACA CCCGCCCTAG TTCTGCCACT    1020
AGCAGAAAGT CCATCCGGGA GGCAGCTTCA GCCCCCAGCC CAGCCGCCCC AGAGCCACCA    1080
GTGGATATTG AGGTCCAGGA TCTAGAGGAG TTTGCACTGA GGCCAGCCCC ACAAGGGATC    1140
ACCATCAAAT GCCGCATCAC TCGGGACAAG AAGGGGATGG ACCGCGGCAT GTACCCCACC    1200
TACTTTCTGC ACCTAGACCG TGAGGATGGC AAGAAGGTGT TCCTCCTGGC GGGCAGGAAG    1260
AGAAAGAAGA GTAAAACTTC CAATTACCTC ATCTCTGTGG ACCCAACAGA CTTGTCTCGG    1320
GGAGGCGATA GCTATATCGG GAAGTTGCGG TCCAACCTGA TGGGCACCAA GTTCACCGTT    1380
TATGACAATG GCGTCAACCC TCAGAAGGCA TCCTCTTCCA CGCTGGAAAG CGGAACCTTG    1440
CGCCAGGAGC TGGCAGCGGT GTGCTATGAG ACAAATGTCC TAGGCTTCAA GGGACCTCGG    1500
AAGATGAGTG TGATCGTCCC AGGCATGAAC ATGGTTCATG AGAGAGTCTG TATCCGCCCC    1560
CGCAATGAAC ATGAGACCCT GTTAGCACGC TGGCAGAACA AGAACACGGA GAGCATCATT    1620
GAGCTGCAGA ACAAGACGCC AGTCTGGAAT GATGACACAC AGTCCTATGT ACTTAACTTC    1680
CACGGCCGTG TCACACAGGC TTCTGTGAAG AACTTCCAGA TCATCCACGG CAATGACCCG    1740
GACTACATCG TCATGCAGTT TGGCCGGGTA GCAGAAGATG TGTTCACCAT GGATTACAAC    1800
```

```
TACCCACTGT GTGCACTGCA GGCCTTTGCC ATTGCTCTGT CCAGCTTTGA CAGCAAGCTG      1860

GCCTGCGAGT AGAGGCCCCC ACTGCCTTTA GGTGGCCCAG TCCGGAGTGG AGCTTGCCTG      1920

CCTGCCAAGA CAGCCCTGCC TACCCTCTGT TCATAGGCCC TCTATGGGCT TTCTGGCCTT      1980

ACCAACCAGA GACTGGCTGC TCTGCCTCTG CTGCTGAAGC AGGGGGGACA GCAAATGGGT      2040

ATGACAGGAG AAGAATATTT CTGTGCCCCA AGGTCAACAA CACACATGCC CAGTCCTGGA      2100

AAAAAAAAAA AAAAAAAA                                                    2119

(2) INFORMATION FOR SEQ ID NO:2:

(i) SEQUENCE CHARACTERISTICS:
        (A) LENGTH: 459 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Val Gln Ala Asn Ala Asp Gly Arg Pro Arg Ser Arg Arg Ala Arg
 1               5                  10                  15

Gln Ser Glu Glu Gln Ala Pro Leu Val Glu Ser Tyr Leu Ser Ser Ser
            20                  25                  30

Gly Ser Thr Ser Tyr Gln Val Gln Glu Ala Asp Ser Ile Ala Ser Val
        35                  40                  45

Gln Leu Gly Ala Thr Arg Pro Pro Ala Pro Ala Ser Ala Lys Lys Ser
    50                  55                  60

Lys Gly Ala Ala Ala Ser Gly Gly Gln Gly Gly Ala Pro Arg Lys Glu
65                  70                  75                  80

Lys Lys Gly Lys His Lys Gly Thr Ser Gly Pro Ala Thr Leu Ala Glu
                85                  90                  95

Asp Lys Ser Glu Ala Gln Gly Pro Val Gln Ile Leu Thr Val Gly Gln
            100                 105                 110

Ser Asp His Asp Lys Asp Ala Gly Glu Thr Ala Ala Gly Gly Gly Ala
        115                 120                 125

Gln Pro Ser Gly Gln Asp Leu Arg Ala Thr Met Gln Arg Lys Gly Ile
    130                 135                 140

Ser Ser Ser Met Ser Phe Asp Glu Asp Glu Asp Glu Asp Glu Asn Ser
145                 150                 155                 160

Ser Ser Ser Ser Gln Leu Asn Ser Asn Thr Arg Pro Ser Ser Ala Thr
                165                 170                 175

Ser Arg Lys Ser Ile Arg Glu Ala Ala Ser Ala Pro Ser Pro Ala Ala
            180                 185                 190

Pro Glu Pro Pro Val Asp Ile Glu Val Gln Asp Leu Glu Glu Phe Ala
        195                 200                 205

Leu Arg Pro Ala Pro Gln Gly Ile Thr Ile Lys Cys Arg Ile Thr Arg
    210                 215                 220

Asp Lys Lys Gly Met Asp Arg Gly Met Tyr Pro Thr Tyr Phe Leu His
225                 230                 235                 240

Leu Asp Arg Glu Asp Gly Lys Lys Val Phe Leu Leu Ala Gly Arg Lys
                245                 250                 255

Arg Lys Lys Ser Lys Thr Ser Asn Tyr Leu Ile Ser Val Asp Pro Thr
            260                 265                 270

Asp Leu Ser Arg Gly Gly Asp Ser Tyr Ile Gly Lys Leu Arg Ser Asn
        275                 280                 285
```

```
Leu Met Gly Thr Lys Phe Thr Val Tyr Asp Asn Gly Val Asn Pro Gln
    290                 295                 300

Lys Ala Ser Ser Ser Thr Leu Glu Ser Gly Thr Leu Arg Gln Glu Leu
305                 310                 315                 320

Ala Ala Val Cys Tyr Glu Thr Asn Val Leu Gly Phe Lys Gly Pro Arg
                325                 330                 335

Lys Met Ser Val Ile Val Pro Gly Met Asn Met Val His Glu Arg Val
                340                 345                 350

Cys Ile Arg Pro Arg Asn Glu His Glu Thr Leu Leu Ala Arg Trp Gln
            355                 360                 365

Asn Lys Asn Thr Glu Ser Ile Ile Glu Leu Gln Asn Lys Thr Pro Val
370                 375                 380

Trp Asn Asp Asp Thr Gln Ser Tyr Val Leu Asn Phe His Gly Arg Val
385                 390                 395                 400

Thr Gln Ala Ser Val Lys Asn Phe Gln Ile Ile His Gly Asn Asp Pro
                405                 410                 415

Asp Tyr Ile Val Met Gln Phe Gly Arg Val Ala Glu Asp Val Phe Thr
                420                 425                 430

Met Asp Tyr Asn Tyr Pro Leu Cys Ala Leu Gln Ala Phe Ala Ile Ala
            435                 440                 445

Leu Ser Ser Phe Asp Ser Lys Leu Ala Cys Glu
450                 455

(2) INFORMATION FOR SEQ ID NO:3:

(i) SEQUENCE CHARACTERISTICS:
        (A) LENGTH: 2434 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

CCTCTCCCGA GCGCTGCACC GCGCACAGAC AACCGTTCTG GGAGCCCGCG GCCGGGGCCC         60

TGGCGTGCAG AGAGGGCCTC GGCGGGGCCC AGCGGTCGGG CCGGGGAGGA TGCGGCCCGG        120

GGCGGCCCGA GAGTTGAGCA GGGTCCCCGC GCCAGCCCCG AGCGGTCCCG GCCACCGGAG        180

CCGCAGCCGC CGCCCCGCCC CCGGGAGACA TGACTTCCAA GCCGCATTCC GACTGGATTC        240

CTTACAGTGT CCTAGATGAT GAGGGCAGCA ACCTGAGGCA GCAGAAGCTC GACCGGCAGC        300

GGGCCCTGTT GGAACAGAAG CAGAAGAAGA AGCGCCAAGA GCCCTTGATG GTACAGGCCA        360

ATGCAGATGG ACGGCCCCGG AGTCGGCGAG CCCGGCAGTC AGAGGAGCAA GCCCCCCTGG        420

TGGAGTCCTA CCTCAGCAGC AGTGGCAGCA CCAGCTACCA AGTTCAAGAG GCCGACTCGA        480

TTGCCAGTGT ACAGCTGGGA GCCACCCGCC ACCAGCACC AGCCTCAGCC AAGAAATCCA        540

AGGGAGCGGC TGCATCTGGG GGCCAGGGTG GAGCCCCTAG GAAGGAGAAG AAGGGAAAGC        600

ATAAAGGCAC CAGCGGGCCA GCAACTCTGG CAGAAGACAA GTCTGAGGCC CAAGGCCCAG        660

TGCAGATCTT GACTGTGGGA CAGTCAGACC ACGACAAGGA TGCGGGAGAG ACAGCAGCCG        720

GCGGGGCGC ACAGCCCAGT GGGCAGGACC TCCGTGCCAC GATGCAGAGG AAGGGCATCT        780

CCAGCAGCAT GAGCTTTGAC GAGGACGAGG ATGAGGATGA AAACAGCTCC AGCTCCTCCC        840

AGCTAAACAG CAACACCCGC CCTAGTTCTG CCACTAGCAG AAAGTCCATC CGGGAGGCAG        900

CTTCAGCCCC CAGCCCAGCC GCCCCAGAGC CACCAGTGGA TATTGAGGTC CAGGATCTAG        960
```

```
AGGAGTTTGC ACTGAGGCCA GCCCCACAAG GGATCACCAT CAAATGCCGC ATCACTCGGG    1020

ACAAGAAGGG GATGGACCGC GGCATGTACC CCACCTACTT TCTGCACCTA GACCGTGAGG    1080

ATGGCAAGAA GGTGTTCCTC CTGGCGGGCA GGAAGAGAAA GAAGAGTAAA ACTTCCAATT    1140

ACCTCATCTC TGTGGACCCA ACAGACTTGT CTCGGGGAGG CGATAGCTAT ATCGGGAAAT    1200

TGCGGTCCAA CCTGATGGGC ACCAAGTTCA CCGTTTATGA CAATGGCGTC AACCCTCAGA    1260

AGGCATCCTC TTCCACGCTG GAAAGCGGAA CCTTGCGCCA GGAGCTGGCA GCGGTGTGCT    1320

ATGAGACAAA TGTCCTAGGC TTCAAGGGAC CTCGGAAGAT GAGTGTGATC GTCCCAGGCA    1380

TGAACATGGT TCATGAGAGA GTCTGTATCC GCCCCCGCAA TGAACATGAG ACCCTGTTAG    1440

CACGCTGGCA GAACAAGAAC ACGGAGAGCA TCATTGAGCT GCAGAACAAG ACGCCAGTCT    1500

GGAATGATGA CACACAGTCC TATGTACTTA ACTTCCACGG CCGTGTCACA CAGGCTTCTG    1560

TGAAGAACTT CCAGATCATC CACGGCAATG ACCCGGACTA CATCGTCATG CAGTTTGGCC    1620

GGGTAGCAGA AGATGTGTTC ACCATGGATT ACAACTACCC ACTGTGTGCA CTGCAGGCCT    1680

TTGCCATTGC TCTGTCCAGC TTTGACAGCA AGCTGGCCTG CGAGTAGAGG CCCCCACTGC    1740

CTTTAGGTGG CCCAGTCCGG AGTGGAGCTT GCCTGCCTGC CAAGACAGCC CTGCCTACCC    1800

TCTGTTCATA GGCCCTCTAT GGGCTTTCTG GCCTTACCAA CCAGAGACTG GCTGCTCTGC    1860

CTCTGCTGCT GAAGCAGGGG GGACAGCAAA TGGGTATGAC AGGAGAAGAA TATTTCTGTG    1920

CCCCAAGGTC AACACACATG CCCAGTCCTG GGTCAGTCCC CTGCTGCAGT GGTGTTATCA    1980

CACCGGAAAG CCTCTTCACC TGGAGGTACA GAGGGAGAGG AAGCACAAGC CTGGCTGCTG    2040

TGGYTCAGCC ATCCACTCAG CCTACGAGTC AGAGACAGTG GGTGTCCCKG GAAGCRGGGG    2100

TACAGTGAGT GTGTGTGTAT GTACAGGGCA CTCAAGCTGT ATGTAGAAAA AGCTCTGGTG    2160

GTCAGCAGAA AGCACTCCCR CTTCAAAAGG GCCCATTAGG CCCAAAGGGG GTTAGGAGTG    2220

GTAGGGATAG GTGCGTGGCA GGTCCCTGCT AGGATTGCAG GGGCCTGGCC ATGTGTATTA    2280

GCTGGAGGCT TAGAATGCTA GCTCATTTGT TGCTACAGAT TTGCCCAGTG CTTGCAYACG    2340

TAAGAACCCA GCTCTCAAGG CCAAATATCT GAKTGGATGG GGATGATAGG AGTCATCCAG    2400

TAGACTCCCT ACATCAGGGC TCTCAGCAGC CCCA                                2434

(2) INFORMATION FOR SEQ ID NO:4:

(i) SEQUENCE CHARACTERISTICS:
        (A) LENGTH: 505 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Thr Ser Lys Pro His Ser Asp Trp Ile Pro Tyr Ser Val Leu Asp
  1               5                  10                  15

Asp Glu Gly Ser Asn Leu Arg Gln Gln Lys Leu Asp Arg Gln Arg Ala
             20                  25                  30

Leu Leu Glu Gln Lys Gln Lys Lys Arg Gln Glu Pro Leu Met Val
         35                  40                  45

Gln Ala Asn Ala Asp Gly Arg Pro Arg Ser Arg Ala Arg Gln Ser
     50                  55                  60

Glu Glu Gln Ala Pro Leu Val Glu Ser Tyr Leu Ser Ser Ser Gly Ser
 65                  70                  75                  80

Thr Ser Tyr Gln Val Gln Glu Ala Asp Ser Ile Ala Ser Val Gln Leu
```

-continued

```
                85                  90                  95
Gly Ala Thr Arg Pro Ala Pro Ala Ser Ala Lys Lys Ser Lys Gly
                100                 105                 110
Ala Ala Ala Ser Gly Gly Gln Gly Gly Ala Pro Arg Lys Glu Lys Lys
                115                 120                 125
Gly Lys His Lys Gly Thr Ser Gly Pro Ala Thr Leu Ala Glu Asp Lys
                130                 135                 140
Ser Glu Ala Gln Gly Pro Val Gln Ile Leu Thr Val Gly Gln Ser Asp
145                 150                 155                 160
His Asp Lys Asp Ala Gly Glu Thr Ala Ala Gly Gly Ala Gln Pro
                165                 170                 175
Ser Gly Gln Asp Leu Arg Ala Thr Met Gln Arg Lys Gly Ile Ser Ser
                180                 185                 190
Ser Met Ser Phe Asp Glu Asp Glu Asp Glu Asn Ser Ser Ser
                195                 200                 205
Ser Ser Gln Leu Asn Ser Asn Thr Arg Pro Ser Ser Ala Thr Ser Arg
                210                 215                 220
Lys Ser Ile Arg Glu Ala Ala Ser Ala Pro Ser Pro Ala Ala Pro Glu
225                 230                 235                 240
Pro Pro Val Asp Ile Glu Val Gln Asp Leu Glu Glu Phe Ala Leu Arg
                245                 250                 255
Pro Ala Pro Gln Gly Ile Thr Ile Lys Cys Arg Ile Thr Arg Asp Lys
                260                 265                 270
Lys Gly Met Asp Arg Gly Met Tyr Pro Thr Tyr Phe Leu His Leu Asp
                275                 280                 285
Arg Glu Asp Gly Lys Lys Val Phe Leu Leu Ala Gly Arg Lys Arg Lys
                290                 295                 300
Lys Ser Lys Thr Ser Asn Tyr Leu Ile Ser Val Asp Pro Thr Asp Leu
305                 310                 315                 320
Ser Arg Gly Gly Asp Ser Tyr Ile Gly Lys Leu Arg Ser Asn Leu Met
                325                 330                 335
Gly Thr Lys Phe Thr Val Tyr Asp Asn Gly Val Asn Pro Gln Lys Ala
                340                 345                 350
Ser Ser Ser Thr Leu Glu Ser Gly Thr Leu Arg Gln Glu Leu Ala Ala
                355                 360                 365
Val Cys Tyr Glu Thr Asn Val Leu Gly Phe Lys Gly Pro Arg Lys Met
                370                 375                 380
Ser Val Ile Val Pro Gly Met Asn Met Val His Glu Arg Val Cys Ile
385                 390                 395                 400
Arg Pro Arg Asn Glu His Glu Thr Leu Leu Ala Arg Trp Gln Asn Lys
                405                 410                 415
Asn Thr Glu Ser Ile Ile Glu Leu Gln Asn Lys Thr Pro Val Trp Asn
                420                 425                 430
Asp Asp Thr Gln Ser Tyr Val Leu Asn Phe His Gly Arg Val Thr Gln
                435                 440                 445
Ala Ser Val Lys Asn Phe Gln Ile Ile His Gly Asn Asp Pro Asp Tyr
                450                 455                 460
Ile Val Met Gln Phe Gly Arg Val Ala Glu Asp Val Phe Thr Met Asp
465                 470                 475                 480
Tyr Asn Tyr Pro Leu Cys Ala Leu Gln Ala Phe Ala Ile Ala Leu Ser
                485                 490                 495
Ser Phe Asp Ser Lys Leu Ala Cys Glu
                500                 505
```

(2) INFORMATION FOR SEQ ID NO:5:

(i) SEQUENCE CHARACTERISTICS:
        (A) LENGTH: 480 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
ACTTCCAGAT CATCCACGGC AATGACCTTG AGTGTTGCCA CTCCCTGTTT TTGATGTTGT      60

ACGCATGGTG CCCAGCCCCC ACCCCACCCC CAATCCCCTG ATCTGGTCCA TATCAGCCAG     120

TGATGGGATG TGGGTATATG GCTTTTGTTA GAACTTTCTA ACTGTAGTGA TCTAGAGTCC     180

TGCCCCTAGT GCCCTGCATG TCTGGGGCTT GGGAATACCC TTTAAATGGA TGTCTTTTCT     240

CTCCTGGGCC CTGCTGTCTG TGTGCATCTC CCCCCTTCAC CCTCTTGCTT CATAATGTTT     300

CTCTTGAACC TTTGTTTTGT TCATCCTTTC GATCTCTTTG GCATTTCTGC TTTCTCCTTC     360

CCTCTTGTGG CCCATGTCTT ACCTGGTCTC CCTGTCTCCA CCAATTCTTG CTTGGTGCAT     420

GCCACAGCGG ACTACATCGT CATGCAGTTT GGCCGGGTAG CAGAAGATGT GTTCACCATG     480
```

(2) INFORMATION FOR SEQ ID NO:6:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Asn Phe Gln Ile Ile His Gly Asn Asp Leu Glu Cys Cys His Ser Leu
 1               5                  10                  15

Phe Leu Met Leu Tyr Ala Trp Cys Pro Ala Pro Thr Pro Pro Ile
            20                  25                  30

Pro
```

(2) INFORMATION FOR SEQ ID NO:7:

(i) SEQUENCE CHARACTERISTICS:
        (A) LENGTH: 1426 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

```
CAGAAGAAGA AGCGCCAGGA GCCCCTGATG GTGCAGGCCA ATGCAGATGG GCGGCCCCGG      60

AGCCGGCGGG CCCGGCAGTC AGAGGAACAA GCCCCCCTGG TGGAGTCCTA CCTCAGCAGC     120

AGTGGCAGCA CCAGCTACCA AGTTCAAGAG GCCGACTCAC TCGCCAGTGT GCAGCTGGGA     180

GCCACGCGCC AACAGCACCC AGCTTCAGCC AAGAGAACCA AGGCGGCAGC TACAGCAGGG     240

GGCCAGGGCG GCGCCGCTAG GAAGGAGAAG AAGGGAAAGC ACAAAGGCAC CAGCGGGCCA     300

GCAGCACTGG CAGAAGACAA GTCTGAGGCC CAAGGCCCAG TGCAGATTCT GACTGTGGGC     360

CAGTCAGACC ACGCCCAGGA CGCAGGGGAG ACGGCAGCTG GTGGGGGCGA ACGGCCCAGC     420

GGGCAGGATC TCCGTGCCAC GATGCAGAGG AAGGGCATCT CCAGCAGCAT GAGCTTTGAC     480
```

```
GAGGATGAGG AGGATGAGGA GGAGAATAGC TCCAGCTCCT CCCAGCTAAA TAGTAACACC      540

CGCCCCAGCT CTGCTACTAG CAGGAAGTCC GTCAGGGAGG CAGCCTCAGC CCCTAGCCCA      600

ACAGCTCCAG AGCAACCAGT GGACGTTGAG GTCCAGGATC TTGAGGAGTT TGCACTGAGG      660

CCGGCCCCCC AGGGTATCAC CATCAAATGC CGCATCACTC GGGACAAGAA AGGGATGGAC      720

CGGGGCATGT ACCCCACCTA CTTTCTGCAC CTGGACCGTG AGGATGGGAA GAAGGTGTTC      780

CTCCTGGCGG GAAGGAAGAG AAAGAAGAGT AAAACTTCCA ATTACCTCAT CTCTGTGGAC      840

CCAACAGACT TGTCTCGAGG AGGGGACAGC TATATCGGGA ACTGCGGTC CAACTTGATG       900

GGCACCAAGT TCACTGTTTA TGACAATGGA GTCAACCCTC AGAAGGCCTC ATCCTCCACT      960

TTGGAAAGTG GAACCTTACG TCAGGAGCTG GCAGCTGTGT GCTACGAGAC AAACGTCTTA     1020

GGCTTCAAGG GGCCTCGGAA GATGAGCGTG ATTGTCCCAG GCATGAACAT GGTCCATGAG     1080

AGAGTCTCTA TCCGCCCCCG CAACGAGCAT GAGACACTGC TAGCACGCTG GCAGAATAAG     1140

AACACGGAGA GTATCATCGA GCTGCAAAAC AAGACACCTG TCTGGAATGA TGACACACAG     1200

TCCTATGTAC TCAACTTCCA TGGGCGCGTC ACACAGGCCT CCGTGAAGAA CTTCCAGATC     1260

ATCCATGGCA ATGACCCGGA CTACATCGTG ATGCAGTTTG GCCGGGTAGC AGAGGATGTG     1320

TTCACCATGG ATTACAACTA CCCGCTGTGT GCACTGCAGG CCTTTGCCAT TGCCCTGTCC     1380

AGCTTCGACA GCAAGCTGGC GTGCGAGTAG AGGCCTCTTC GTGCCC                    1426

(2) INFORMATION FOR SEQ ID NO:8:

(i) SEQUENCE CHARACTERISTICS:
        (A) LENGTH: 460 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Met Val Gln Ala Asn Ala Asp Gly Arg Pro Arg Ser Arg Arg Ala Arg
  1               5                  10                  15

Gln Ser Glu Glu Gln Ala Pro Leu Val Glu Ser Tyr Leu Ser Ser Ser
             20                  25                  30

Gly Ser Thr Ser Tyr Gln Val Gln Glu Ala Asp Ser Leu Ala Ser Val
         35                  40                  45

Gln Leu Gly Ala Thr Arg Pro Thr Ala Pro Ala Ser Ala Lys Arg Thr
 50                  55                  60

Lys Ala Ala Thr Ala Gly Gly Gln Gly Gly Ala Ala Arg Lys Glu
 65                  70                  75                  80

Lys Lys Gly Lys His Lys Gly Thr Ser Gly Pro Ala Ala Leu Ala Glu
             85                  90                  95

Asp Lys Ser Glu Ala Gln Gly Pro Val Gln Ile Leu Thr Val Gly Gln
            100                 105                 110

Ser Asp His Ala Gln Asp Ala Gly Glu Thr Ala Ala Gly Gly Gly Glu
        115                 120                 125

Arg Pro Ser Gly Gln Asp Leu Arg Ala Thr Met Gln Arg Lys Gly Ile
    130                 135                 140

Ser Ser Ser Met Ser Phe Asp Glu Asp Glu Asp Glu Glu Asn
145                 150                 155                 160

Ser Ser Ser Ser Gln Leu Asn Ser Asn Thr Arg Pro Ser Ser Ala
                165                 170                 175
```

```
Thr Ser Arg Lys Ser Val Arg Glu Ala Ala Ser Ala Pro Ser Pro Thr
            180                 185                 190

Ala Pro Glu Gln Pro Val Asp Val Glu Val Gln Asp Leu Glu Glu Phe
            195                 200                 205

Ala Leu Arg Pro Ala Pro Gln Gly Ile Thr Ile Lys Cys Arg Ile Thr
            210                 215                 220

Arg Asp Lys Lys Gly Met Asp Arg Gly Met Tyr Pro Thr Tyr Phe Leu
225                 230                 235                 240

His Leu Asp Arg Glu Asp Gly Lys Lys Val Phe Leu Leu Ala Gly Arg
            245                 250                 255

Lys Arg Lys Lys Ser Lys Thr Ser Asn Tyr Leu Ile Ser Val Asp Pro
            260                 265                 270

Thr Asp Leu Ser Arg Gly Gly Asp Ser Tyr Ile Gly Lys Leu Arg Ser
            275                 280                 285

Asn Leu Met Gly Thr Lys Phe Thr Val Tyr Asp Asn Gly Val Asn Pro
            290                 295                 300

Gln Lys Ala Ser Ser Thr Leu Glu Ser Gly Thr Leu Arg Gln Glu
305                 310                 315                 320

Leu Ala Ala Val Cys Tyr Glu Thr Asn Val Leu Gly Phe Lys Gly Pro
            325                 330                 335

Arg Lys Met Ser Val Ile Val Pro Gly Met Asn Met Val His Glu Arg
            340                 345                 350

Val Ser Ile Arg Pro Arg Asn Glu His Glu Thr Leu Leu Ala Arg Trp
            355                 360                 365

Gln Asn Lys Asn Thr Glu Ser Ile Ile Glu Leu Gln Asn Lys Thr Pro
            370                 375                 380

Val Trp Asn Asp Asp Thr Gln Ser Tyr Val Leu Asn Phe His Gly Arg
385                 390                 395                 400

Val Thr Gln Ala Ser Val Lys Asn Phe Gln Ile Ile His Gly Asn Asp
            405                 410                 415

Pro Asp Tyr Ile Val Met Gln Phe Gly Arg Val Ala Glu Asp Val Phe
            420                 425                 430

Thr Met Asp Tyr Asn Tyr Pro Leu Cys Ala Leu Gln Ala Phe Ala Ile
            435                 440                 445

Ala Leu Ser Ser Phe Asp Ser Lys Leu Ala Cys Glu
            450                 455                 460

(2) INFORMATION FOR SEQ ID NO:9:

(i) SEQUENCE CHARACTERISTICS:
        (A) LENGTH: 3268 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

CTTGAGGATT CAGTCTGGTC CTGAAGGGTT TGGGGGGAGA CTGCGACCAG AAGATGTTTC     60

CATGTCCTAA TTAATGGGTG ATGGTGGTTG TTAGTCTGAC TGTTGCCACG GTGATGAAGG    120

GAGACATCCA AGTGCTGGTT TCAGTACTGA GGCGAATACA GGGAATTTCA ACAGGCTCCA    180

GGTCTTACTA TGCAGCCTGA AGTGGGACCA TCCCTTAAAC CCACTCCATC CTGTGGCCAC    240

GATGGGGGCC AGGACACCTT TGCCTTCTTT CTGGGTTTCT TCTTTGCCG AGACAGGGAT     300

TTTGTTCCCA GGAGGCACTC CCTGGCCCAT GGATCTCAG CATTCAAAGC AGCACAGGAA     360
```

-continued

```
ACCTGGGCCC CTGAAACGGG GCCACCGAAG AGATCGGAGA ACAACCAGGA GGAAGTACTG      420

GAAGGAAGGA AGGGAGATCG CTCGTGTCTT AGATGATGAG GGCAGAAACC TGAGGCAGCA      480

GAAGCTTGAT CGGCAGCGGG CCCTGCTGGA GCAGAAGCAG AAGAAGAAGC GCCAGGAGCC      540

CCTGATGGTG CAGGCCAATG CAGATGGGCG GCCCCGGAGC CGGCGGGCCC GGCAGTCAGA      600

GGAACAAGCC CCCCTGGTGG AGTCCTACCT CAGCAGCAGT GGCAGCACCA GCTACCAAGT      660

TCAAGAGGCC GACTCACTCG CCAGTGTGCA GCTGGGAGCC ACGCGCCCAA CAGCACCAGC      720

TTCAGCCAAG AGAACCAAGG CGGCAGCTAC AGCAGGGGC CAGGGCGGCG CCGCTAGGAA       780

GGAGAAGAAG GGAAAGCACA AAGGCACCAG CGGGCCAGCA GCACTGGCAG AAGACAAGTC      840

TGAGGCCCAA GGCCCAGTGC AGATTCTGAC TGTGGGCCAG TCAGACCACG CCCAGGACGC      900

AGGGGAGACG GCAGCTGGTG GGGGCGAACG GCCCAGCGGG CAGGATCTCC GTGCCACGAT      960

GCAGAGGAAG GGCATCTCCA GCAGCATGAG CTTTGACGAG GATGAGGAGG ATGAGGAGGA     1020

GAATAGCTCC AGCTCCTCCC AGCTAAATAG TAACACCCGC CCCAGCTCTG CTACTAGCAG     1080

GAAGTCCGTC AGGGAGGCAG CCTCAGCCCC TAGCCCAACA GCTCCAGAGC AACCAGTGGA     1140

CGTTGAGGTC CAGGATCTTG AGGAGTTTGC ACTGAGGCCG GCCCCCCAGG GTATCACCAT     1200

CAAATGCCGC ATCACTCGGG ACAAGAAAGG GATGGACCGG GGCATGTACC CCACCTACTT     1260

TCTGCACCTG GACCGTGAGG ATGGGAAGAA GGTGTTCCTC CTGGCGGGAA GGAAGAGAAA     1320

GAAGAGTAAA ACTTCCAATT ACCTCATCTC TGTGGACCCA ACAGACTTGT CTCGAGGAGG     1380

GGACAGCTAT ATCGGGAAAC TGCGGTCCAA CTTGATGGGC ACCAAGTTCA CTGTTTATGA     1440

CAATGGAGTC AACCCTCAGA AGGCCTCATC CTCCACTTTG GAAAGTGGAA CCTTACGTCA     1500

GGAGCTGGCA GCTGTGTGCT ACGAGACAAA CGTCTTAGGC TTCAAGGGGC CTCGGAAGAT     1560

GAGCGTGATT GTCCCAGGCA TGAACATGGT CCATGAGAGA GTCTCTATCC GCCCCGCAA     1620

CGAGCATGAG ACACTGCTAG CACGCTGGCA GAATAAGAAC ACGGAGAGTA TCATCGAGCT     1680

GCAAAACAAG ACACCTGTCT GGAATGATGA CACACAGTCC TATGTACTCA ACTTCCATGG     1740

GCGCGTCACA CAGGCCTCCG TGAAGAACTT CCAGATCATC CATGGCAATG ACCCGGACTA     1800

CATCGTGATG CAGTTTGGCC GGGTAGCAGA GGATGTGTTC ACCATGGATT ACAACTACCC     1860

GCTGTGTGCA CTGCAGGCCT TTGCCATTGC CCTGTCCAGC TTCGCACGCA AGCTGGCGTG     1920

CGAGTAGAGG CCTCTTCGTG CCCTTTGGGG TTGCCCAGCC TGGAGCGGAG CTTGCCTGCC     1980

TGCCTGTGGA GACAGCCCTG CCTATCCTCT GTATATAGGC CTTCCGCCAG ATGAAGCTTT     2040

GGCCCTCAGT GGGCTCCCCT GGCCCAGCCA GCCAGGAACT GGCTCCTTTG CCTCTGCTAC     2100

TGAGCAGGGG AGTAGTGGAG AGCGGGTGGG TGGGTGTGAA GGGATGAGAA TAATTCTTTC     2160

CATGCCACGA GATCAACACA CACTCCCACC CTTGGGGTAG TAGTGTGTTG TAGTCGTACT     2220

TACCAAGCTG AGCAACCTCT TCAGCTGGGA AGGCCGCAAG AGGCATAGAG GGAGAGGAAG     2280

CACACTGCAG GGCTGCTGTG GCCCAGTCGT CCGCTCAGCC AAGGAGTCAG ATGGCAATGG     2340

GTACTCCAGC AGGTAGGGGC ACAGTGAATG TGTGTATGTA TGAAGGCCAC ATCAACTTTA     2400

TGTAGCAAAG GGCTTGGTGG CCAAGCCTGG CCCTTAAACA ACTGCAGAAA GCCCTTCAAC     2460

TTCAGAAGGC CTCACTCAAG CCTGAGAGAA GTTGGGAGGG TGGTGGGGAC AGGTAAGTGG     2520

CAGGACCCTG TCAGGATTGC AGGTGCCTGG CTTGCTGTGG CTATGGGAAT CAGCTGGTGG     2580

CTAGGTTTCT AGCGCATTTG ATTTCTCCAG GTTTGCTGTG TCTCACAGAG GCAGTAGGAA     2640

CCCAGCTCTC AGGGCTGTCT TGGTGGATGG GCCCTGCAAG ACACAGGCTC AGCATGCAGA     2700

AGTGCATGAA CAGGGTCCCT GGATCAGGGT TGTTCTGGGA GTCCTGTCAG CTTCCCCAGG     2760
```

```
AGCTCTCTGC TGAGCAGCCC AGCACAACCC CCAGGAAACA CAAATGGGGT CCAGGTCACC      2820

AGCCTGACTG CACACAGCTA GGCATGCCTG GGAATCCTGC TGCCAGAGAA CCATTCCCAA      2880

GCCATGGCAT GCTCCTTGAA GAATCTCTCC TCTCTCTCTC TCTCTGGAAA GACCCAACTT      2940

CCTCACTGCT GTCAGCCAAG TCATGGTTGG TAACCATGTA GGTTCTTGGG AGGGAATGGG      3000

ACAGGGTGAA TAAAGCAGGG AATATTTCCG GAATTCCACA AGAGATCAGC AGTGGCAGGA      3060

CCCTTAGGAA TCTAGTACAA CCTTGTTGCT TTAGGTGAGT CACACTCAGA AAATGGGGCT      3120

TGCCCTGGGT CACCTAGCTG GTTAATGGCA GCATTCAGTA ACTTCAAGTT CTCTTGATTT      3180

CTTTGTTCCC ACTGTCCCCC AAGAAACTAG TATCTCTGGC CTCCTGGGGC CCATTCTGCA      3240

TGCCCTCCCC ACTTCCCCCC CGGAATTC                                         3268
```

(2) INFORMATION FOR SEQ ID NO:10:

(i) SEQUENCE CHARACTERISTICS:
        (A) LENGTH: 561 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Gly Ala Arg Thr Pro Leu Pro Ser Phe Trp Val Ser Phe Phe Ala
 1               5                  10                  15

Glu Thr Gly Ile Leu Phe Pro Gly Gly Thr Pro Trp Pro Met Gly Ser
                20                  25                  30

Gln His Ser Lys Gln His Arg Lys Pro Gly Pro Leu Lys Arg Gly His
            35                  40                  45

Arg Arg Asp Arg Arg Thr Thr Arg Arg Lys Tyr Trp Lys Glu Gly Arg
        50                  55                  60

Glu Ile Ala Arg Val Leu Asp Asp Glu Gly Arg Asn Leu Arg Gln Gln
65                  70                  75                  80

Lys Leu Asp Arg Gln Arg Ala Leu Leu Glu Gln Lys Gln Lys Lys Lys
                85                  90                  95

Arg Gln Glu Pro Leu Met Val Gln Ala Asn Ala Asp Gly Arg Pro Arg
            100                 105                 110

Ser Arg Arg Ala Arg Gln Ser Glu Glu Gln Ala Pro Leu Val Glu Ser
        115                 120                 125

Tyr Leu Ser Ser Ser Gly Ser Thr Ser Tyr Gln Val Gln Glu Ala Asp
    130                 135                 140

Ser Leu Ala Ser Val Gln Leu Gly Ala Thr Arg Pro Thr Ala Pro Ala
145                 150                 155                 160

Ser Ala Lys Arg Thr Lys Ala Ala Thr Ala Gly Gly Gln Gly Gly
                165                 170                 175

Ala Ala Arg Lys Glu Lys Lys Gly Lys His Lys Gly Thr Ser Gly Pro
            180                 185                 190

Ala Ala Leu Ala Glu Asp Lys Ser Glu Ala Gln Gly Pro Val Gln Ile
        195                 200                 205

Leu Thr Val Gly Gln Ser Asp His Ala Gln Asp Ala Gly Glu Thr Ala
    210                 215                 220

Ala Gly Gly Glu Arg Pro Ser Gly Gln Asp Leu Arg Ala Thr Met
225                 230                 235                 240

Gln Arg Lys Gly Ile Ser Ser Ser Met Ser Phe Asp Glu Asp Glu Glu
                245                 250                 255
```

```
Asp Glu Glu Glu Asn Ser Ser Ser Ser Gln Leu Asn Ser Asn Thr
            260                 265                 270

Arg Pro Ser Ser Ala Thr Ser Arg Lys Ser Val Arg Glu Ala Ala Ser
            275                 280                 285

Ala Pro Ser Pro Thr Ala Pro Glu Gln Pro Val Asp Val Glu Val Gln
            290                 295                 300

Asp Leu Glu Glu Phe Ala Leu Arg Pro Ala Pro Gln Gly Ile Thr Ile
305                 310                 315                 320

Lys Cys Arg Ile Thr Arg Asp Lys Lys Gly Met Asp Arg Gly Met Tyr
                    325                 330                 335

Pro Thr Tyr Phe Leu His Leu Asp Arg Glu Asp Gly Lys Lys Val Phe
                    340                 345                 350

Leu Leu Ala Gly Arg Lys Arg Lys Ser Lys Thr Ser Asn Tyr Leu
            355                 360                 365

Ile Ser Val Asp Pro Thr Asp Leu Ser Arg Gly Gly Asp Ser Tyr Ile
            370                 375                 380

Gly Lys Leu Arg Ser Asn Leu Met Gly Thr Lys Phe Thr Val Tyr Asp
385                 390                 395                 400

Asn Gly Val Asn Pro Gln Lys Ala Ser Ser Thr Leu Glu Ser Gly
                    405                 410                 415

Thr Leu Arg Gln Glu Leu Ala Ala Val Cys Tyr Glu Thr Asn Val Leu
                    420                 425                 430

Gly Phe Lys Gly Pro Arg Lys Met Ser Val Ile Val Pro Gly Met Asn
            435                 440                 445

Met Val His Glu Arg Val Ser Ile Arg Pro Arg Asn Glu His Glu Thr
            450                 455                 460

Leu Leu Ala Arg Trp Gln Asn Lys Asn Thr Glu Ser Ile Ile Glu Leu
465                 470                 475                 480

Gln Asn Lys Thr Pro Val Trp Asn Asp Asp Thr Gln Ser Tyr Val Leu
                    485                 490                 495

Asn Phe His Gly Arg Val Thr Gln Ala Ser Val Lys Asn Phe Gln Ile
            500                 505                 510

Ile His Gly Asn Asp Pro Asp Tyr Ile Val Met Gln Phe Gly Arg Val
            515                 520                 525

Ala Glu Asp Val Phe Thr Met Asp Tyr Asn Tyr Pro Leu Cys Ala Leu
            530                 535                 540

Gln Ala Phe Ala Ile Ala Leu Ser Ser Phe Asp Ser Lys Leu Ala Cys
545                 550                 555                 560

Glu (2) INFORMATION FOR SEQ ID NO:11:

(i) SEQUENCE CHARACTERISTICS:
        (A) LENGTH: 5994 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:11:

CGATAGAGTG GTAGGGAGAC CCTGCCGAAC AGATAATTAG AGGGTGCCAA TATGATCTGG      60

GGGGAACCT  GGGAGACAGG GAGCTCCAGA GGCACCGCCC CTCGCCTGCC CGCTTCCCTG     120

TCGCTTCCAC ACCCTGGGGC CCATCGTGCC CCACTTCCTC CAAGCCCCAA GCCTTTGCAA     180
```

-continued

```
ACAGAACAAA AGCCGTTTCC TTGGTTCCCT TTTGTACGTC TGAGTTCAGG GGTCCGTTTC    240

AGGGCCTGGA CTCCGGGAGA CTCCGGGAAA CTCCGGCGCC CGAAGACAGA GCTGCATTCC    300

TGCTGTGCCG CCACAAGATG GCACTCTCTA GGTGTCCGCC CCAGTTTGAG CACTCCGGGA    360

GTTTCTGACA CTTGCTGGCC TTTCGCCCAG TTTCAGCCTG AAGATTGTGG TCAGACACAC    420

TCTGAATCCC ACCAGGCTTG ATTAGCTTTG CCTGCCCCCT GAGGCAGCTC ATGGACTTCT    480

TCAGACTCTG TAGTTCAGGA CATATTGACC CCTTCTGAAG GGGCCCTCAG GAACTGCCTG    540

CAGTGTAATT ACCTGCCTGC TTATACTCCT CCCCACCAGG CACTCCTGAG AGCGGGACCG    600

TCTTATTCTC CTCGGGGCCA CCTGCCCCAA CCCAGGGCCT GGCACGGCAG AGATGGCAGA    660

GGTGTTTGGT GGGGTGTAAT GTGTAAACAA CAGAGTGCTG CTGTCGTCAT TCATCCCACC    720

ATAGTTTGTC TGGTGAATGC ATTTTTAGTG TCAAGCTGCC TGAAGGAGAA GCCAGGGATA    780

AAGACCCAAG CTCAGAATGT ATCCTGGGGA GAGGGATTGG TTCACAGAGA GAAGCTGTCT    840

TGCAGCCTTT CCCCCTCTGG CCTGGTTCTG GCTGTTGCCA GCATTCTAGG AGTTCTCTAG    900

ACGGGCTGAA ACGCACCGCA GGGATACAGG GAGGGCCGGA GAATAGGCGT TTGTTTCCAG    960

GTAGAATTTT GGGGCATACC CGGCCTTGTC TGGGAGCAAT CAGGGACCAG AGGCAAGGGC   1020

TGCGATGGGC TCTGGGGCCT ACTGTGGCCT CATCCCTCTC ACCTGGCCCC AGCTCAGGCC   1080

ATTCCAAGAG CCTCCCAGCC TAACAGCAAC GTGTGGCTAT CCAAGGGTCC CAGACAGAGG   1140

ATTGGAGGGC TGCACCTGTG TTTAGGGGAC AGCCACCCCT CCCCCTAAGC ACCTGCTCTG   1200

ACAGCATGGG ATGATGTCAA CAAGGGACTT CCATGAAGCC CAAGGGGGAA GGACAGTGGG   1260

AGTGGGGTCT GAGGTCTGGA CTCTGCTTGA AGATTGACAA TGATGGGTGG GAGTCCCTCA   1320

CCCACTGTAA GCTCTAGGAA GAGGGTGAGC ATTCCTGTTG ATACTGTGGC CCATTGTGTT   1380

GGCAGAGTCC AGGCCAGTTT GTGCTCTTGG TGTGACCCCA GGAGGGAGTC CTTTGCTGGA   1440

TCATCTACCT CATGGGCTGG TACTGACATG CAGGTGCGAT TTCCCTGCCT AAAACAGGCT   1500

CCAGAGTAAG ACTGGCATCG CTCACCAGGG TAATTATTGG TTTGGGTTCA ATTTCCATTC   1560

AAAACAGTAA TCCCAGCCTG AGCTGGGTGT CAGATCTGAA GGTTGATTAT TAGTAACATT   1620

TATCAACAGC CTCTCTCAGC TTCAGGCAAT TACAGCTCAT CTGCCATTCC TGCTCCCAGT   1680

CATGCAAACT TGCCAGCTTC TTCCCTGCCC ACCCCCTCCA TTCCCCTCTC CCCTTCTTCT   1740

CCCATCTCCT CCCCTTAGCA GACAACTGAC GGAGGGCAGG AGGTGGGTGC CACCTTATGA   1800

CTCACTATCA CCCTGTATGG AGGGGTCCA TGTGCATGCT AGGCACCTGT GCTCCCCAGC   1860

AGCAATATTC ATGTTGCAGT CTTGTGAAAT CTGAATCTGA TTCTATCAGA ACTGAGGAGA   1920

ATCTGTGAAG GGGACAGATG GGAACCCATG TCTCCCGGCT CCTTGTCGCA TGATGCGTTT   1980

TCAATGGCAC TGTGCTCCTT CCTGCTCCTG ACTCAGTCTG TCCCTCCCCT CCAGGGCTGA   2040

GACTAGGGGA GGCTAGAAAG ACATTGACCT CAAGTGCAAC ATTCAAAGGA CCTCGAACAA   2100

GCTCAGTAAT TAAGATAAAT GATATTTCAA TATAGTATTT TTTTAAATCA AAATGAATGC   2160

AAAGCACCTA CAACAAAATC AAACCTTTAA TAAAGACAAG ATACAACACT GGATTTGCAG   2220

GCCTTGTATT GGCCTCACTT GCCTTACCCT AACTCCAGTC TTGTTTATCA TGGACAGTTT   2280

TGCTTTGATT TGCTGGAAGT ATTAAATTTC TTGGCTGCTG AGTTTTTTGG CAAATCTTTA   2340

AATTCTGCGC CTCAGGCGAG AGCTTTATTC AGCTTACCCT GGTGCTGGCC CCACTGCTCT   2400

CACTTCCCGC TGGGCCCTAA CCTCCTGCTC CCTTCAGCTC TTACTGCCTA CTGCCTCAGG   2460

CAGGGTGGCT CAGCTTCTCT CTTCGCAGGT GCCCAGGGCA GCAGGGACC CAAAGGGCCC    2520

CTCCATGGGC TGTCTTCCAG GGTGCCCATC CTTCATTCCA TCCCACTGGA CCCTGCTTCA   2580
```

```
GCCGTCAGAC ACCTCAGGGA GGGCCTGCAG GTTGCCAGAG TAACTGCTGT GATAACTGGA    2640

GGACAGAACA TGCTGGTCTT GCTCTGCTCG TAGAATCACG TCCAGCCAGG GCTGGATGAG    2700

TGCAAGCAGG CACGCCTGAC AGCGTCCCTG ACACGCTGAT CCAAAACGTC ACTGGACATG    2760

CATGGAGGTG GAGAACATTC CATGTACCCA CATTCCTCTA GGGGGACGAC AGCATGAGGC    2820

TGGAGGAAAA CTGTGGTGAT CTGTTTGTGA CAGGGAGGTG AGACGCTGAA GTAGACATGG    2880

ATGCTTCCTA ACCAGCCTTC CGCAGAGGGT AGGTCTCATT CGCTGAAGGG CTTCTGTTCT    2940

GCTGAGCAGG GTCTGTCAGT AGGGGGGCAC ACCTGTCTCC AGAGAATACC CTCCTCCTGT    3000

CCTCCCCTGG CTGTGCTCCA CTAGCCTAAA AGGTAAACAG ACATTTTAGA AGATCAGTG     3060

TTGAAGGGGT ACCCAAGATG CCAAATTATA TCTGGGACTT GAGACACTGT TATGTCGAGG    3120

TCCAGGCCTA GGCCAGCTGG TCACAGTGTC CAGATGCCTG TCACGGTGGG AGGCCTGAGG    3180

GTCTCAGGGG ACATGTATCA GAAGCACCTC TGCCCTGCCT GTTCCACTCT GTAATCTCCC    3240

TTCTGAGCCC CTACTGCAGC ACAGAGCCAG CTGGTCATCT AGCCTGGCAG TAGTAAGTCA    3300

TTCTATTTTC CTGCAGATAG GAATACATGG TTCCTGTTCC TCCTATGCAC TCTGCCACTT    3360

AAATTCCCCT CTCTGAGTCC TAGGTTCCCC TTTTGTGAAA TATCAATGAT AGCATCCTTC    3420

TTAGAAGGCT GTGCTCACCA TTCAGTGCAC TAATGCAAAG CACTGTGACC GACTGAAGAG    3480

TCATGTTCTG TGGGGCCATG GAGGACAGAA CTAGGACTGA AGGGAGGTGT GTTTGAGCTT    3540

TAGGTGAAGC AGCAATGGCC AACTACAAAG ATGGAGGGAC CGCTCTGGGA AGAGCAAACA    3600

CCCTGATGCT CAGAGTGTGC ATGAGGAGGT TTCATAATCA CCATCCAGCA GCTTAGCCTC    3660

AAAAGGGCTG CCTGCCCCAG GGAGCTATGA CCCTTGAGAG ATGCAGTTTA TCCAGCCCTG    3720

AGGTTCTGTT TGACCATCTT TCCCCGGTTG TCCTCCAGGG GGTCATGGCA CAAGTCTCAG    3780

TAGCACGGGC CCCATGGTCC AGCCTTAAGG TAAGAATGGA CCTCCCTGGA GGAAGCTGGC    3840

TTCATCTACA GTTGATAAGT TCACCTTTTT TCCTGGTCCA CTTTCCTTGG TTTAACCCTG    3900

TGACCAAACC TGAGAGCTTT GGCAGGAAGG AAACCAGGGA GGATGTTGTG CTTGAGAAAG    3960

TGCTGGCCTG AGCATTGGCT TTGAGATGTC CTTTTACTCT GACTGGAGGG TCTCATTCCA    4020

CCTGTAGCAA GACTAAAGAC ACCTGAAAGA GAGTTTCTGG GAGATGGAGG ATGAGGTCTC    4080

CAGTTGCAGG TGCATCACAC GTCCACTTCC CCACCTGGCA GGTGCCGGCA TGCAGGATGT    4140

CTGTGCGTGT GCCCCTTGCA CTGACTCCCT TGAGGCTGGC TGTGCAGCTT TGGGGCATGT    4200

GTCCAAGCAG AGAGAATGGA AGACTCCATA TTGGGAGCCT TGGCTTTGAC CTTTCCTTTC    4260

TCTGAGCCTG ATTTTCCCAA CAGTGTTATG GGAGGGAAG GATGAGATGC GCTTCTCAGC     4320

TGATGTCCGT GATTCTTCTG TTTTCTGGAG GCCATGAGTG TTAACAGAAT GTGTTCACTT    4380

TTGCACCCTT CTTCCATGAC CACTTACAGT CTGTCTGCTT AGCAGATGAG GGGTCTGGGT    4440

CTCCAGCGTC CATTTGGGGT GGGGTCAGCA ATGTCCAGCT TTGCATCTGG GTATCACTTT    4500

TCCTTCTGAT ACTTGAAATT GGATTCTGAA GATTCCTAAT TATTGTTCCA AGTTCTCATT    4560

GAAAATCTGG GTGTAATTTT TACAAGAGCA TGGCTGAGGA TGGACATGGA GGGGAAGTAG    4620

TGGGGCTGGA GGGAGGGAAG GGACAGACAG AAGGTGATGT TGTCATTAGG AGTTAAAGCC    4680

AGGGCCTGGT AGTAGATAAG GCTGGACAGT TGGCAGGATC ATCGGGCGGA CTAAAGTAGC    4740

TTAGATTCTG TCCAGAGGAA GTGGGGGTCT TCTGAAGGGT TTAAGTAGGC TGGGAGGACA    4800

TGATCTTAGG AAGCTCACTC TGGTGTCAGT TGCAGGATGG ATTTGAGAGG AGCAAGTTAG    4860

GTGTAGATGC CCATGATGAT GCCAAGATCT GGGCAACAGA CAGGAAGGCC CTAGCTCAGA    4920
```

```
AGTGGCTCTA GGGAAGGTGA GGTGCATAGA ATTGAGAGAT GCTCAGTAGA TGGCATGAGC    4980

AGTGCTTGAT GATTGTCTGG GTTGGTGGAG GAAGGTGGAC AGGGAAAAGC AGAAAGCTAC    5040

GATGGTGCCT CAAGGGGCTG AGTGATGTCA CTCACAGAGA CAGAATGTAT AGAGTGAATG    5100

TTCAGACTCA CAGGAAGTCC AAAACTACAT ACCCCAACGT GAGGTGCTGT GGGACATCCG    5160

GGGTGCAGGG TCCAGAGAGC AGGTAGGTAG AGTTTAGAAG AGGGCTGGGT CCACAATGCA    5220

GCCTTGGATG TTCTCAATGT AAGAGTTGTG GGAGATGAAG CCTTGTGAGT GGATGGGAAC    5280

ACCCAGGTGC ATTTCAGGTG AAGCAAGGGG ACAAGAGGCT GAGGACACAG ACAAGCAAAT    5340

CCTAGATCTT CCATCAGTCC CTAGAAGGCA CGATGTGTGC CCCTCCCAGC ACACAGCCTG    5400

AGCCCTAGCA CAGAGCTGGC CGCAGAGAGG GCAGCAGTGA ATGTGTCCTC GGTGGTTCCT    5460

CCAGATGGGG CCTTTGTCCG CAGTGCACTT GTCTCTGCCT GGGTTGCTAT AGTAACCCAC    5520

AGATGCAGAG AGACTTGGCC TCCGTGTTGC CATGGAAACC AGCAATTGGG TGTCCCTGTG    5580

TGGCATGGCC ACTGAGACCT TGAGGATTCA GTCTGGTCCT GAAGGGTTTG GGGGGAGACT    5640

GCGACCAGAA GATGTTTCCA TGTCCTAATT AATGGGTGAT GGTGGTTGTT AGTCTGACTG    5700

TTGCCACGGT GATGAAGGGA GACATCCAAG TGCTGGTTTC AGTACTGAGG CGAATACAGG    5760

GAATTTCAAC AGGCTCCAGG TCTTACTATG CAGCCTGAAG TGGGACCATC CCTTAAACCC    5820

ACTCCATCCT GTGGCCACGA TGGGGCCAG GACACCTTTG CCTTCTTTCT GGGTTTCTTT    5880

CTTTGCCGAG ACAGGGATTT TGTTCCCAGG AGGCACTCCC TGGCCCATGG GATCTCAGCA    5940

TTCAAAGCAG CACAGGAAAC CTGGGCCCCT GAAACGGGGC CACCGAAGAG ATCG         5994

(2) INFORMATION FOR SEQ ID NO:12:

(i) SEQUENCE CHARACTERISTICS:
        (A) LENGTH: 2115 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

AGAATTCAGC GGCCGCTGAA TTCTAGCAAA GGCACCATGC CTCTGCGGGA TGAAACCCTC      60

CGAGAGGTGT GGGCCTCTGA CAGTGGGCAT GAAGAAGAAA GCCTGAGCCC GGAGGCCCCG     120

CGGCGCCCCA AACAGCGACC CGCCCCGGCA CAGAGGCTAA GGAAGAAGAG GACGGAGGCC     180

CCCGAATCCC CCTGCCCCAC GGGATCCAAG CCCCGGAAGC CCGGAGCTGG GCGGAGGGGG     240

AGGCCGCGGG AGGAGCCTTC CCCAGACCCA GCCCAGGCCC GGGCGCCGCA GACGGTCTAC     300

GCCAGGTTCC TCAGGGACCC CGAGGCCAAG AAGCGCGACC CCCGGGAAAC CTTTCTGGTA     360

GCCCGTGCCC CAGACGCGGA GGACGAGGAG GAGGAGGAAG AGGAGGACGA GGAGGACGAG     420

GAAGAGGAGG CAGAGGAAAA GAAAGAGAAA ATCCTTCTGC CTCCCAAGAA GCCCCTGAGA     480

GAGAAGAGCT CCGCAGACCT GAAGGAGAGG AGGGCCAAGG CCCAGGGCCC AAGGGGAGAC     540

CTGGGAAGCC CTGACCCCCC ACCGAAACCT CTGCGTGTTA GGAATAAGGA AGCTCCAGCA     600

GGGGAGGGGA CCAAGATGAG AAAGACCAAG AAGAAAGGGT CTGGGGAGGC CGACAAGGAC     660

CCCTCAGGGA GCCCAGCCAG TGCGAGGAAG AGCCCAGCAG CCATGTTTCT GGTTGGGGAA     720

GRCAGTCCTG ACAAGAAAGC CCTGAAGAAG AAAGGCACTC CAAAGGCGC GAGGAAGGAG     780

GAAGAAGAGG AGGAGGAGGC AGCTACGGTG ATAAAGAACA GCAATCAAAA GGGCAAAGCC     840

AAAGGAAAAG GCAAAAAGAA AGCGAAGGAG GAGAGGGCCC CGTCTCCCCC CGTGGAGGTG     900
```

```
GACGAACCCC GGGAGTTTGT GCTCCGGCCT GCCCCCCAGG GCCGCACGGT GCGCTGCCGG      960

CTGACCCGGG ACAAAAAGGG CATGGATCGA GGCATGTATC CCTCCTACTT CCTGCACCTG     1020

GACACGGAGA AGAAGGTGTT CCTCTTGGCT GGCAGGAAAC GAAAACGGAG CAAGACAGCC     1080

AATTACCTCA TCTCCATCGA CCCTACCAAT CTGTCCCGAG GAGGGGAGAA TTTCATCGGG     1140

AAGCTGAGGT CCAACCTCCT GGGGAACCGC TTCACGGTCT TTGACAACGG GCAGAACCCA     1200

CAGCGTGGGT ACAGCACTAA TGTGGCAAGC CTTCGGCAGG AGCTGGCAGC TGTGATCTAT     1260

GAAACCAACG TGCTGGGCTT CCGTGGCCCC CGGCGCATGA CCGTCATCAT TCCTGGCATG     1320

AGTGCGGAGA ACGAGAGGGT CCCCATCCGG CCCCGAAATG CTAGTGACGG CCTGCTGGTG     1380

CGCTGGCAGA ACAAGACGCT GGAGAGCCTC ATAGAACTGC ACAACAAGCC ACCTGTCTGG     1440

AACGATGACA GTGGCTCCTA CACCCTCAAC TTCCAAGGCC GGGTCACCCA GCCTCAGTC     1500

AAGAACTTCC AGATTGTCCA CGCTGATGAC CCCGACTATA TCGTGCTGCA GTTCGGCCGC     1560

GTGGCGGAGG ACGCCTTCAC CCTAGACTAC CGGTACCCGC TGTGCGCCCT GCAGGCCTTC     1620

GCCATCGCCC TCTCCAGTTT CGACGGGAAG CTGGCTTGCG AGTGACCCCA GCAGCCCCTC     1680

AGCGCCCCCA GAGCCCGTCA GCGTGGGGGA AAGGATTCAG TGGAGGCTGG CAGGGTCCCT     1740

CCAGCAAAGC TCCCGCGGAA AACTGCTCCT GTGTCGGGGC TGACCTCTCA CTGCCTCTCG     1800

GTGACCTCCG TCCTCTCCCC AGCCTGGCAC AGGCCGAGGC AGGAGGAGCC CGGACGGCGG     1860

GTAGGACGGA GATGAAGAAC ATCTGGAGTT GGAGCCGCAC ATCTGGTTTC GGAGTTCGCC     1920

TGCGCCGCTG TGCCCCCCTC CTCCCCGCGC CCCAGTCAAT TCCTGTCCGG GAGCAGTAGT     1980

CATTGTTGTT TTAACCTCCC CTCTCCCCGG GACCGCGCTA GGGCTCCGAG GAGCTGGGGC     2040

GGGCTAGGGG AGGGGGTAGG TGATGGGGGA CGAGGGCCAG GCACCCACAT CCCCAATAAA     2100

GCCGCGTCCT TGGCA                                                     2115

(2) INFORMATION FOR SEQ ID NO:13:

(i) SEQUENCE CHARACTERISTICS:
        (A) LENGTH: 542 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met Pro Leu Arg Asp Glu Thr Leu Arg Glu Val Trp Ala Ser Asp Ser
 1               5                  10                  15

Gly His Glu Glu Glu Ser Leu Ser Pro Glu Ala Pro Arg Arg Pro Lys
            20                  25                  30

Gln Arg Pro Ala Pro Ala Gln Arg Leu Arg Lys Lys Arg Thr Glu Ala
        35                  40                  45

Pro Glu Ser Pro Cys Pro Thr Gly Ser Lys Pro Arg Lys Pro Gly Ala
    50                  55                  60

Gly Arg Arg Gly Arg Pro Arg Glu Glu Pro Ser Pro Asp Pro Ala Gln
65                  70                  75                  80

Ala Arg Ala Pro Gln Thr Val Tyr Ala Arg Phe Leu Arg Asp Pro Glu
                85                  90                  95

Ala Lys Lys Arg Asp Pro Arg Glu Thr Phe Leu Val Ala Arg Ala Pro
            100                 105                 110

Asp Ala Glu Asp Glu Glu Glu Glu Glu Asp Glu Glu Asp Glu
        115                 120                 125
```

-continued

```
Glu Glu Glu Ala Glu Glu Lys Lys Glu Lys Ile Leu Leu Pro Pro Lys
            130                 135                 140

Lys Pro Leu Arg Glu Lys Ser Ser Ala Asp Leu Lys Glu Arg Arg Ala
145                 150                 155                 160

Lys Ala Gln Gly Pro Arg Gly Asp Leu Gly Ser Pro Asp Pro Pro Pro
                165                 170                 175

Lys Pro Leu Arg Val Arg Asn Lys Glu Ala Pro Ala Gly Glu Gly Thr
                180                 185                 190

Lys Met Arg Lys Thr Lys Lys Lys Gly Ser Gly Glu Ala Asp Lys Asp
                195                 200                 205

Pro Ser Gly Ser Pro Ala Ser Ala Arg Lys Ser Pro Ala Ala Met Phe
            210                 215                 220

Leu Val Gly Glu Xaa Ser Pro Asp Lys Lys Ala Leu Lys Lys Lys Gly
225                 230                 235                 240

Thr Pro Lys Gly Ala Arg Lys Glu Glu Glu Glu Glu Glu Glu Ala Ala
                245                 250                 255

Thr Val Ile Lys Asn Ser Asn Gln Lys Gly Lys Ala Lys Gly Lys Gly
                260                 265                 270

Lys Lys Lys Ala Lys Glu Glu Arg Ala Pro Ser Pro Pro Val Glu Val
            275                 280                 285

Asp Glu Pro Arg Glu Phe Val Leu Arg Pro Ala Pro Gln Gly Arg Thr
            290                 295                 300

Val Arg Cys Arg Leu Thr Arg Asp Lys Lys Gly Met Asp Arg Gly Met
305                 310                 315                 320

Tyr Pro Ser Tyr Phe Leu His Leu Asp Thr Glu Lys Lys Val Phe Leu
                325                 330                 335

Leu Ala Gly Arg Lys Arg Lys Arg Ser Lys Thr Ala Asn Tyr Leu Ile
                340                 345                 350

Ser Ile Asp Pro Thr Asn Leu Ser Arg Gly Gly Glu Asn Phe Ile Gly
            355                 360                 365

Lys Leu Arg Ser Asn Leu Leu Gly Asn Arg Phe Thr Val Phe Asp Asn
            370                 375                 380

Gly Gln Asn Pro Gln Arg Gly Tyr Ser Thr Asn Val Ala Ser Leu Arg
385                 390                 395                 400

Gln Glu Leu Ala Ala Val Ile Tyr Glu Thr Asn Val Leu Gly Phe Arg
                405                 410                 415

Gly Pro Arg Arg Met Thr Val Ile Ile Pro Gly Met Ser Ala Glu Asn
                420                 425                 430

Glu Arg Val Pro Ile Arg Pro Arg Asn Ala Ser Asp Gly Leu Leu Val
            435                 440                 445

Arg Trp Gln Asn Lys Thr Leu Glu Ser Leu Ile Glu Leu His Asn Lys
450                 455                 460

Pro Pro Val Trp Asn Asp Asp Ser Gly Ser Tyr Thr Leu Asn Phe Gln
465                 470                 475                 480

Gly Arg Val Thr Gln Ala Ser Val Lys Asn Phe Gln Ile Val His Ala
                485                 490                 495

Asp Asp Pro Asp Tyr Ile Val Leu Gln Phe Gly Arg Val Ala Glu Asp
            500                 505                 510

Ala Phe Thr Leu Asp Tyr Arg Tyr Pro Leu Cys Ala Leu Gln Ala Phe
            515                 520                 525

Ala Ile Ala Leu Ser Ser Phe Asp Gly Lys Leu Ala Cys Glu
            530                 535                 540
```

(2) INFORMATION FOR SEQ ID NO:14:

(i) SEQUENCE CHARACTERISTICS:
        (A) LENGTH: 1733 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

```
GGAATCCTCC CTCCCTCTGA GCCGTCTTTC TTCTCCTCCC TATTTCGCAG ATATCCCGAG      60

ATTAGGTCCC CAGCTTCCAA AGAGAGGATC AGAATGTCTC AGGATAATGA CACATTGATG     120

AGAGACATCC TGGGGCATGA GCTCGCTGCT ATGAGGCTGC AGAAGCTGGA ACAGCAGCGG     180

CGGCTGTTTG AAAAGAAGCA GCGACAGAAG CGCCAGGAGC TCCTCATGGT TCAGGCCAAT     240

CCTGACGCTT CCCCGTGGCT TTGGCGCTCT TGTCTGCGGG AGGAGCGCCT TTTAGGTGAC     300

AGAGGCCTTG GGAACCCTTT CCTCCGGAAG AAAGTGTCAG AGGCACATCT GCCCTCTGGC     360

ATCCACAGTG CCCTGGGCAC CGTGAGCTGT GGTGGAGACG GCAGGGGCGA GCGCGGCCTC     420

CCGACACCGC GGACAGAAGC AGTGTTCAGG AATCTCGGTC TCCAGTCCCC TTTCTTATCC     480

TGGCTCCCAG ACAATTCCGA TGCAGAATTG GAGGAAGTCT CCGTGGAGAA TGGTTCCGTC     540

TCTCCCCCAC CTTTTAAACA GTCTCCGAGA ATCCGACGCA AGGGTTGGCA AGCCCACCAA     600

CGACCTGGGA CCCGTGCAGA GGGTGAGAGT GACTCCCAGG ATATGGGAGA TGCACACAAG     660

TCACCCAATA TGGGACCAAA CCCTGGAATG GATGGTGACT GTGTATATGA AAACTTGGCC     720

TTCCAAAAGG AAGAAGACTT GGAAAAGAAG AGAGAGGCCT CTGAGTCTAC AGGGACGAAC     780

TCCTCAGCAG CACACAACGA AGAGTTGTCC AAGGCCCTGA AAGGCGAGGG TGGCACGGAC     840

AGCGACCATA TGAGGCACGA AGCCTCCTTG GCAATCCGCT CCCCCTGCCC TGGGCTGGAG     900

GAGGACATGG AAGCCTACGT GCTGCGGCCA GCGCTCCCGG GCACCATGAT GCAGTGCTAC     960

CTCACCCGTG ACAAGCACGG CGTGGACAAG GGCTTGTTCC CCCTCTACTA CCTCTACCTG    1020

GAGACCTCTG ACAGCCTGCA GCGCTTCCTC CTGGCTGGGC GAAAGAGAAG AAGGAGCAAA    1080

ACTTCTAATT ACCTCATCTC CCTGGATCCT ACACTCCTAT CTCGGGACGG GGACAATTTC    1140

GTGGGCAAAG TCAGATCCAA TGTCTTCAGC ACCAAGTTCA CCATCTTTGA CAATGGGGTG    1200

AATCCTGACC GGGAGCATTT AACCAGGAAT ACTGCCCGGA TCAGACAGGA GCTGGGGGCT    1260

GTGTGTTATG AGCCCAACGT CTTAGGATAC CTGGGGCCTC GGAAAATGAC TGTGATTCTC    1320

CCAGGAACCA ACAGCCAGAA CCAGCGAATC AATGTCCAGC CACTAAATGA ACAGGAGTCG    1380

CTACTGAGTC GTTACCAACG TGGGGACAAA CAAGGGTTGC TTTTGTTGCA CAACAAAACC    1440

CCGTCGTGGG ACAAGGAGAA CGGTGTCTAC ACGCTCAATT TCCATGGTCG AGTCACTCGG    1500

GCTTCGGTGA AGAACTTCCA AATCGTGGAT CCCAAACACC AAGAACATCT GGTGCTCCAG    1560

TTCGGCCGAG TGGGCCCAGA CACATTCACC ATGGACTTCT GCTTTCCATT TAGCCCGCTC    1620

CAGGCCTTCA GCATCTGCTT GTCCAGTTTC AATTAGAAGC TGGCTGTTGA ATAACTCAAT    1680

AAAATACCAT ACCCTTGCCA GCAAAAAAAA AAAAAAAAA AAAAAAAAAA AAA            1733
```

(2) INFORMATION FOR SEQ ID NO:15:

(i) SEQUENCE CHARACTERISTICS:
        (A) LENGTH: 520 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
Met Ser Gln Asp Asn Asp Thr Leu Met Arg Asp Ile Leu Gly His Glu
 1               5                  10                  15

Leu Ala Ala Met Arg Leu Gln Lys Leu Glu Gln Gln Arg Arg Leu Phe
                20                  25                  30

Glu Lys Lys Gln Arg Gln Lys Arg Gln Glu Leu Leu Met Val Gln Ala
            35                  40                  45

Asn Pro Asp Ala Ser Pro Trp Leu Trp Arg Ser Cys Leu Arg Glu Glu
        50                  55                  60

Arg Leu Leu Gly Asp Arg Gly Leu Gly Asn Pro Phe Leu Arg Lys Lys
65                  70                  75                  80

Val Ser Glu Ala His Leu Pro Ser Gly Ile His Ser Ala Leu Gly Thr
                85                  90                  95

Val Ser Cys Gly Gly Asp Gly Arg Gly Glu Arg Gly Leu Pro Thr Pro
                100                 105                 110

Arg Thr Glu Ala Val Phe Arg Asn Leu Gly Leu Gln Ser Pro Phe Leu
            115                 120                 125

Ser Trp Leu Pro Asp Asn Ser Asp Ala Glu Leu Glu Glu Val Ser Val
        130                 135                 140

Glu Asn Gly Ser Val Ser Pro Pro Phe Lys Gln Ser Pro Arg Ile
145                 150                 155                 160

Arg Arg Lys Gly Trp Gln Ala His Gln Arg Pro Gly Thr Arg Ala Glu
                165                 170                 175

Gly Glu Ser Asp Ser Gln Asp Met Gly Asp Ala His Lys Ser Pro Asn
                180                 185                 190

Met Gly Pro Asn Pro Gly Met Asp Gly Asp Cys Val Tyr Glu Asn Leu
            195                 200                 205

Ala Phe Gln Lys Glu Glu Asp Leu Glu Lys Lys Arg Glu Ala Ser Glu
        210                 215                 220

Ser Thr Gly Thr Asn Ser Ser Ala Ala His Asn Glu Glu Leu Ser Lys
225                 230                 235                 240

Ala Leu Lys Gly Glu Gly Gly Thr Asp Ser Asp His Met Arg His Glu
                245                 250                 255

Ala Ser Leu Ala Ile Arg Ser Pro Cys Pro Gly Leu Glu Glu Asp Met
                260                 265                 270

Glu Ala Tyr Val Leu Arg Pro Ala Leu Pro Gly Thr Met Met Gln Cys
            275                 280                 285

Tyr Leu Thr Arg Asp Lys His Gly Val Asp Lys Gly Leu Phe Pro Leu
        290                 295                 300

Tyr Tyr Leu Tyr Leu Glu Thr Ser Asp Ser Leu Gln Arg Phe Leu Leu
305                 310                 315                 320

Ala Gly Arg Lys Arg Arg Ser Lys Thr Ser Asn Tyr Leu Ile Ser
                325                 330                 335

Leu Asp Pro Thr Leu Leu Ser Arg Asp Gly Asp Asn Phe Val Gly Lys
            340                 345                 350

Val Arg Ser Asn Val Phe Ser Thr Lys Phe Thr Ile Phe Asp Asn Gly
        355                 360                 365

Val Asn Pro Asp Arg Glu His Leu Thr Arg Asn Thr Ala Arg Ile Arg
        370                 375                 380

Gln Glu Leu Gly Ala Val Cys Tyr Glu Pro Asn Val Leu Gly Tyr Leu
385                 390                 395                 400
```

```
Gly Pro Arg Lys Met Thr Val Ile Leu Pro Gly Thr Asn Ser Gln Asn
                405                 410                 415
Gln Arg Ile Asn Val Gln Pro Leu Asn Glu Gln Glu Ser Leu Leu Ser
            420                 425                 430
Arg Tyr Gln Arg Gly Asp Lys Gln Gly Leu Leu Leu Leu His Asn Lys
        435                 440                 445
Thr Pro Ser Trp Asp Lys Glu Asn Gly Val Tyr Thr Leu Asn Phe His
    450                 455                 460
Gly Arg Val Thr Arg Ala Ser Val Lys Asn Phe Gln Ile Val Asp Pro
465                 470                 475                 480
Lys His Gln Glu His Leu Val Leu Gln Phe Gly Arg Val Gly Pro Asp
                485                 490                 495
Thr Phe Thr Met Asp Phe Cys Phe Pro Phe Ser Pro Leu Gln Ala Phe
                500                 505                 510
Ser Ile Cys Leu Ser Ser Phe Asn
                515                 520
```

(2) INFORMATION FOR SEQ ID NO:16:

(i) SEQUENCE CHARACTERISTICS:
       (A) LENGTH: 1482 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:16:

```
CGGAGAAGAG TGTGTAACGT GGTGGGGGCT TCNTCGGTGG CGGGCATGGA GGCTTCGCGC      60
TGCCGGCTCA GTCCCAGCGG CGACAGTGTC TTCCATGAAG AAATGATGAA GATGCGACAG     120
GCTAAGCTGG ATTATCAGAG CTACTACTTT GAGAAGAGGC AAAGGAAAAA GCGCCTTGAG     180
CCATTTATGG TGCAGCCCAA TCCAGAAGCC AGGCTACGTC GGGCAAAGCC AAGGGCCAGT     240
GATGAGCAGA CTCCCTTGGT GAACTGTCAT ACTCCCCACA GCAATGTCAT CTTACATGGT     300
ATTGATGGTC CAGCTGCTGT CCTGAAACCA GACGAAGTTC ATGCTCCATC AGTAAGCTCC     360
TCTGTTGTGG AAGAAGATGC TGAAAACACC GTGGATACTG CTTCCAAGCC AGGACTTCAG     420
GAGCGTCTCC AAAAGCATGA TATCTCTGAA AGTGTGAACT TCGATGAGGA GACTGATGGA     480
ATATCCCAGT CAGCATGTTT AGAAAGACCC AATTCTGCAT CAAGCCAGAA TTCAACCGAT     540
ACAGGCATTC CGGTTCTGCT ACTGCCGCCC AACCAGCTGA TAACCTTCCT GGGAGACATA     600
GACGACCTGG AGGACTTTGT GTTAGTCCCT GCCCCTCAAG GTGTCACAGT AAGATGTCGG     660
ATAATCCGGG ATAAAAGGGG AATGGATCGG GGTCTTTTTT CCCACCTACT ATATGTACTT     720
GGAAAAGAAG AAAATCAGAA GATATTTCTT CTTGCAGCTA GAAAGCGGAA AAGAGCAAA     780
ACAGCCAACT ACCTTATCTC CATTGATCCA GTTGATTTAT CTCGTGAAGG AGAAAGTTAT     840
GTCGGCAAGC TTAGATCCAA CCTCATGGGG ACCAAGTTTA CAGTTTATGA CCGTGGCATC     900
TGCCCCATGA AGGGCCGGGG TTTGGTAGGA GCGGCCCACA CCCGGCAGGA GCTGGCTGCC     960
ATCTCCTATG AAACAAACGT ACTTGGATTT AAAGGTCCTA GGAAAATGTC TGTGATCATT    1020
CCTGGAATGA CACTGAATCA TAAGCAGATC CCCTATCAGC CACAAAACAA CCATGACAGT    1080
TTGCTCTCAA GGTGGCAGAA CAGAACTATG GAAAATCTGG TTGAGCTGCA CAACAAGGCC    1140
CCCGTCTGGA ACAGTGACAC TCAGTCCTAT GTCCTCAACT TCCGTGGCCG GGTCACTCAG    1200
GCGTCTGTGA AGAACTTCCA GCTAGTCCAC AAAAATGACC CTGATTATAT AGTCATGCAG    1260
```

```
TTTGGACGTG TGGCAGATGA CGTGTTCACA CTGGATTACA ACTACCCACT TTGTGCAGTA    1320

CAAGCCTTTG CCATCTCCCT TTCTAGCTTT GACAGTAAGC TGGCGTGTGA ATGAGAGAAC    1380

AGTCAGGCAG GGAGCCCTTC TCCCCACAGA GCTTTCAGGA GCAGACNTNG GCCGNCCGAC    1440

CTGCCAGGGC GGNCGCCAAA ACCCTATAGT GAGATTAATC CC                       1482
```

(2) INFORMATION FOR SEQ ID NO:17:

(i) SEQUENCE CHARACTERISTICS:
        (A) LENGTH: 442 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Met Glu Ala Ser Arg Cys Arg Leu Ser Pro Ser Gly Asp Ser Val Phe
  1               5                  10                  15

His Glu Glu Met Met Lys Met Arg Gln Ala Lys Leu Asp Tyr Gln Arg
                 20                  25                  30

Leu Leu Leu Glu Lys Arg Gln Arg Lys Lys Arg Leu Glu Pro Phe Met
             35                  40                  45

Val Gln Pro Asn Pro Glu Ala Arg Leu Arg Arg Ala Lys Pro Arg Ala
 50                  55                  60

Ser Asp Glu Gln Thr Pro Leu Val Asn Cys His Thr Pro His Ser Asn
 65                  70                  75                  80

Val Ile Leu His Gly Ile Asp Gly Pro Ala Ala Val Leu Lys Pro Asp
                 85                  90                  95

Glu Val His Ala Pro Ser Val Ser Ser Val Val Glu Glu Asp Ala
            100                 105                 110

Glu Asn Thr Val Asp Thr Ala Ser Lys Pro Gly Leu Gln Glu Arg Leu
            115                 120                 125

Gln Lys His Asp Ile Ser Glu Ser Val Asn Phe Asp Glu Glu Thr Asp
        130                 135                 140

Gly Ile Ser Gln Ser Ala Cys Leu Glu Arg Pro Asn Ser Ala Ser Ser
145                 150                 155                 160

Gln Asn Ser Thr Asp Thr Gly Ile Pro Val Leu Leu Leu Pro Pro Asn
                165                 170                 175

Gln Leu Ile Thr Phe Leu Gly Asp Ile Asp Asp Leu Glu Asp Phe Val
            180                 185                 190

Leu Val Pro Ala Pro Gln Gly Val Thr Val Arg Cys Arg Ile Ile Arg
            195                 200                 205

Asp Lys Arg Gly Met Asp Arg Gly Leu Phe Ser His Leu Leu Tyr Val
        210                 215                 220

Leu Gly Lys Glu Glu Asn Gln Lys Ile Phe Leu Leu Ala Ala Arg Lys
225                 230                 235                 240

Arg Lys Lys Ser Lys Thr Ala Asn Tyr Leu Ile Ser Ile Asp Pro Val
                245                 250                 255

Asp Leu Ser Arg Glu Gly Glu Ser Tyr Val Gly Lys Leu Arg Ser Asn
            260                 265                 270

Leu Met Gly Thr Lys Phe Thr Val Tyr Asp Arg Gly Ile Cys Pro Met
            275                 280                 285

Lys Gly Arg Gly Leu Val Gly Ala Ala His Thr Arg Gln Glu Leu Ala
        290                 295                 300

Ala Ile Ser Tyr Glu Thr Asn Val Leu Gly Phe Lys Gly Pro Arg Lys
```

-continued

```
305                 310                 315                 320
Met Ser Val Ile Ile Pro Gly Met Thr Leu Asn His Lys Gln Ile Pro
                325                 330                 335
Tyr Gln Pro Gln Asn Asn His Asp Ser Leu Leu Ser Arg Trp Gln Asn
                340                 345                 350
Arg Thr Met Glu Asn Leu Val Glu Leu His Asn Lys Ala Pro Val Trp
                355                 360                 365
Asn Ser Asp Thr Gln Ser Tyr Val Leu Asn Phe Arg Gly Arg Val Thr
            370                 375                 380
Gln Ala Ser Val Lys Asn Phe Gln Leu Val His Lys Asn Asp Pro Asp
385                 390                 395                 400
Tyr Ile Val Met Gln Phe Gly Arg Val Ala Asp Asp Val Phe Thr Leu
                405                 410                 415
Asp Tyr Asn Tyr Pro Leu Cys Ala Val Gln Ala Phe Ala Ile Ser Leu
                420                 425                 430
Ser Ser Phe Asp Ser Lys Leu Ala Cys Glu
                435                 440
```

(2) INFORMATION FOR SEQ ID NO:18:

(i) SEQUENCE CHARACTERISTICS:
        (A) LENGTH: 1743 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

```
GGCACGAGGG ACCGTGAGGG CCAAGAGGGC CAAGAAGTGG AGCGTCTCAG GAGAATGAAC      60

AGTGGAAGAA AGAGACCCTG GAGGATGAAT TCTCTGGCGT GAGGCTGCAG AAGCTAGAAC     120

AACAGCGACA GCTATTTGAG AAGAAGCAGC GCAGGAAACG CCAGGAGCCC CTCATGGTTC     180

AGGCCAATCC TGATGCTACC CTGAGGCACC GGCGACCAAG GCGCGGGGAG GAGCGCTTCC     240

AGAGTGACAG CAGCTGGGGC CTTGGTGTTG GGAGCCCTTT CCTCCAGGAG AACGTTCCGC     300

AGGCACATCT GCCCTCAGGG GCGCACAGTG CCCTTGTCAC CATGAGCTAT GTCGCAGATG     360

GGAGTGGTGA GCGGGCCCCC CTACTGTCAC CCCGAGGAGC AGTATACACT CGGGGCAACG     420

GCCCTGCGGT CCGTCATCAT CTTTGCTGGC TTCCAGACAG CTCCGATTCA GACGTGGAGG     480

AAGTGACCAT GGAAGACATC CCCGTCATCT CCCGACCTCC CCAGACGAAT CTGGCAAACC     540

TACGCAGGGG CTGGTTAGCC TCCCCAGGAC CCGGGATCAG TCAAGAAGAA AAAGAAGAAG     600

AGGTTGGATC CACGGATGCC AGAGTTGAAG ACAAGACACC CAGCCCAGAC CCAGACCCAG     660

ACCCTACCGT GAACTCTGAC GGAGATCATG GAGACCTGGC ACCCTGCAAG GTGGAAGAAA     720

ACACAGCCCA GAAGAATACA GAAACAGCCT CTGGCATCGG GGATGAAGAC CGGGAGAAGG     780

GAGAGGTCAC AGAGTCTACA GAGACAAACT ATGCCCCAGT GGCATCCAAG GTTTTGCAAG     840

GCGACGATGG TGACGCCAGC AACCACAATG CCTGGAACAT GACCTGCCCC CAGCCTCGCA     900

TTCCCGGCCC TCGGCTCGGG GAGGACATGG AAGCATACGT GTTGCTCCCT GCACCCCGAG     960

ACCACATGGT GCAGTGGCGC ATCGTCCGAA ACAAGCACGG GATGGACAAG GGGATGTTCC    1020

CTTCCTACTA CCTCTACCTG GAGGGCGAGG ATGGTGTAGC ACATTTCCTT CTGGCTGGGC    1080

GGAAAAGGAA AAGAAGCAAA ACTTCAAATT ATCTCATCTC CCTGGACCCC AAAGACATGT    1140

CTCGCAATGG GAGCAACTTT GTAGGCAAAG TTAGATCCAA TGTCTTGGGC ACGAAATTCA    1200
```

```
CCATCTTCGA TAATGGGGTG AACCCTGAGC GGAGTTACTG GGTTCCAGAC AGTGCCCGGA    1260

TCAGAGAGGA GCTGGGAGTC GTCTGTTATG AGACCAATGT CTTGGGATTC AGGGGGCCTC    1320

GGAAAATGAC TGTGATCCTT CCAGGAATGG ACAGCCGGAA GCAGAGGATG AAAGTCCAGC    1380

CACAAAATGA TCAGGATTCC ATATTGAGTC GCGTACAGAA GGGCGCTGGA CACGGGCTGC    1440

TTCTACTGCA GAACAAGGCC CCATCGTGGA GCGACGAAAG CGGCGCATAC GTACTCAATT    1500

TTCACGGTCG CGTCACGCGG GCTTCAGTCA AGAACTTCCA GATAGTGCAC CCGGATGAAC    1560

CCGACCACCT GGTGCTCCAG TTTGGCCGTG TGGCCCCAAA CATATTCACG ATGGATTTCC    1620

GATATCCTCT TTGCCCGCTC CAAGCCTTCG CCATCTGCTT ATCCAGTTTC GATGGGAAAC    1680

TGGCGTGTGA GTAACTGAAT AAAATACCAT CCCTCACCAA CTCTGAAAAA AAAAAAAAA    1740

AAA                                                                 1743

(2) INFORMATION FOR SEQ ID NO:19:

(i) SEQUENCE CHARACTERISTICS:
        (A) LENGTH: 506 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

Met Val Gln Ala Asn Pro Asp Ala Thr Leu Arg His Arg Arg Pro Arg
 1               5                  10                  15

Arg Gly Glu Glu Arg Phe Gln Ser Asp Ser Ser Trp Gly Leu Gly Val
                20                  25                  30

Gly Ser Pro Phe Leu Gln Glu Asn Val Pro Gln Ala His Leu Pro Ser
            35                  40                  45

Gly Ala His Ser Ala Leu Val Thr Met Ser Tyr Val Ala Asp Gly Ser
        50                  55                  60

Gly Glu Arg Ala Pro Leu Leu Ser Pro Arg Gly Ala Val Tyr Thr Arg
65                  70                  75                  80

Gly Asn Gly Pro Ala Val Arg His His Leu Cys Trp Leu Pro Asp Ser
                85                  90                  95

Ser Asp Ser Asp Val Glu Glu Val Thr Met Glu Asp Ile Pro Val Ile
            100                 105                 110

Ser Arg Pro Pro Gln Thr Asn Leu Ala Asn Leu Arg Arg Gly Trp Leu
        115                 120                 125

Ala Ser Pro Gly Pro Gly Ile Ser Gln Glu Glu Lys Glu Glu Glu Val
    130                 135                 140

Gly Ser Thr Asp Ala Arg Val Glu Asp Lys Thr Pro Ser Pro Asp Pro
145                 150                 155                 160

Asp Pro Asp Pro Thr Val Asn Ser Asp Gly Asp His Gly Asp Leu Ala
                165                 170                 175

Pro Cys Lys Val Glu Glu Asn Thr Ala Gln Lys Asn Thr Glu Thr Ala
            180                 185                 190

Ser Gly Ile Gly Asp Glu Asp Arg Glu Lys Gly Glu Val Thr Glu Ser
        195                 200                 205

Thr Glu Thr Asn Tyr Ala Pro Val Ala Ser Lys Val Leu Gln Gly Asp
    210                 215                 220

Asp Gly Asp Ala Ser Asn His Asn Ala Trp Asn Met Thr Cys Pro Gln
225                 230                 235                 240

Pro Arg Ile Pro Gly Pro Arg Leu Gly Glu Asp Met Glu Ala Tyr Val
```

-continued

```
            245                 250                 255
Leu Leu Pro Ala Pro Arg Asp His Met Val Gln Trp Arg Ile Val Arg
            260                 265                 270
Asn Lys His Gly Met Asp Lys Gly Met Phe Pro Ser Tyr Tyr Leu Tyr
            275                 280                 285
Leu Glu Gly Glu Asp Gly Val Ala His Phe Leu Leu Ala Gly Arg Lys
            290                 295                 300
Arg Lys Arg Ser Lys Thr Ser Asn Tyr Leu Ile Ser Leu Asp Pro Lys
305                 310                 315                 320
Asp Met Ser Arg Asn Gly Ser Asn Phe Val Gly Lys Val Arg Ser Asn
                325                 330                 335
Val Leu Gly Thr Lys Phe Thr Ile Phe Asp Asn Gly Val Asn Pro Glu
                340                 345                 350
Arg Ser Tyr Trp Val Pro Asp Ser Ala Arg Ile Arg Glu Glu Leu Gly
                355                 360                 365
Val Val Cys Tyr Glu Thr Asn Val Leu Gly Phe Arg Gly Pro Arg Lys
                370                 375                 380
Met Thr Val Ile Leu Pro Gly Met Asp Ser Arg Lys Gln Arg Met Lys
385                 390                 395                 400
Val Gln Pro Gln Asn Asp Gln Asp Ser Ile Leu Ser Arg Val Gln Lys
                405                 410                 415
Gly Ala Gly His Gly Leu Leu Leu Gln Asn Lys Ala Pro Ser Trp
                420                 425                 430
Ser Asp Glu Ser Gly Ala Tyr Val Leu Asn Phe His Gly Arg Val Thr
                435                 440                 445
Arg Ala Ser Val Lys Asn Phe Gln Ile Val His Pro Asp Glu Pro Asp
450                 455                 460
His Leu Val Leu Gln Phe Gly Arg Val Ala Pro Asn Ile Phe Thr Met
465                 470                 475                 480
Asp Phe Arg Tyr Pro Leu Cys Pro Leu Gln Ala Phe Ala Ile Cys Leu
                485                 490                 495
Ser Ser Phe Asp Gly Lys Leu Ala Cys Glu
                500                 505
```

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:20:

TTCACAAAAG CACACCTGG                                  19

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GTCCCAAGGA TGGAGACCT                                  19

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TGGTGAGCAA AACAAGGAAC                                                        20

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

TGGGGAAAGC AATTTCTGG                                                         19

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GCCTGTCAGC AAGGACCTT                                                         19

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CCATGTCCCA AACAAGATGG                                                       20

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

ACCTGAGGCA GCAGAAGCT                                                         19

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

CAGCCAGTCT CTGGTTGGT                                               19

(2) INFORMATION FOR SEQ ID NO:28:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

TGCAGAACAA GACGCCAGT                                               19

(2) INFORMATION FOR SEQ ID NO:29:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GATGTTGTAC GCATGGTGC                                               19

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

TGGAGACAGG GAGACCAGG                                               19

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GATGGCAAGA AGGTGTTCC                                               19

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:32:

TCATTGCGGG GGCGGATAC                                                        19

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

ATGGTGAAGG TCGGTGTGAA                                                       20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

ACCAGTAGAC TCCACGACAT                                                       20

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

CTTAAACCCA CTCCATCCTG TG                                                    22

(2) INFORMATION FOR SEQ ID NO:36:

(i) SEQUENCE CHARACTERISTICS:
        (A) LENGTH: 3 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:36:

ggg                                                                          3

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA

```
        (xi) SEQUENCE DESCRIPTION: SEQ ID NO:37:

CTTAAACCCA CTCCATCCTG TG                                           22

(2) INFORMATION FOR SEQ ID NO:38:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:38:

ATCTCCCTTC CTTCCTTCCA GT                                           22

(2) INFORMATION FOR SEQ ID NO:39:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:39:

TGCCTGGGAA TCCTGCTGC                                               19

(2) INFORMATION FOR SEQ ID NO:40:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:40:

TCCTAAGGGT CCTGCCACT                                               19

(2) INFORMATION FOR SEQ ID NO:41:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:41:

CGAAAACGGA GCAAGACAG                                               19

(2) INFORMATION FOR SEQ ID NO:42:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:42:

TATGAGGCTC TCCAGCGTC                                               19
```

(2) INFORMATION FOR SEQ ID NO:43:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:43:

TCTACAGAGA CAAACTATGC CC                      22

(2) INFORMATION FOR SEQ ID NO:44:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:44:

GGAAATGTGC TACACCATCC TC                      22

(2) INFORMATION FOR SEQ ID NO:45:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:45:

CCACTAAATG AACAGGAGTC GC                      22

(2) INFORMATION FOR SEQ ID NO:46:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:46:

GAAACTGGAC AAGCAGATGC TG                      22

(2) INFORMATION FOR SEQ ID NO:47:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:47:

CCACTAAATG AACAGGAGTC GC                      22

(2) INFORMATION FOR SEQ ID NO:48:

(i) SEQUENCE CHARACTERISTICS:

(A) LENGTH: 22 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:48:

TTGGAAGTTC TTCACCGAAG CC                                              22

(2) INFORMATION FOR SEQ ID NO:49:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:49:

CCATCCTAAT ACGACTCACT ATAGGGC                                         27

(2) INFORMATION FOR SEQ ID NO:50:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:50:

AATCCAGTGT GAACACGTCA T                                               21

(2) INFORMATION FOR SEQ ID NO:51:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:51:

ACTCACTATA GGGCTCGAGC GGC                                             23

(2) INFORMATION FOR SEQ ID NO:52:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:52:

CACGTCCAAA CTGCATGACT                                                 20

(2) INFORMATION FOR SEQ ID NO:53:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:53:

GCCCCCGTCT GGAACAGTG                                                      19

(2) INFORMATION FOR SEQ ID NO:54:

(i) SEQUENCE CHARACTERISTICS:
             (A) LENGTH: 23 base pairs
             (B) TYPE: nucleic acid
             (C) STRANDEDNESS: double
             (D) TOPOLOGY: linear (ii) MOLECULE TYPE: cDNA (xi) SEQUENCE DESCRIPTION: SEQ ID NO:54:

ACTCACTATA GGGCTCGAGC GGC                                                 23

(2) INFORMATION FOR SEQ ID NO:55:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:55:

GCCCCCGTCT GGAACAGTG                                                      19

(2) INFORMATION FOR SEQ ID NO:56:

(i) SEQUENCE CHARACTERISTICS:
             (A) LENGTH: 2112 base pairs
             (B) TYPE: nucleic acid
             (C) STRANDEDNESS: double
             (D) TOPOLOGY: linear (ii) MOLECULE TYPE: cDNA (xi) SEQUENCE DESCRIPTION: SEQ ID NO:56:

GTCTTACTAT GCAGCCTGAA GTGGGACCAT CCCTTAAACC CACTCCATCC TGTGGCCACG         60

ATGGGGGCCA GGACACCTTT GCCTTCTTTC TGGGTTTCTT TCTTTGCCGA GACAGGGATT        120

TTGTTCCCAG GAGGCACTCC CTGGCCCATG GGATCTCAGC ATTCAAAGCA GCACAGGAAA        180

CCTGGGCCCC TGAAACGGGG CCACCGAAGA GATCGGAGAA CAACCAGGAG GAAGTACTGG        240

AAGGAAGGAA GGGAGATCGC TCGTGTCTTA GATGATGAGG GCAGAAACCT GAGGCAGCAG        300

AAGCTTGATC GGCAGCGGGC CCTGCTGGAG CAGAAGCAGA AGAAGAAGCG CCAGGAGCCC        360

CTGATGGTGC AGGCCAATGC AGATGGGCGG CCCCGGAGCC GGCGGGCCCG GCAGTCAGAG        420

GAACAAGCCC CCCTGGTGGA GTCCTACCTC AGCAGCAGTG GCAGCACCAG CTACCAAGTT        480

CAAGAGGCCG ACTCACTCGC CAGTGTGCAG CTGGGAGCCA CGCGCCCAAC AGCACCAGCT        540

TCAGCCAAGA GAACCAAGGC GGCAGCTACA GCAGGGGCC AGGGTGGCGC CGCTAGGAAG        600

GAGAAGAAGG GAAAGCACAA AGGCACCAGC GGGCCAGCAG CACTGGCAGA AGACAAGTCT        660

GAGGCCCAAG GCCCAGTGCA GATTCTGACT GTGGGCCAGT CAGACCACGC CCAGGACGCA        720

GGGGAGACGG CAGCTGGTGG GGGCGAACGG CCCAGCGGGC AGGATCTCCG TGCCACGATG        780

CAGAGGAAGG GCATCTCCAG CAGCATGAGC TTTGACGAGG ATGAGGAGGA TGAGGAGGAG        840

AATAGCTCCA GCTCCTCCCA GCTAAATAGT AACACCCGCC CCAGCTCTGC TACTAGCAGG        900

```
AAGTCCGTCA GGGAGGCAGC CTCAGCCCCT AGCCCAACAG CTCCAGAGCA ACCAGTGGAC     960

GTTGAGGTCC AGGATCTTGA GGAGTTTGCA CTGAGGCCGG CCCCCCAGGG TATCACCATC    1020

AAATGCCGCA TCACTCGGGA CAAGAAAGGG ATGGACCGGG GCATGTACCC CACCTACTTT    1080

CTGCACCTGG ACCGTGAGGA TGGGAAGAAG GTGTTCCTCC TGGCGGGAAG GAAGAGAAAG    1140

AAGAGTAAAA CTTCCAATTA CCTCATCTCT GTGGACCCAA CAGACTTGTC TCGAGGAGGG    1200

GACAGCTATA TCGGGAAACT GCGGTCCAAC TTGATGGGCA CCAAGTTCAC TGTTTATGAC    1260

AATGGAGTCA ACCCTCAGAA GGCCTCATCC TCCACTTTGG AAAGTGGAAC CTTACGTCAG    1320

GAGCTGGCAG CTGTGTGCTA CGAGACAAAC GTCTTAGGCT TCAAGGGGCC TCGGAAGATG    1380

AGCGTGATTG TCCCAGGCAT GAACATGGTT CATGAGAGAG TCTCTATCCG CCCCCGCAAC    1440

GAGCATGAGA CACTGCTAGC ACGCTGGCAG AATAAGAACA CGGAGAGTAT CATCGAGCTG    1500

CAAAACAAGA CACCTGTCTG GAATGATGAC ACACAGTCCT ATGTACTCAA CTTCCATGGG    1560

CGCGTCACAC AGGCCTCCGT GAAGAACTTC CAGATCATCC ATGGCAATGA CCCGGACTAC    1620

ATCGTGATGC AGTTTGGCCG GGTAGCAGAG GATGTGTTCA CCATGGATTA CAACTACCCG    1680

CTGTGTGCAC TGCAGGCCTT TGCCATTGCC CTGTCCAGCT TCGACAGCAA GCTGGCGTGC    1740

GAGTAGAGGC CTCTTCGTGC CCTTTGGGGT TGCCCAGCCT GGAGCGGAGC TTGCCTGCCT    1800

GCCTGTGGAG ACAGCCCTGC CTATCCTCTG TATATAGGCC TTCCGCCAGA TGAAGCTTTG    1860

GCCCTCAGTG GGCTCCCTGG CCCAGCCAGC CAGGAACTGG CTCCTTTGGC TCTGCTACTG    1920

AGGCAGGGGA GTAGTGGAGA GCGGGTGGGT GGGTGTTGAA GGGATTGAGA ATTAATTCTT    1980

TCCATGCCAC GAGGATCAAC ACACACTCCC ACCCTTGGGT AGTAAGTGGT TGTTGTNAGT    2040

CGGTACTTAC CAAAGCTTGA GCAACCTCTT CCAAGCTTGG GAAAGGGCCG CAAAAAGGCA    2100

TTAGGAGGGG AG                                                        2112

(2) INFORMATION FOR SEQ ID NO:57:

(i) SEQUENCE CHARACTERISTICS:
        (A) LENGTH: 2368 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:57:

CCCGGGCAGT CCTAAGCCCA CTGTTTATTG TCGACCCAGT GCACTTGCTA GCGGACGGCA      60

GGATGAGATC CTCAGTCCCG CCTTGTACAC AGCTTGCTCT CTGTAGAGCA TCATACCGTC     120

ATGATAGAAA TAGTCTGACG GGCTCTTCTC TGAGTCTGTC CAGACAGCGT CCCAATGGAA     180

ACCAGCTGAA ACGCCCAAGG CTTCTTAAAA GCAGATCCTT CTGAAAACAG GCACGTGGCC     240

TGGGAACTCA GGGTTTCTCT TGAGAATTGT TACTCTAATC TCAGCTCCTG TGGGGATTC     300

AGGGGTTTCC AGGTTATTTT GTGTCTCTCC CCACAACCAC CAGCAACACC CTCACACGTG     360

CGCACATACA GGTCACCCAC AGGCTCTCCT GCAGACACAT GTAGTCACAC TTCAGTCTCA     420

CATGGATTAG GGAGCTGTTT CCATCATGGA ACCAGGGACT GGGGCTGTGC TGACTGAGAA     480

GAGCTGCTGC GCCAGACAGA CGTCCAGGCT GGGGCACAGT GTCTTAGATG ATGAGGGCAG     540

AAACCTGAGG CAGCAGAAGC TTGATCGGCA GCGGGCCCTG CTGGAGCAGA AGCAGAAGAA     600

GAAGCGCCAG GAGCCCCTGA TGGTGCAGGC CAATGCAGAT GGGCGGCCCC GGAGCCGGCG     660

GGCCCGGCAG TCAGAGGAAC AAGCCCCCCT GGTGGAGTCC TACCTCAGCA GCAGTGGCAG     720
```

```
CACCAGCTAC CAAGTTCAAG AGGCCGACTC ACTCGCCAGT GTGCAGCTGG GAGCCACGCG    780

CCCAACAGCA CCAGCTTCAG CCAAGAGAAC CAAGGCGGCA GCTACAGCAG GGGGCCAGGG    840

TGGCGCCGCT AGGAAGGAGA AGAAGGGAAA GCACAAAGGC ACCAGCGGGC CAGCAGCACT    900

GGCAGAAGAC AAGTCTGAGG CCCAAGGCCC AGTGCAGATT CTGACTGTGG GCCAGTCAGA    960

CCACGCCCAG GACGCAGGGG AGACGGCAGC TGGTGGGGGC GAACGGCCCA GCGGGCAGGA   1020

TCTCCGTGCC ACGATGCAGA GGAAGGGCAT CTCCAGCAGC ATGAGCTTTG ACGAGGATGA   1080

GGAGGATGAG GAGGAGAATA GCTCCAGCTC CTCCCAGCTA AATAGTAACA CCCGCCCCAG   1140

CTCTGCTACT AGCAGGAAGT CCGTCAGGGA GGCAGCCTCA GCCCCTAGCC AACAGCTCC    1200

AGAGCAACCA GTGGACGTTG AGGTCCAGGA TCTTGAGGAG TTTGCACTGA GGCCGGCCCC   1260

CCAGGGTATC ACCATCAAAT GCCGCATCAC TCGGGACAAG AAAGGGATGG ACCGGGGCAT   1320

GTACCCCACC TACTTTCTGC ACCTGGACCG TGAGGATGGA AGAAGGTGT TCCTCCTGGC    1380

GGGAAGGAAG AGAAAGAAGA GTAAAACTTC CAATTACCTC ATCTCTGTGG ACCCAACAGA   1440

CTTGTCTCGA GGAGGGGACA GCTATATCGG GAAACTGCGG TCCAACTTGA TGGGCACCAA   1500

GTTCACTGTT TATGACAATG GAGTCAACCC TCAGAAGGCC TCATCCTCCA CTTTGGAAAG   1560

TGGAACCTTA CGTCAGGAGC TGGCAGCTGT GTGCTACGAG ACAAACGTCT TAGGCTTCAA   1620

GGGGCCTCGG AAGATGAGCG TGATTGTCCC AGGCATGAAC ATGGTTCATG AGAGAGTCTC   1680

TATCCGCCCC CGCAACGAGC ATGAGACACT GCTAGCACGC TGGCAGAATA AGAACACGGA   1740

GAGTATCATC GAGCTGCAAA ACAAGACACC TGTCTGGAAT GATGACACAC AGTCCTATGT   1800

ACTCAACTTC CATGGGCGCG TCACACAGGC CTCCGTGAAG AACTTCCAGA TCATCCATGG   1860

CAATGACCCG GACTACATCG TGATGCAGTT TGGCCGGGTA GCAGAGGATG TGTTCACCAT   1920

GGATTACAAC TACCCGCTGT GTGCACTGCA GGCCTTTGCC ATTGCCCTGT CCAGCTTCGA   1980

CAGCAAGCTG GCGTGCGAGT AGAGGCCTCT TCGTGCCCTT TGGGGTTGCC CAGCCTGGAG   2040

CGGAGCTTCC TGCCTGCCTG TGGAGACAGC CCTGCCTATC CTCTGTATAT AGGCCTTCCG   2100

CCAGATGAAG CTTTGGCCCT CAGTGGGCTC CCTGGCCCAG CCAGCCAGGA ACTGGCTCCT   2160

TTGGCTCTGC TACTGAGGCA GGGGAGTAGT GGAGAGCGGG TGGGTGGGTG TTGAAGGGAT   2220

TGAGAATTAA TTCTTTCCAT GCCACGAGGA TCAACACACA CTCCCACCCT TGGGTAGTAA   2280

GTGGTTGTTG TNAGTCGGTA CTTTACCAAA GCTTGAGCAA CCTCTTCCAA GCTTGGGAAA   2340

GGGCCGCAAA AAGGCATTAG GAGGGGAG                                     2368
```

(2) INFORMATION FOR SEQ ID NO:58:

(i) SEQUENCE CHARACTERISTICS:
        (A) LENGTH: 518 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:58:

```
Met Glu Pro Gly Thr Gly Ala Val Leu Thr Glu Lys Ser Cys Cys Ala
 1               5                  10                  15

Arg Gln Thr Ser Arg Leu Gly His Ser Val Leu Asp Asp Glu Gly Arg
            20                  25                  30

Asn Leu Arg Gln Gln Lys Leu Asp Arg Gln Arg Ala Leu Leu Glu Gln
        35                  40                  45

Lys Gln Lys Lys Lys Arg Gln Glu Pro Leu Met Val Gln Ala Asn Ala
```

-continued

```
        50                  55                  60
Asp Gly Arg Pro Arg Ser Arg Ala Arg Gln Ser Glu Glu Gln Ala
65                  70                  75                  80

Pro Leu Val Glu Ser Tyr Leu Ser Ser Gly Ser Thr Ser Tyr Gln
                85                  90                  95

Val Gln Glu Ala Asp Ser Leu Ala Ser Val Gln Leu Gly Ala Thr Arg
            100                 105                 110

Pro Thr Ala Pro Ala Ser Ala Lys Arg Thr Lys Ala Ala Thr Ala
            115                 120                 125

Gly Gly Gln Gly Gly Ala Ala Arg Lys Glu Lys Lys Gly Lys His Lys
130                 135                 140

Gly Thr Ser Gly Pro Ala Ala Leu Ala Glu Asp Lys Ser Glu Ala Gln
145                 150                 155                 160

Gly Pro Val Gln Ile Leu Thr Val Gly Gln Ser Asp His Ala Gln Asp
                165                 170                 175

Ala Gly Glu Thr Ala Ala Gly Gly Glu Arg Pro Ser Gly Gln Asp
            180                 185                 190

Leu Arg Ala Thr Met Gln Arg Lys Gly Ile Ser Ser Met Ser Phe
        195                 200                 205

Asp Glu Asp Glu Glu Asp Glu Glu Asn Ser Ser Ser Ser Gln
        210                 215                 220

Leu Asn Ser Asn Thr Arg Pro Ser Ser Ala Thr Ser Arg Lys Ser Val
225                 230                 235                 240

Arg Glu Ala Ala Ser Ala Pro Ser Pro Thr Ala Pro Glu Gln Pro Val
                245                 250                 255

Asp Val Glu Val Gln Asp Leu Gly Glu Phe Ala Leu Arg Pro Ala Pro
            260                 265                 270

Gln Gly Ile Thr Ile Lys Cys Arg Ile Thr Arg Asp Lys Lys Gly Met
            275                 280                 285

Asp Arg Gly Met Tyr Pro Thr Tyr Phe Leu His Leu Asp Arg Glu Asp
        290                 295                 300

Gly Lys Lys Val Phe Leu Leu Ala Gly Arg Lys Arg Lys Lys Ser Lys
305                 310                 315                 320

Thr Ser Asn Tyr Leu Ile Ser Val Asp Pro Thr Asp Leu Ser Arg Gly
                325                 330                 335

Gly Asp Ser Tyr Ile Gly Lys Leu Arg Ser Asn Leu Met Gly Thr Lys
            340                 345                 350

Phe Thr Val Tyr Asp Asn Gly Val Asn Pro Gln Lys Ala Ser Ser Ser
        355                 360                 365

Thr Leu Glu Ser Gly Thr Leu Arg Gln Glu Leu Ala Ala Val Cys Tyr
        370                 375                 380

Glu Thr Asn Val Leu Gly Phe Lys Gly Pro Arg Lys Met Ser Val Ile
385                 390                 395                 400

Val Pro Gly Met Asn Met Val His Glu Arg Val Ser Ile Arg Pro Arg
                405                 410                 415

Asn Glu His Glu Thr Leu Leu Ala Arg Trp Gln Asn Lys Asn Thr Glu
            420                 425                 430

Ser Ile Ile Glu Leu Gln Asn Lys Thr Pro Val Trp Asn Asp Asp Thr
        435                 440                 445

Gln Ser Tyr Val Leu Asn Phe His Gly Arg Val Thr Gln Ala Ser Val
        450                 455                 460

Lys Asn Phe Gln Ile Ile His Gly Asn Asp Pro Asp Tyr Ile Val Met
465                 470                 475                 480
```

```
Gln Phe Gly Arg Val Ala Glu Asp Val Phe Thr Met Asp Tyr Asn Tyr
            485                 490                 495

Pro Leu Cys Ala Leu Gln Ala Phe Ala Ile Ala Leu Ser Ser Phe Asp
            500                 505                 510

Ser Lys Leu Ala Cys Glu
        515

(2) INFORMATION FOR SEQ ID NO:59:

(i) SEQUENCE CHARACTERISTICS:
        (A) LENGTH: 1936 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:59:
```

| | | |
|---|---|---|
| GCGGAGCCCC GAGCGGAGCC GGAGGCGGCG ATGGAGGGAG TCAGCAGCCA CCGGACCCTG | 60 |
| TCTTACAGCC GCTGGAGCTA TGACAGTGTC TTAGATGATG AGGGCAGAAA CCTGAGGCAG | 120 |
| CAGAAGCTTG ATCGGCAGCG GGCCCTGCTG GAGCAGAAGC AGAAGAAGAA GCGCCAGGAG | 180 |
| CCCCTGATGG TGCAGGCCAA TGCAGATGGG CGGCCCCGGA GCCGGCGGGC CCGGCAGTCA | 240 |
| GAGGAACAAG CCCCCCTGGT GGAGTCCTAC CTCAGCAGCA GTGGCAGCAC CAGCTACCAA | 300 |
| GTTCAAGAGG CCGACTCACT CGCCAGTGTG CAGCTGGGAG CCACGCGCCC AACAGCACCA | 360 |
| GCTTCAGCCA AGAGAACCAA GGCGGCAGCT ACAGCAGGGG CCAGGGTGG CGCCGCTAGG | 420 |
| AAGGAGAAGA AGGGAAAGCA CAAAGGCACC AGCGGGCCAG CAGCACTGGC AGAAGACAAG | 480 |
| TCTGAGGCCC AAGGCCCAGT GCAGATTCTG ACTGTGGGCC AGTCAGACCA CGCCCAGGAC | 540 |
| GCAGGGGAGA CGGCAGCTGG TGGGGGCGAA CGGCCCAGCG GGCAGGATCT CCGTGCCACG | 600 |
| ATGCAGAGGA AGGGCATCTC CAGCAGCATG AGCTTTGACG AGGATGAGGA GGATGAGGAG | 660 |
| GAGAATAGCT CCAGCTCCTC CCAGCTAAAT AGTAACACCC GCCCCAGCTC TGCTACTAGC | 720 |
| AGGAAGTCCG TCAGGGAGGC AGCCTCAGCC CCTAGCCCAA CAGCTCCAGA GCAACCAGTG | 780 |
| GACGTTGAGG TCCAGGATCT TGAGGAGTTT GCACTGAGGC CGGCCCCCCA GGGTATCACC | 840 |
| ATCAAATGCC GCATCACTCG GGACAAGAAA GGGATGGACC GGGGCATGTA CCCCACCTAC | 900 |
| TTTCTGCACC TGGACCGTGA GGATGGGAAG AAGGTGTTCC TCCTGGCGGG AAGGAAGAGA | 960 |
| AAGAAGAGTA AAACTTCCAA TTACCTCATC TCTGTGGACC CAACAGACTT GTCTCGAGGA | 1020 |
| GGGGACAGCT ATATCGGGAA ACTGCGGTCC AACTTGATGG GCACCAAGTT CACTGTTTAT | 1080 |
| GACAATGGAG TCAACCCTCA GAAGGCCTCA TCCTCCACTT TGGAAAGTGG AACCTTACGT | 1140 |
| CAGGAGCTGG CAGCTGTGTG CTACGAGACA AACGTCTTAG GCTTCAAGGG GCCTCGGAAG | 1200 |
| ATGAGCGTGA TTGTCCCAGG CATGAACATG GTTCATGAGA GAGTCTCTAT CCGCCCCCGC | 1260 |
| AACGAGCATG AGACACTGCT AGCACGCTGG CAGAATAAGA ACACGGAGAG TATCATCGAG | 1320 |
| CTGCAAAACA AGACACCTGT CTGGAATGAT GACACACAGT CCTATGTACT CAACTTCCAT | 1380 |
| GGGCGCGTCA CACAGGCCTC CGTGAAGAAC TTCCAGATCA TCCATGGCAA TGACCCGGAC | 1440 |
| TACATCGTGA TGCAGTTTGG CCGGGTAGCA GAGGATGTGT TCACCATGGA TTACAACTAC | 1500 |
| CCGCTGTGTG CACTGCAGGC CTTTGCCATT GCCCTGTCCA GCTTCGACAG CAAGCTGGCG | 1560 |
| TGCGAGTAGA GGCCTCTTCG TGCCCTTTGG GGTTGCCCAG CCTGGAGCGG AGCTTGCCTG | 1620 |
| CCTGCCTGTG GAGACAGCCC TGCCTATCCT CTGTATATAG GCCTTCCGCC AGATGAAGCT | 1680 |

```
TTGGCCCTCA GTGGGCTCCC TGGCCCAGCC AGCCAGGAAC TGGCTCCTTT GGCTCTGCTA      1740

CTGAGGCAGG GGAGTAGTGG AGAGCGGGTG GGTGGGTGTT GAAGGGATTG AGAATTAATT      1800

CTTTCCATGC CACGAGGATC AACACACACT CCCACCCTTG GGTAGTAAGT GGTTGTTGTN      1860

AGTCGGTACT TTACCAAAGC TTGAGCAACC TCTTCCAAGC TTGGGAAAGG GCCGCAAAAA      1920

GGCATTAGGA GGGGAG                                                     1936
```

(2) INFORMATION FOR SEQ ID NO:60:

(i) SEQUENCE CHARACTERISTICS:
        (A) LENGTH: 512 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

```
Met Glu Gly Val Ser Ser His Arg Thr Leu Ser Tyr Ser Arg Trp Ser
 1               5                  10                  15

Tyr Asp Ser Val Leu Asp Asp Glu Gly Arg Asn Leu Arg Gln Gln Lys
             20                  25                  30

Leu Asp Arg Gln Arg Ala Leu Leu Glu Gln Lys Gln Lys Lys Lys Arg
         35                  40                  45

Gln Glu Pro Leu Met Val Gln Ala Asn Ala Asp Gly Arg Pro Arg Ser
     50                  55                  60

Arg Arg Ala Arg Gln Ser Glu Glu Gln Ala Pro Leu Val Glu Ser Tyr
 65                  70                  75                  80

Leu Ser Ser Ser Gly Ser Thr Ser Tyr Gln Val Gln Glu Ala Asp Ser
                 85                  90                  95

Leu Ala Ser Val Gln Leu Gly Ala Thr Arg Pro Thr Ala Pro Ala Ser
            100                 105                 110

Ala Lys Arg Thr Lys Ala Ala Ala Thr Ala Gly Gly Gln Gly Gly Ala
        115                 120                 125

Ala Arg Lys Glu Lys Lys Gly Lys His Lys Gly Thr Ser Gly Pro Ala
    130                 135                 140

Ala Leu Ala Glu Asp Lys Ser Glu Ala Gln Gly Pro Val Gln Ile Leu
145                 150                 155                 160

Thr Val Gly Gln Ser Asp His Ala Gln Asp Ala Gly Glu Thr Ala Ala
                165                 170                 175

Gly Gly Gly Glu Arg Pro Ser Gly Gln Asp Leu Arg Ala Thr Met Gln
            180                 185                 190

Arg Lys Gly Ile Ser Ser Ser Met Ser Phe Asp Glu Asp Glu Glu Asp
        195                 200                 205

Glu Glu Glu Asn Ser Ser Ser Ser Gln Leu Asn Ser Asn Thr Arg
    210                 215                 220

Pro Ser Ser Ala Thr Ser Arg Lys Ser Val Arg Glu Ala Ala Ser Ala
225                 230                 235                 240

Pro Ser Pro Thr Ala Pro Glu Gln Pro Val Asp Val Glu Val Gln Asp
                245                 250                 255

Leu Glu Glu Phe Ala Leu Arg Pro Ala Pro Gln Gly Ile Thr Ile Lys
            260                 265                 270

Cys Arg Ile Thr Arg Asp Lys Lys Gly Met Asp Arg Gly Met Tyr Pro
        275                 280                 285

Thr Tyr Phe Leu His Leu Asp Arg Glu Asp Gly Lys Lys Val Phe Leu
    290                 295                 300
```

```
Leu Ala Gly Arg Lys Arg Lys Ser Lys Thr Ser Asn Tyr Leu Ile
305                 310                 315                 320

Ser Val Asp Pro Thr Asp Leu Ser Arg Gly Gly Asp Ser Tyr Ile Gly
                325                 330                 335

Lys Leu Arg Ser Asn Leu Met Gly Thr Lys Phe Thr Val Tyr Asp Asn
            340                 345                 350

Gly Val Asn Pro Gln Lys Ala Ser Ser Ser Thr Leu Glu Ser Gly Thr
            355                 360                 365

Leu Arg Gln Glu Leu Ala Ala Val Cys Tyr Glu Thr Asn Val Leu Gly
    370                 375                 380

Phe Lys Gly Pro Arg Lys Met Ser Val Ile Val Pro Gly Met Asn Met
385                 390                 395                 400

Val His Glu Arg Val Ser Ile Arg Pro Arg Asn Glu His Glu Thr Leu
                405                 410                 415

Leu Ala Arg Trp Gln Asn Lys Asn Thr Glu Ser Ile Ile Glu Leu Gln
            420                 425                 430

Asn Lys Thr Pro Val Trp Asn Asp Asp Thr Gln Ser Tyr Val Leu Asn
            435                 440                 445

Phe His Gly Arg Val Thr Gln Ala Ser Val Lys Asn Phe Gln Ile Ile
    450                 455                 460

His Gly Asn Asp Pro Asp Tyr Ile Val Met Gln Phe Gly Arg Val Ala
465                 470                 475                 480

Glu Asp Val Phe Thr Met Asp Tyr Asn Tyr Pro Leu Cys Ala Leu Gln
                485                 490                 495

Ala Phe Ala Ile Ala Leu Ser Ser Phe Asp Ser Lys Leu Ala Cys Glu
            500                 505                 510
```

(2) INFORMATION FOR SEQ ID NO:61:

(i) SEQUENCE CHARACTERISTICS:
        (A) LENGTH: 1890 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:61:

```
GACATGACTT CCAAGCCGCA TTCCGACTGG ATTCCCTACA GTGTCTTAGA TGATGAGGGC      60

AGAAACCTGA GGCAGCAGAA GCTTGATCGG CAGCGGGCCC TGCTGGAGCA GAAGCAGAAG     120

AAGAAGCGCC AGGAGCCCCT GATGGTGCAG GCCAATGCAG ATGGGCGGCC CCGGAGCCGG     180

CGGGCCCGGC AGTCAGAGGA ACAAGCCCCC CTGGTGGAGT CCTACCTCAG CAGCAGTGGC     240

AGCACCAGCT ACCAAGTTCA AGAGGCCGAC TCACTCGCCA GTGTGCAGCT GGGAGCCACG     300

CGCCCAACAG CACCAGCTTC AGCCAAGAGA ACCAAGGCGG CAGCTACAGC AGGGGGCCAG     360

GGTGGCGCCG CTAGGAAGGA GAAGAAGGGA AAGCACAAAG GCACCAGCGG GCCAGCAGCA     420

CTGGCAGAAG ACAAGTCTGA GGCCCAAGGC CCAGTGCAGA TTCTGACTGT GGGCCAGTCA     480

GACCACGCCC AGGACGCAGG GGAGACGGCA GCTGGTGGGG GCGAACGGCC CAGCGGGCAG     540

GATCTCCGTG CCACGATGCA GAGGAAGGGC ATCTCCAGCA GCATGAGCTT TGACGAGGAT     600

GAGGAGGATG AGGAGGAGAA TAGCTCCAGC TCCTCCCAGC TAAATAGTAA CACCCGCCCC     660

AGCTCTGCTA CTAGCAGGAA GTCCGTCAGG GAGGCAGCCT CAGCCCCTAG CCCAACAGCT     720

CCAGAGCAAC CAGTGGACGT TGAGGTCCAG GATCTTGAGG AGTTTGCACT GAGGCCGGCC     780
```

```
CCCCAGGGTA TCACCATCAA ATGCCGCATC ACTCGGGACA AGAAAGGGAT GGACCGGGGC      840

ATGTACCCCA CCTACTTTCT GCACCTGGAC CGTGAGGATG GGAAGAAGGT GTTCCTCCTG      900

GCGGGAAGGA AGAGAAAGAA GAGTAAAACT TCCAATTACC TCATCTCTGT GGACCCAACA      960

GACTTGTCTC GAGGAGGGGA CAGCTATATC GGGAAACTGC GGTCCAACTT GATGGGCACC     1020

AAGTTCACTG TTTATGACAA TGGAGTCAAC CCTCAGAAGG CCTCATCCTC CACTTTGGAA     1080

AGTGGAACCT TACGTCAGGA GCTGGCAGCT GTGTGCTACG AGACAAACGT CTTAGGCTTC     1140

AAGGGGCCTC GGAAGATGAG CGTGATTGTC CCAGGCATGA ACATGGTTCA TGAGAGAGTC     1200

TCTATCCGCC CCCGCAACGA GCATGAGACA CTGCTAGCAC GCTGGCAGAA TAAGAACACG     1260

GAGAGTATCA TCGAGCTGCA AAACAAGACA CCTGTCTGGA ATGATGACAC ACAGTCCTAT     1320

GTACTCAACT TCCATGGGCG CGTCACACAG GCCTCCGTGA AGAACTTCCA GATCATCCAT     1380

GGCAATGACC CGGACTACAT CGTGATGCAG TTTGGCCGGG TAGCAGAGGA TGTGTTCACC     1440

ATGGATTACA ACTACCCGCT GTGTGCACTG CAGGCCTTTG CCATTGCCCT GTCCAGCTTC     1500

GACAGCAAGC TGGCGTGCGA GTAGAGGCCT CTTCGTGCCC TTTGGGGTTG CCCAGCCTGG     1560

AGCGGAGCTT GCCTGCCTGC CTGTGGAGAC AGCCCTGCCT ATCCTCTGTA TATAGGCCTT     1620

CCGCCAGATG AAGCTTTGGC CCTCAGTGGG CTCCCTGGCC CAGCCAGCCA GGAACTGGCT     1680

CCTTTGGCTC TGCTACTGAG GCAGGGGAGT AGTGGAGAGC GGGTGGGTGG GTGTTGAAGG     1740

GATTGAGAAT TAATTCTTTC CATGCCACGA GGATCAACAC ACACTCCCAC CCTTGGGTAG     1800

TAAGTGGTTG TTGTNAGTCG GTACTTTACC AAAGCTTGAG CAACCTCTTC CAAGCTTGGG     1860

AAAGGGCCGC AAAAAGGCAT TAGGAGGGGA                                      1890

(2) INFORMATION FOR SEQ ID NO:62:

(i) SEQUENCE CHARACTERISTICS:
        (A) LENGTH: 506 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:62:

Met Thr Ser Lys Pro His Ser Asp Trp Ile Pro Tyr Ser Val Leu Asp
  1               5                  10                  15

Asp Glu Gly Arg Asn Leu Arg Gln Gln Lys Leu Asp Arg Gln Arg Ala
                 20                  25                  30

Leu Leu Glu Gln Lys Gln Lys Lys Arg Gln Glu Pro Leu Met Val
         35                  40                  45

Gln Ala Asn Ala Asp Gly Arg Pro Arg Ser Arg Arg Ala Arg Gln Ser
     50                  55                  60

Glu Glu Gln Ala Pro Leu Val Glu Ser Tyr Leu Ser Ser Ser Gly Ser
 65                  70                  75                  80

Thr Ser Tyr Gln Val Gln Glu Ala Asp Ser Leu Ala Ser Val Gln Leu
                 85                  90                  95

Gly Ala Thr Arg Pro Thr Ala Pro Ala Ser Ala Lys Arg Thr Lys Ala
                100                 105                 110

Ala Ala Thr Ala Gly Gly Gln Gly Gly Ala Ala Arg Lys Glu Lys Lys
            115                 120                 125

Gly Lys His Lys Gly Thr Ser Gly Pro Ala Ala Leu Ala Glu Asp Lys
        130                 135                 140

Ser Glu Ala Gln Gly Pro Val Gln Ile Leu Thr Val Gly Gln Ser Asp
```

```
145                 150                 155                 160
His Ala Gln Asp Ala Gly Glu Thr Ala Ala Gly Gly Glu Arg Pro
                165                 170                 175

Ser Gly Gln Asp Leu Arg Ala Thr Met Gln Arg Lys Gly Ile Ser Ser
            180                 185                 190

Ser Met Ser Phe Asp Glu Asp Glu Glu Asp Glu Glu Glu Asn Ser Ser
            195                 200                 205

Ser Ser Ser Gln Leu Asn Ser Asn Thr Arg Pro Ser Ser Ala Thr Ser
        210                 215                 220

Arg Lys Ser Val Arg Glu Ala Ala Ser Ala Pro Ser Pro Thr Ala Pro
225                 230                 235                 240

Glu Gln Pro Val Asp Val Glu Val Gln Asp Leu Glu Glu Phe Ala Leu
                245                 250                 255

Arg Pro Ala Pro Gln Gly Ile Thr Ile Lys Cys Arg Ile Thr Arg Asp
                260                 265                 270

Lys Lys Gly Met Asp Arg Gly Met Tyr Pro Thr Tyr Phe Leu His Leu
            275                 280                 285

Asp Arg Glu Asp Gly Lys Lys Val Phe Leu Leu Ala Gly Arg Lys Arg
        290                 295                 300

Lys Lys Ser Lys Thr Ser Asn Tyr Leu Ile Ser Val Asp Pro Thr Asp
305                 310                 315                 320

Leu Ser Arg Gly Gly Asp Ser Tyr Ile Gly Lys Leu Arg Ser Asn Leu
                325                 330                 335

Met Gly Thr Lys Phe Thr Val Tyr Asp Asn Gly Val Asn Pro Gln Lys
                340                 345                 350

Ala Ser Ser Thr Leu Glu Ser Gly Thr Leu Arg Gln Glu Leu Ala
            355                 360                 365

Ala Val Cys Tyr Glu Thr Asn Val Leu Gly Phe Lys Gly Pro Arg Lys
            370                 375                 380

Met Ser Val Ile Val Pro Gly Met Asn Met Val His Glu Arg Val Ser
385                 390                 395                 400

Ile Arg Pro Arg Asn Glu His Glu Thr Leu Leu Ala Arg Trp Gln Asn
                405                 410                 415

Lys Asn Thr Glu Ser Ile Ile Glu Leu Gln Asn Lys Thr Pro Val Trp
            420                 425                 430

Asn Asp Asp Thr Gln Ser Tyr Val Leu Asn Phe His Gly Arg Val Thr
            435                 440                 445

Gln Ala Ser Val Lys Asn Phe Gln Ile Ile His Gly Asn Asp Pro Asp
        450                 455                 460

Tyr Ile Val Met Gln Phe Gly Arg Val Ala Glu Asp Val Phe Thr Met
465                 470                 475                 480

Asp Tyr Asn Tyr Pro Leu Cys Ala Leu Gln Ala Phe Ala Ile Ala Leu
                485                 490                 495

Ser Ser Phe Asp Ser Lys Leu Ala Cys Glu
            500                 505

(2) INFORMATION FOR SEQ ID NO:63:

(i) SEQUENCE CHARACTERISTICS:
        (A) LENGTH: 2109 base pairs
        (B) TYPE: nucleic acid
        (C) STRANDEDNESS: double
        (D) TOPOLOGY: linear (ii) MOLECULE TYPE: cDNA
```

(xi) SEQUENCE DESCRIPTION: SEQ ID NO:63:

```
GTCTCTGTGT AAAATGGGTG CTGGACTCCT AAGGCCCACT GTGTTATTGT CGACCCAGGT      60
GCACGTGCTA GCGGACGGCA GGATGAGATC CTCAGGTCCC GCCTTGTAAC ACAGCTTGCT     120
CTCTGTTAGA GCCTCATACC AGTCACTGAT AGAAAATAGT TCTGACAGGG CTCTTCTCTG     180
AGTCTGTCCA GACAGCGTCC CAAATGGAAA CCAGCTGAAA CCGCCCAAGG CTTCTTAAAA     240
GCAGATCCTT CTGAAAACAG TGTCTTAGAT GATGAGGGCA GAAACCTGAG GCAGCAGAAG     300
CTTGATCGGC AGCGGGCCCT GCTGGAGCAG AAGCAGAAGA AGAAGCGCCA GGAGCCCCTG     360
ATGGTGCAGG CCAATGCAGA TGGGCGGCCC CGGAGCCGGC GGGCCCGGCA GTCAGAGGAA     420
CAAGCCCCCC TGGTGGAGTC CTACCTCAGC AGCAGTGGCA GCACCAGCTA CCAAGTTCAA     480
GAGGCCGACT CACTCGCCAG TGTGCAGCTG GGAGCCACGC GCCCAACAGC ACCAGCTTCA     540
GCCAAGAGAA CCAAGGCGGC AGCTACAGCA GGGGCCAGG  GTGGCGCCGC TAGGAAGGAG     600
AAGAAGGGAA AGCACAAAGG CACCAGCGGG CCAGCAGCAC TGGCAGAAGA CAAGTCTGAG     660
GCCCAAGGCC CAGTGCAGAT TCTGACTGTG GGCCAGTCAG ACCACGCCCA GGACGCAGGG     720
GAGACGGCAG CTGGTGGGGG CGAACGGCCC AGCGGGCAGG ATCTCCGTGC CACGATGCAG     780
AGGAAGGGCA TCTCCAGCAG CATGAGCTTT GACGAGGATG AGGAGGATGA GGAGGAGAAT     840
AGCTCCAGCT CCTCCCAGCT AAATAGTAAC ACCCGCCCCA GCTCTGCTAC TAGCAGGAAG     900
TCCGTCAGGG AGGCAGCCTC AGCCCCTAGC CCAACAGCTC CAGAGCAACC AGTGGACGTT     960
GAGGTCCAGG ATCTTGAGGA GTTTGCACTG AGGCCGGCCC CCAGGGTAT  CACCATCAAA    1020
TGCCGCATCA CTCGGGACAA GAAAGGGATG GACCGGGGCA TGTACCCCAC CTACTTTCTG    1080
CACCTGGACC GTGAGGATGG GAAGAAGGTG TTCCTCCTGG CGGGAAGGAA GAGAAAGAAG    1140
AGTAAAACTT CCAATTACCT CATCTCTGTG GACCCAACAG ACTTGTCTCG AGGAGGGGAC    1200
AGCTATATCG GAAACTGCG  GTCCAACTTG ATGGGCACCA AGTTCACTGT TTATGACAAT    1260
GGAGTCAACC CTCAGAAGGC CTCATCCTCC ACTTTGGAAA GTGGAACCTT ACGTCAGGAG    1320
CTGGCAGCTG TGTGCTACGA GACAAACGTC TTAGGCTTCA AGGGGCCTCG GAAGATGAGC    1380
GTGATTGTCC CAGGCATGAA CATGGTTCAT GAGAGAGTCT CTATCCGCCC CCGCAACGAG    1440
CATGAGACAC TGCTAGCACG CTGGCAGAAT AAGAACACGG AGAGTATCAT CGAGCTGCAA    1500
AACAAGACAC CTGTCTGGAA TGATGACACA CAGTCCTATG TACTCAACTT CCATGGGCGC    1560
GTCACACAGG CCTCCGTGAA GAACTTCCAG ATCATCCATG GCAATGACCC GGACTACATC    1620
GTGATGCAGT TTGGCCGGGT AGCAGAGGAT GTGTTCACCA TGGATTACAA CTACCCGCTG    1680
TGTGCACTGC AGGCCTTTGC CATTGCCCTG TCCAGCTTCG ACAGCAAGCT GGCGTGCGAG    1740
TAGAGGCCTC TTCGTGCCCT TTGGGGTTGC CCAGCCTGGA GCGGAGCTTG CCTGCCTGCC    1800
TGTGGAGACA GCCCTGCCTA TCCTCTGTAT ATAGGCCTTC CGCCAGATGA AGCTTTGGCC    1860
CTCAGTGGGC TCCCTGGCCC AGCCAGCCAG GAACTGGCTC CTTTGGCTCT GCTACTGAGG    1920
CAGGGGAGTA GTGGAGAGCG GGTGGGTGGG TGTTGAAGGG ATTGAGAATT AATTCTTTCC    1980
ATGCCACGAG GATCAACACA CACTCCCACC CTTGGGTAGT AAGTGGTTGT TGTNAGTCGG    2040
TACTTTACAA AGCTTGAGCA ACCTCTTCCA AGCTTGGGAA AGGGCCGCAA AAAGGCATTA    2100
GGAGGGGAG                                                           2109
```

(2) INFORMATION FOR SEQ ID NO:64:

(i) SEQUENCE CHARACTERISTICS:
        (A) LENGTH: 2088 base pairs (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:64:

```
TGGGCCAGGC CAAGACATGG TTCTAGAAAG CTTCTCCCAG GGAGCCAGGG ACTAAAGCCA      60
CTTGTAGAGA GTGTGCAGGG GTCTTAGAGA AAATATGCCT CAAACGGAAT GGCTTAAGCC     120
TGTTCCTGGG AAAGGTGGCC CAGGAAGGTA GAACTGTCTC TAGGAAATGA TCCTGTTCTA     180
GCAAGTGCCT AGGGCCCTGG CATCCTGCAA GGAGTGATTT GGCACTTGCC TCAGCCCAGT     240
GTCTTAGATG ATGAGGGCAG AAACCTGAGG CAGCAGAAGC TTGATCGGCA GCGGGCCCTG     300
CTGGAGCAGA AGCAGAAGAA GAAGCGCCAG GAGCCCCTGA TGGTGCAGGC CAATGCAGAT     360
GGGCGGCCCC GGAGCCGGCG GGCCCGGCAG TCAGAGGAAC AAGCCCCCCT GGTGGAGTCC     420
TACCTCAGCA GCAGTGGCAG CACCAGCTAC CAAGTTCAAG AGGCCGACTC ACTCGCCAGT     480
GTGCAGCTGG GAGCCACGCG CCCAACAGCA CCAGCTTCAG CCAAGAGAAC CAAGGCGGCA     540
GCTACAGCAG GGGGCCAGGG TGGCGCCGCT AGGAAGGAGA GAAGGGAAA GCACAAAGGC      600
ACCAGCGGGC CAGCAGCACT GGCAGAAGAC AAGTCTGAGG CCCAAGGCCC AGTGCAGATT     660
CTGACTGTGG GCCAGTCAGA CCACGCCCAG GACGCAGGGG AGACGGCAGC TGGTGGGGGC     720
GAACGGCCCA GCGGGCAGGA TCTCCGTGCC ACGATGCAGA GGAAGGGCAT CTCCAGCAGC     780
ATGAGCTTTG ACGAGGATGA GGAGGATGAG GAGGAGAATA GCTCCAGCTC CTCCCAGCTA     840
AATAGTAACA CCCGCCCCAG CTCTGCTACT AGCAGGAAGT CCGTCAGGGA GGCAGCCTCA     900
GCCCCTAGCC CAACAGCTCC AGAGCAACCA GTGGACGTTG AGGTCCAGGA TCTTGAGGAG     960
TTTGCACTGA GGCCGGCCCC CCAGGGTATC ACCATCAAAT GCCGCATCAC TCGGGACAAG    1020
AAAGGGATGG ACCGGGCAT GTACCCCACC TACTTTCTGC ACCTGGACCG TGAGGATGGG     1080
AAGAAGGTGT TCCTCCTGGC GGGAAGGAAG AGAAAGAAGA GTAAAACTTC CAATTACCTC    1140
ATCTCTGTGG ACCCAACAGA CTTGTCTCGA GGAGGGGACA GCTATATCGG GAAACTGCGG    1200
TCCAACTTGA TGGGCACCAA GTTCACTGTT TATGACAATG GAGTCAACCC TCAGAAGGCC    1260
TCATCCTCCA CTTTGGAAAG TGGAACCTTA CGTCAGGAGC TGGCAGCTGT GTGCTACGAG    1320
ACAAACGTCT TAGGCTTCAA GGGGCCTCGG AAGATGAGCG TGATTGTCCC AGGCATGAAC    1380
ATGGTTCATG AGAGTCTC TATCCGCCCC CGCAACGAGC ATGAGACACT GCTAGCACGC     1440
TGGCAGAATA GAACACGGA GAGTATCATC GAGCTGCAAA ACAAGACACC TGTCTGGAAT     1500
GATGACACAC AGTCCTATGT ACTCAACTTC CATGGGCGCG TCACACAGGC CTCCGTGAAG    1560
AACTTCCAGA TCATCCATGG CAATGACCCG GACTACATCG TGATGCAGTT TGGCCGGGTA    1620
GCAGAGGATG TGTTCACCAT GGATTACAAC TACCCGCTGT GTGCACTGCA GGCCTTTGCC    1680
ATTGCCCTGT CCAGCTTCGA CAGCAAGCTG GCGTGCGAGT AGAGGCCTCT TCGTGCCCTT    1740
TGGGGTTGCC CAGCCTGGAG CGGAGCTTGC CTGCCTGCCT GTGGAGACAG CCCTGCCTAT    1800
CCTCTGTATA TAGGCCTTCC GCCAGATGAA GCTTTGGCCC TCAGTGGGCT CCCTGGCCCA    1860
GCCAGCCAGG AACTGGCTCC TTTGGCTCTG CTACTGAGGC AGGGGAGTAG TGGAGAGCGG    1920
GTGGGTGGGT GTTGAAGGGA TTGAGAATTA ATTCTTTCCA TGCCACGAGG ATCAACACAC    1980
ACTCCCACCC TTGGGTAGTA AGTGGTTGTT GTNAGTCGGT ACTTTACCAA AGCTTGAGCA    2040
ACCTCTTCAA GCTTGGGAAA GGGCCGCAAA AAGGCATTAG GAGGGGAG                 2088
```

-continued (2) INFORMATION FOR SEQ ID NO:65:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

Lys Lys Lys Arg Gln
 1               5

(2) INFORMATION FOR SEQ ID NO:66:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Inosine
        (B) LOCATION: Positions 3, 6, 9

(xi) SEQUENCE DESCRIPTION: SEQ ID NO:66:

GCNTCNGTNA AGAACTTYCA GMT                                                  23

(2) INFORMATION FOR SEQ ID NO:67:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Inosine
        (B) LOCATION: Positions 6, 8, 9, 12, 15, 21

(xi) SEQUENCE DESCRIPTION: SEQ ID NO:67:

CTKSWNANNS MNATNGCRAA NGCYTG                                               26